US008377685B2

(12) United States Patent
Meyvantsson et al.

(10) Patent No.: US 8,377,685 B2
(45) Date of Patent: Feb. 19, 2013

(54) MICROFLUIDIC DEVICE HAVING STABLE STATIC GRADIENT FOR ANALYZING CHEMOTAXIS

(75) Inventors: Ivar Meyvantsson, Madison, WI (US); John Majer, Madison, WI (US); Steven Hayes, Madison, WI (US)

(73) Assignee: BellBrook Labs, LLC, Madison, WI (US)

( * ) Notice: Subject to any disclaimer, the term of this patent is extended or adjusted under 35 U.S.C. 154(b) by 1051 days.

(21) Appl. No.: 12/267,524

(22) Filed: Nov. 7, 2008

(65) Prior Publication Data

US 2009/0123961 A1 May 14, 2009

Related U.S. Application Data

(60) Provisional application No. 61/002,247, filed on Nov. 7, 2007.

(51) Int. Cl.

| | |
|---|---|
| ***G01N 33/53*** | (2006.01) |
| ***C12Q 1/24*** | (2006.01) |
| ***C12Q 1/20*** | (2006.01) |
| ***C12M 1/00*** | (2006.01) |
| ***C12M 3/00*** | (2006.01) |
| ***C12M 1/34*** | (2006.01) |

(52) U.S. Cl. .......... 435/288.5; 435/7.1; 435/30; 435/33; 435/283.1; 422/100

(58) Field of Classification Search ................... 435/7.1, 435/30, 33, 283.1, 288.5; 422/100
See application file for complete search history.

(56) References Cited

U.S. PATENT DOCUMENTS

| | | | | |
|---|---|---|---|---|
| 7,189,580 | B2 | 3/2007 | Beebe et al. | |
| 2003/0061687 | A1 | 4/2003 | Hansen et al. | |
| 2004/0142411 | A1 | 7/2004 | Kirk et al. | |
| 2007/0253868 | A1* | 11/2007 | Beebe et al. | 422/100 |
| 2011/0003372 | A1* | 1/2011 | Jeon et al. | 435/287.3 |

FOREIGN PATENT DOCUMENTS

| | | | |
|---|---|---|---|
| EP | 1741487 | A1 | 10/2007 |

OTHER PUBLICATIONS

Nuzzi, PA. et al., "Analysis of neutrophil chemotaxis," Methods in Molecular Biology 370:23-26 (2007).

* cited by examiner

*Primary Examiner* — Nathan Bowers
*Assistant Examiner* — Lydia Edwards
(74) *Attorney, Agent, or Firm* — Quarles & Brady LLP

(57) ABSTRACT

A microfluidic method and device for testing and analyzing chemotaxis by providing a stable, static fluid gradient. The device includes a sink reservoir for receiving biological cellular material and a source reservoir for receiving a chemoattractant. The biological cellular material migrates through a low fluid volume microfluidic gradient channel located between the source and sink reservoirs. The fluid in the gradient channel is static and stable due to a high fluid volume closed circuit bypass microfluidic channel also in fluid communication with the source and sink reservoirs, whereby the bypass channel relieves any pressure differential imparted across the gradient channel.

80 Claims, 15 Drawing Sheets a)

b)

c)

d)

MICROFLUIDIC DEVICE HAVING STABLE STATIC GRADIENT FOR ANALYZING CHEMOTAXIS

CROSS-REFERENCE TO RELATED APPLICATIONS

This application claims the benefit of U.S. Provisional Application No. 61/002,247 filed Nov. 7, 2007. The contents of this application are incorporated by reference here in its entirety.

STATEMENT REGARDING FEDERALLY SPONSORED RESEARCH OR DEVELOPMENT

This invention was made with United States government support awarded by the National Institutes of Health under grant number: R43HL088785-01. The United States government has certain rights in this invention.

BACKGROUND OF THE INVENTION

To study chemotaxis, several forms of gradient forming devices have been developed that vary in terms of ease-of-use and achievable throughput. The Dunn chamber consists of a central well surrounded by an annular well, whereby both structures are etched in a glass slide. The two wells are separated by an annular region that is shallower than the wells and lower than the top of the glass slide. The annular well is filled with a soluble factor solution, and the central well is filled with an appropriate buffer solution or cell culture medium.

Cells are seeded on a glass coverslip. The coverslip is laid on the slide containing the wells such that the cells are located within the area of the center well. The cells closing the shallow annular region separating the wells will see a gradient of the soluble factor. The cell movement in response to that gradient is recorded via video microscopy and analyzed using suitable software.

Microfluidic devices have been employed to create gradients and pattern cells. A gradient may be created in a microfluidic device by employing a network of successive branching and diffusive mixing units that form a gradient across the width of a microfluidic downstream channel. The stability of that gradient is reliant upon a constant flow through the device. Once constant flow ceases, the gradient dissipates and concentration becomes uniform across the channel. However, such microfluidic devices have important disadvantages. The flow biases the migration of cells in the direction of flow, which affects the results. The flow also removes soluble factors secreted by the cells, which abolishes important cell-to-cell signaling. Constant flow also utilizes an excessive fluid source that wastes expensive reagents.

Other microfluidic devices produce gradients without flow. Static gradients avoid some disadvantages of flowing microfluidic devices, however, they have other disadvantages. Static microfluidic devices employ microfluidic channels having a small volume. Small disturbances can easily distort or eliminate a gradient that exists in a small-volume microfluidic channel. Several important sources of disturbance can be identified. A fluid level difference between access ports on the ends of a microfluidic channel may produce flow due to gravity. Surface tension significantly influences the length scale of microfluidic channels. Any differences in radius of curvature of the air-liquid interface of access ports produce a pressure differential between the ports that tends to produce flow. Evaporation is proportional to several parameters, such as the surface area of the air-liquid interface, the exponent of negative one over the ambient temperature, ambient humidity, and air convection. Evaporation causes an imbalance in fluid level or radius of curvature, which causes fluid flow and an unstable gradient. Evaporation is proportional to the vapor pressure of the fluid. The vapor pressure is proportional to $\exp(-H/RT)$, where H is the enthalpy of vaporization.

Therefore, since there is a long felt need in the industry for a microfluidic gradient device, alternative methods and microfluidic devices described herein below make a desirable contribution.

SUMMARY OF THE INVENTION

The present invention is broadly summarized as a novel and non-obvious device and method providing a stable, static fluid gradient on a microfluidic scale, which is suitable for testing and analyzing chemotaxis.

One aspect of the invention is a microfluidic gradient device comprising a source assembly comprising a source port, having a source port area and source port perimeter, and a source reservoir, where the source port is connected to the source reservoir, and the source assembly is adapted to contain a source liquid volume in the range of 25 pL to 15 μL defining an air/liquid interface within the source port having a source port radius of curvature, a sink assembly comprising a sink port, having a sink port area and a sink port perimeter, and a sink reservoir, where the sink port is connected to the sink reservoir, and the sink assembly is adapted to contain a sink liquid volume in the range of 500 pL to 100 μL defining an air/liquid interface within the sink port having a sink port radius of curvature, a gradient channel having a gradient height, gradient width, gradient length and gradient transverse cross-sectional area and having a gradient flow resistance in the range of $1\times10^{8}$ to $1\times10^{18}$ N-s-m$^{-5}$ and having a gradient contact angle and adapted to contain a gradient liquid volume in the range of 500 fL to 6 μL in fluid communication between the source and sink reservoirs, and, a closed circuit channel having a circuit height, circuit width, circuit length, and circuit transverse cross-sectional area and having a circuit flow resistance in the range of $1\times10^{6}$ to $1\times10^{15}$ N-s-m$^{-5}$ and having a circuit contact angle and adapted to contain a circuit liquid volume in the range of 50 pL to 400 μL and in fluid communication with the source and sink reservoirs, wherein the ratio of the (gradient flow resistance):(circuit flow resistance) is in the range of (10-10,000):1.

In an exemplary embodiment of the microfluidic gradient device, the gradient height is in the range of 1 μm to 200 μm.

In another exemplary embodiment of the microfluidic gradient device, the gradient width is in the range of 10 μm to 3 mm.

In another exemplary embodiment of the microfluidic gradient device, the gradient length is in the range of 50 μm to 10 mm.

In another exemplary embodiment of the microfluidic gradient device, the circuit height is in the range of 10 μm to 2 mm.

In another exemplary embodiment of the microfluidic gradient device, the circuit width is in the range of 50 μm to 4 mm.

In another exemplary embodiment of the microfluidic gradient device, the circuit length is in the range of 100 μm to 50 mm.

In another exemplary embodiment of the microfluidic gradient device, the gradient transverse cross-sectional area is in the range of 10 μm$^2$ to $6\times10^{5}$ μm$^2$ In another exemplary embodiment of the microfluidic gradient device, the circuit transverse cross-sectional area is in the range of 500 $\mu m^2$ to $8\times10^6$ $\mu m^2$.

In another exemplary embodiment of the microfluidic gradient device, the source port area is in the range of 900 $\mu m^2$ to 9 $mm^2$.

In another exemplary embodiment of the microfluidic gradient device, the sink port area is in the range of 2500 $\mu m^2$ to 81 $mm^2$.

In another exemplary embodiment of the microfluidic gradient device, useful for chemotaxis assays, the gradient height is in the range of 15 μm to 200 μm.

In another exemplary embodiment of the microfluidic gradient device, useful for chemotaxis assays, the gradient width is in the range of 100 μm to 3 mm.

In another exemplary embodiment of the microfluidic gradient device, useful for chemotaxis assays, the gradient length is the range of 500 μm to 4 mm.

In another exemplary embodiment of the microfluidic gradient device, useful for chemotaxis assays, the circuit height is in the range of 100 μm to 2 mm.

In another exemplary embodiment of the microfluidic gradient device, useful for chemotaxis assays, the circuit width is in the range of 500 μm to 4 mm.

In another exemplary embodiment of the microfluidic gradient device, useful for chemotaxis assays, the circuit length is in the range of 3 mm to 30 mm.

In another exemplary embodiment of the microfluidic gradient device, useful for chemotaxis assays, the gradient transverse cross-sectional area is in the range of 1500 $\mu m^2$ to $6\times10^5$ $\mu m^2$.

In another exemplary embodiment of the microfluidic gradient device, useful for chemotaxis assays, the circuit transverse cross-sectional area is in the range of $1\times10^5$ $\mu m^2$ to $8\times10^6$ $\mu m^2$.

In another exemplary embodiment of the microfluidic gradient device, useful for chemotaxis assays, the source port area is in the range of 2500 $\mu m^2$ to 9 $mm^2$.

In another exemplary embodiment of the microfluidic gradient device, useful for chemotaxis assays, the sink port area is in the range of $1\times10^4$ $\mu m^2$ to 81 $mm^2$.

In an exemplary embodiment of the microfluidic gradient device, the gradient height is around 25 μm.

In another exemplary embodiment of the microfluidic gradient device, the gradient width is around 1 mm.

In another exemplary embodiment of the microfluidic gradient device, the gradient length is in around 3 mm.

In another exemplary embodiment of the microfluidic gradient device, the circuit height is around 250 μm.

In another exemplary embodiment of the microfluidic gradient device, the circuit width is in around 1 mm.

In another exemplary embodiment of the microfluidic gradient device, the circuit length is around 20 mm.

In another exemplary embodiment of the microfluidic gradient device, the gradient transverse cross-sectional area is around $2.5\times10^4$ $\mu m^2$.

In another exemplary embodiment of the microfluidic gradient device, the circuit transverse cross-sectional area is around $2.5\times10^5$ $\mu m^2$.

In another exemplary embodiment of the microfluidic gradient device, the ratio of the (gradient flow resistance):(circuit flow resistance) is around 200:1.

In another exemplary embodiment of the microfluidic gradient device, the gradient liquid volume is around 75 nL.

In another exemplary embodiment of the microfluidic gradient device, the circuit liquid volume is around 5 μL.

In another exemplary embodiment of the microfluidic gradient device, the gradient flow resistance is around $2\times10^{12}$ $N\text{-}s\text{-}m^{-5}$.

In another exemplary embodiment of the microfluidic gradient device, the circuit flow resistance is around $1\times10^{10}$ $N\text{-}s\text{-}m^{-5}$.

In another exemplary embodiment of the microfluidic gradient device, the source liquid volume is around 0.5 μL.

In another exemplary embodiment of the microfluidic gradient device, the sink liquid volume is around 16 μL.

In another exemplary embodiment of the microfluidic gradient device, the source port area is around 0.8 $mm^2$.

In another exemplary embodiment of the microfluidic gradient device, the sink port area is in around 2 $mm^2$.

In another exemplary embodiment of the microfluidic gradient device, the inner surface of the gradient channel has a gradient contact angle in the range of 0° to 60°, and wherein the inner surface of the closed-circuit channel has a closed-circuit contact angle in the range of 0° to 60°.

In another exemplary embodiment of the microfluidic gradient device, the source port radius of curvature and the sink port radius of curvature are equal when gradient and circuit liquid volumes are in flow equilibrium.

In another exemplary embodiment of the microfluidic gradient device, the transverse cross-sectional shape of the gradient channel is rectangular or curvalinear, wherein the longitudinal cross-sectional shape of the gradient channel is rectangular or curvalinear, wherein the transverse cross-sectional shape of the closed circuit channel is rectangular or curvalinear, and wherein the longitudinal cross-sectional shape of the closed circuit channel is rectangular or curvalinear.

In another exemplary embodiment of the microfluidic gradient device, the device is constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

In another exemplary embodiment of the microfluidic gradient device, the sink assembly further comprises an air vent port, having an air vent port area in the range of 900 $\mu m^2$ to 9 $mm^2$, and where the air vent port is connected to the sink reservoir.

In another exemplary embodiment of the microfluidic gradient device, the device further comprises a source assembly comprising a source port, having a source port area and source port perimeter, and a source reservoir, where the source port is connected to the source reservoir, and the source assembly is adapted to contain a source liquid volume in the range of 25 pL to 15 μL defining an air/liquid interface within the source port having a source port radius of curvature, a sink assembly comprising a sink port having a sink port area and sink port perimeter, and comprising a sink reservoir, and comprising a cell addition port having a cell addition port area and a cell addition port perimeter, and comprising a cell addition reservoir, where the sink port is connected to the sink reservoir, and where the cell addition port is connected to the cell addition reservoir, and where the cell addition reservoir is in fluidic communication with the sink reservoir, and the sink assembly is adapted to contain a sink liquid volume in the range of 500 pL to 100 μL defining an air/liquid interface within the sink port having a sink port radius of curvature, and defining an air/liquid interface within the cell addition port having a cell addition port radius of curvature, a gradient channel having a gradient height, gradient width, gradient length and gradient transverse cross-sectional area and having a gradient flow resistance in the range of $1\times10^8$ to $1\times10^{18}$ $N\text{-}s\text{-}m^{-5}$ and having a gradient contact angle and adapted to contain a gradient liquid volume in the range of 500 fL to 6 μL in fluid communication between the source and sink reservoirs, and, a closed circuit channel having a circuit height, circuit width, circuit length, and circuit transverse cross-sectional area and having a circuit flow resistance in the range of $1\times10^6$ to $1\times10^{15}$ $N\text{-}s\text{-}m^{-5}$ and having a circuit contact angle and adapted to contain a circuit liquid volume in the range of 50 pL to 400 μL and in fluid communication with the source and sink reservoirs, wherein the ratio of the (gradient flow resistance):(circuit flow resistance) is in the range of (10-10,000):1.

In another exemplary embodiment of the microfluidic gradient device, useful for chemotaxis assays, the gradient height is in the range of 15 μm to 200 μm.

In another exemplary embodiment of the microfluidic gradient device, useful for chemotaxis assays, the gradient width is in the range of 100 μm to 3 mm.

In another exemplary embodiment of the microfluidic gradient device, useful for chemotaxis assays, the gradient length is in the range of 500 μm to 4 mm.

In another exemplary embodiment of the microfluidic gradient device useful for chemotaxis assays, the circuit height is in the range of 100 μm to 2 mm.

In another exemplary embodiment of the microfluidic gradient device, useful for chemotaxis assays, the circuit width is in the range of 500 μm to 4 mm.

In another exemplary embodiment of the microfluidic gradient device, useful for chemotaxis assays, the circuit length is in the range of 3 mm to 30 mm.

In another exemplary embodiment of the microfluidic gradient device, useful for chemotaxis assays, the gradient transverse cross-sectional area is in the range of 1500 $\mu m^2$ to $6\times10^5$ $\mu m^2$.

In another exemplary embodiment of the microfluidic gradient device, useful for chemotaxis assays, the circuit transverse cross-sectional area is in the range of $1\times10^5$ $\mu m^2$ to $8\times10^6$ $\mu m^2$.

In another exemplary embodiment of the microfluidic gradient device, useful for chemotaxis assays, the source port area is in the range of 2500 $\mu m^2$ to 9 $mm^2$.

In another exemplary embodiment of the microfluidic gradient device, useful for chemotaxis assays, wherein the sink port area is in the range of $1\times10^4$ $\mu m^2$ to 81 $mm^2$.

In another exemplary embodiment of the microfluidic gradient device, useful for chemotaxis assays, the cell addition port area is in the range of 2500 $\mu m^2$ to 9 $mm^2$.

In an exemplary embodiment of the microfluidic gradient device, the gradient height is around 50 μm.

In another exemplary embodiment of the microfluidic gradient device, the gradient width is around 1 mm.

In another exemplary embodiment of the microfluidic gradient device, the gradient length is in around 3.5 mm.

In another exemplary embodiment of the microfluidic gradient device, the circuit height is around 1 mm.

In another exemplary embodiment of the microfluidic gradient device, the circuit width is in around 1 mm.

In another exemplary embodiment of the microfluidic gradient device, the circuit length is around 6 mm.

In another exemplary embodiment of the microfluidic gradient device, the gradient transverse cross-sectional area is around $5\times10^4$ $\mu m^2$.

In another exemplary embodiment of the microfluidic gradient device, the circuit transverse cross-sectional area is around $1\times10^6$ $\mu m^2$.

In another exemplary embodiment of the microfluidic gradient device, the ratio of the (gradient flow resistance):(circuit flow resistance) is around 5000:1.

In another exemplary embodiment of the microfluidic gradient device, the gradient liquid volume is around 175 nL.

In another exemplary embodiment of the microfluidic gradient device, the circuit liquid volume is around 6 μL.

In another exemplary embodiment of the microfluidic gradient device, the gradient flow resistance is around $3.5\times10^{11}$ $N\text{-}s\text{-}m^{-5}$.

In another exemplary embodiment of the microfluidic gradient device, the circuit flow resistance is around $7\times10^7$ $N\text{-}s\text{-}m^{-5}$.

In another exemplary embodiment of the microfluidic gradient device, the source liquid volume is around 1.5 μL.

In another exemplary embodiment of the microfluidic gradient device, the sink liquid volume is around 11 μL.

In another exemplary embodiment of the microfluidic gradient device, the source port area is around 0.8 $mm^2$.

In another exemplary embodiment of the microfluidic gradient device, the sink port area is in around 3 $mm^2$.

In another exemplary embodiment of the microfluidic gradient device, the cell addition port area is in around 0.8 $mm^2$.

In another exemplary embodiment of the microfluidic gradient device, the wherein the inner surface of the gradient channel has a gradient contact angle in the range of 0° to 60°, and wherein the inner surface of the closed-circuit channel has a closed-circuit contact angle in the range of 0° to 60°.

In another exemplary embodiment of the microfluidic gradient device, the source port radius of curvature, the cell addition port radius of curvature, and the sink port radius of curvature are equal when gradient and circuit liquid volumes are in flow equilibrium.

In another exemplary embodiment of the microfluidic gradient device, the transverse cross-sectional shape of the gradient channel is rectangular or curvalinear, the longitudinal cross-sectional shape of the gradient channel is rectangular or curvalinear, the transverse cross-sectional shape of the closed circuit channel is rectangular or curvalinear, and the longitudinal cross-sectional shape of the closed circuit channel is rectangular or curvalinear.

In another exemplary embodiment of the microfluidic gradient device, the shape of the source port perimeter is rectangular, polygonal or curvilinear, the shape of the cell addition port perimeter is rectangular, polygonal or curvilinear, and the shape of the sink port perimeter is rectangular, polygonal or curvilinear.

In another exemplary embodiment of the microfluidic gradient device, the device is constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

In another exemplary embodiment of the microfluidic gradient device, the sink assembly further comprises an air vent port, having an air vent port area in the range of 900 $\mu m^2$ to 9 $mm^2$, and where the air vent port is connected to the sink reservoir.

Another aspect of the invention is a microfluidic chemotaxis gradient device comprising a source assembly comprising a source port, having a source port area and source port perimeter, and a source reservoir, where the source port is connected to the source reservoir, and the source assembly is adapted to contain a source liquid volume in the range of 25 pL to 15 μL defining an air/liquid interface within the source port having a source port radius of curvature, a sink assembly comprising a sink port, having a sink port area and a sink port perimeter, and a sink reservoir, where the sink port is connected to the sink reservoir, and the sink assembly is adapted to contain a sink liquid volume in the range of 500 pL to 100

μL defining an air/liquid interface within the sink port having a sink port radius of curvature, a gradient assembly comprising a gradient channel having a gradient height, gradient width, gradient length and gradient transverse cross-sectional area and having a gradient flow resistance in the range of $1\times10^8$ to $1\times10^{18}$ N-s-m$^{-5}$ and having a gradient contact angle, and comprising a cell addition port having a cell addition port area and cell addition port perimeter, and comprising a cell addition reservoir, where the cell addition port is connected to the cell addition reservoir and where the cell addition reservoir is in fluidic communication with the gradient channel, and where the gradient assembly is adapted to contain a gradient liquid volume in the range of 25 pL to 6 μL, defining an air/liquid interface within the cell addition port, having a cell addition port radius of curvature, and where the gradient liquid volume is in fluid communication between the source and sink reservoirs, and, a closed circuit channel having a circuit height, circuit width, circuit length, and circuit transverse cross-sectional area and having a circuit flow resistance in the range of $1\times10^6$ to $1\times10^{15}$ N-s-m$^{-5}$ and having a circuit contact angle and adapted to contain a circuit liquid volume in the range of 50 pL to 400 μL and in fluid communication with the source and sink reservoirs, and the ratio of the (gradient flow resistance):(circuit flow resistance) is in the range of (10-10,000):1.

In another exemplary embodiment of the microfluidic gradient device, the gradient height is in the range of 1 μm to 200 μm.

In another exemplary embodiment of the microfluidic gradient device, the gradient width is in the range of 10 μm to 3 mm.

In another exemplary embodiment of the microfluidic gradient device, the gradient length is in the range of 50 μm to 10 mm.

In another exemplary embodiment of the microfluidic gradient device, the circuit height is in the range of 10 μm to 2 mm.

In another exemplary embodiment of the microfluidic gradient device, the circuit width is in the range of 50 μm to 4 mm.

In another exemplary embodiment of the microfluidic gradient device, the circuit length is in the range of 100 μm to 50 mm.

In another exemplary embodiment of the microfluidic gradient device, the gradient transverse cross-sectional area is in the range of 10 μm$^2$ to $6\times10^5$ μm$^2$ In another exemplary embodiment of the microfluidic gradient device, wherein the circuit transverse cross-sectional area is in the range of 500 μm$^2$ to $8\times10^6$ μm$^2$.

In another exemplary embodiment of the microfluidic gradient device, the source port area is in the range of 900 μm$^2$ to 9 mm$^2$.

In another exemplary embodiment of the microfluidic gradient device, the sink port area is in the range of 2500 μm$^2$ to 81 mm$^2$.

In another exemplary embodiment of the microfluidic gradient device, the cell addition port area is in the range of 900 μm$^2$ to 9 mm$^2$.

In another exemplary embodiment of the microfluidic gradient device, useful for chemotaxis assays, the gradient height is in the range of 15 μm to 200 μm, the gradient width is in the range of 100 μm to 3 mm, the gradient length is in the range of 500 μm to 4 mm, the circuit height is in the range of 100 μm to 2 mm, the circuit width is in the range of 500 μm to 4 mm, the circuit length is in the range of 3 mm to 30 mm, the gradient transverse cross-sectional area is in the range of 1500 μm$^2$ to $6\times10^5$ μm$^2$, the circuit transverse cross-sectional area is in the range of $1\times10^5$ μm$^2$ to $8\times10^6$ μm$^2$, the source port area is in the range of 2500 μm$^2$ to 9 mm$^2$, the sink port area is in the range of $1\times10^4$ μm$^2$ to 81 mm$^2$, and the cell addition port area is in the range of 2500 μm$^2$ to 9 mm$^2$.

In another exemplary embodiment of the microfluidic gradient device, the gradient height is around 50 μm, the gradient width is around 1 mm, n the gradient length is around 3 mm, the circuit height is around 1 mm, the circuit width is around 1 mm, the circuit length is around 10 mm, the gradient transverse cross-sectional area is around $5\times10^4$ μm$^2$, the circuit transverse cross-sectional area is around $2.1\times10^6$ μm$^2$, the ratio of the (gradient flow resistance):(circuit flow resistance) is around 3000:1, the gradient liquid volume is around 150 nL, the circuit liquid volume is around 10 μL, the gradient flow resistance is around $3\times10^{11}$ N-s-m$^{-5}$, the circuit flow resistance is around $1\times10^8$ N-s-m$^{-5}$, the source liquid volume is around 1.5 μL, the sink liquid volume is around 6 μL, the source port area is around 0.8 mm$^2$, the sink port area is around 3 mm$^2$ and, the cell addition port area is around 0.8 mm$^2$.

In another exemplary embodiment of the microfluidic gradient device, the inner surface of the gradient channel has a gradient contact angle in the range of 0° to 60°, and the inner surface of the closed-circuit channel has a closed-circuit contact angle in the range of 0° to 60°.

In another exemplary embodiment of the microfluidic gradient device, the source port radius of curvature, the cell addition port radius of curvature and the sink port radius of curvature are equal when gradient and circuit liquid volumes are in flow equilibrium.

In another exemplary embodiment of the microfluidic gradient device, the transverse cross-sectional shape of the gradient channel is rectangular or curvalinear, the longitudinal cross-sectional shape of the gradient channel is rectangular or curvalinear, the transverse cross-sectional shape of the closed circuit channel is rectangular or curvalinear, and the longitudinal cross-sectional shape of the closed circuit channel is rectangular or curvalinear.

In another exemplary embodiment of the microfluidic gradient device, the shape of the source port perimeter is rectangular, polygonal or curvilinear, the shape of the cell addition port perimeter is rectangular, polygonal or curvilinear, and the shape of the sink port perimeter is rectangular, polygonal or curvilinear.

In another exemplary embodiment of the microfluidic gradient device, the device is constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

In another exemplary embodiment of the microfluidic gradient device, the sink assembly further comprises an air vent port, having an air vent port area in the range of 900 μm$^2$ to 9 mm$^2$, and where the air vent port is connected to the sink reservoir.

Another aspect of the invention is a microfluidic gradient device comprising a source assembly comprising a source port, having a source port area and source port perimeter, and comprising a source reservoir, where the source port is connected to the source reservoir, and the source assembly is adapted to contain a source liquid volume in the range of 25 pL to 15 μL defining an air/liquid interface within the source port having a source port radius of curvature, a sink assembly comprising a sink port, having a sink port area and a sink port perimeter, and comprising a sink reservoir, where the sink port is connected to the sink reservoir, and the sink assembly is adapted to contain a sink liquid volume in the range of 500 pL to 100 μL defining an air/liquid interface within the sink port having a sink port radius of curvature, a gradient channel having a gradient height, gradient width, gradient length and gradient transverse cross-sectional area and having a gradient flow resistance in the range of $1\times10^{8}$ to $1\times10^{18}$ N-s-$m^{-5}$ and having a gradient contact angle and adapted to contain a gradient liquid volume in the range of 500 fL to 6 μL in fluid communication between the source and sink reservoirs, and, a closed circuit channel having a circuit height, circuit width, circuit length, and circuit transverse cross-sectional area and having a circuit flow resistance in the range of $1\times10^{6}$ to $1\times10^{15}$ N-s-$m^{-5}$ and having a circuit contact angle and adapted to contain a circuit liquid volume in the range of 50 pL to 400 μL and in fluid communication with the source and sink reservoirs, a cell seeding assembly comprising a cell addition port, having a cell addition port area and a cell addition port perimeter, and comprising a cell addition reservoir, and comprising a cell addition channel having a cell addition height, cell addition width, cell addition length and cell addition transverse cross-sectional area, and having a cell addition flow resistance in the range of $5\times10^{6}$ to $6\times10^{3}$ N-s-$m^{-5}$, where the cell addition port is connected to the cell addition reservoir, and where the cell addition assembly is adapted to contain a cell addition liquid volume in the range of 30 pL to 65 μL defining an air/liquid interface within the cell addition port having a cell addition port radius of curvature, and the ratio of the (gradient flow resistance):(circuit flow resistance) is in the range of (10-10,000):1.

In an exemplary embodiment of the microfluidic gradient device, the gradient height is in the range of 1 μm to 200 μm, the gradient width is in the range of 10 μm to 3 mm, the gradient length is in the range of 50 μm to 10 mm, the circuit height is in the range of 10 μm to 2 mm, the circuit width is in the range of 50 μm to 4 mm, the circuit length is in the range of 100 μm to 50 mm, the cell addition height is in the range of 10 μm to 2 mm, the cell addition width is in the range of 10 μm to 3 mm, the cell addition length is in the range of 50 μm to 10 mm, the gradient transverse cross-sectional area is in the range of 10 $\mu m^2$ to $6\times10^{5}$ $\mu m^2$, the circuit transverse cross-sectional area is in the range of 500 $\mu m^2$ to $8\times10^{6}$ $\mu m^2$, the cell addition transverse cross-sectional area is in the range of 100 $\mu m^2$ to $6\times10^{6}$ $\mu m^2$, the source port area is in the range of 900 $\mu m^2$ to 9 $mm^2$, the sink port area is in the range of 2500 $\mu m^2$ to 81 $mm^2$, and the cell addition port area is in the range of 900 $\mu m^2$ to 9 $mm^2$.

In an exemplary embodiment of the microfluidic gradient device, useful for chemotaxis assays, the gradient height is in the range of 15 μm to 200 μm, the gradient width is in the range of 100 μm to 3 mm, the gradient length is in the range of 500 μm to 4 mm, circuit height is in the range of 100 μm to 2 mm, the circuit width is in the range of 500 μm to 4 mm, the circuit length is in the range of 3 mm to 30 mm, the cell addition height is in the range of 100 μm to 2 mm, the cell addition width is in the range of 100 μm to 3 mm, the cell addition length is in the range of 500 μm to 4 mm, the gradient transverse cross-sectional area is in the range of 1500 $\mu m^2$ to $6\times10^{5}$ $\mu m^2$, the circuit transverse cross-sectional area is in the range of $1\times10^{5}$ $\mu m^2$ to $8\times10^{6}$ $\mu m^2$, the cell addition transverse cross-sectional area is in the range of $2\times10^{4}$ $\mu m^2$ to $6\times10^{6}$ $\mu m^2$, the source port area is in the range of 2500 $\mu m^2$ to 9 $mm^2$, the sink port area is in the range of $1\times10^{4}$ $\mu m^2$ to 81 $mm^2$, and the cell addition port area is in the range of 2500 $\mu m^2$ to 9 $mm^2$.

In another exemplary embodiment of the microfluidic gradient device, the gradient height is around 50 μm, the gradient width is around 1 mm, the gradient length is around 3 mm, circuit height is around 1 mm, the circuit width is around 1 mm, the circuit length is around 10 mm, cell addition height is around 1 mm, the cell addition width is around 1 mm, the cell addition length is around 1.5 mm, the gradient transverse cross-sectional area is around $5\times10^{4}$ $\mu m^2$, the circuit transverse cross-sectional area is around $1\times10^{6}$ $\mu m^2$, the cell addition transverse cross-sectional area is around $1\times10^{6}$ $\mu m^2$, the ratio of the (gradient flow resistance):(circuit flow resistance) is around 3000:1, the gradient liquid volume is around 150 nL, the circuit liquid volume is around 10 μL, the gradient flow resistance is around $3\times10^{11}$ N-s-$m^{-5}$, the circuit flow resistance is around $1\times10^{8}$ N-s-$m^{-5}$, the cell addition flow resistance is around $2\times10^{7}$ N-s-$m^{-5}$, the source liquid volume is around 1.5 μL, the sink liquid volume is around 6 μL, the cell addition liquid volume is around 1.5 μL, the source port area is around 0.8 $mm^2$, the sink port area is around 3 $mm^2$, and the cell addition port area is around 0.8 $mm^2$.

In another exemplary embodiment of the microfluidic gradient device, the inner surface of the gradient channel has a gradient contact angle in the range of 0° to 60°, the inner surface of the closed-circuit channel has a closed-circuit contact angle in the range of 0° to 60°, and the inner surface of the cell addition channel has a cell addition contact angle in the range of 0° to 60°.

In another exemplary embodiment of the microfluidic gradient device, the source port radius of curvature, cell addition port radius of curvature, and the sink port radius of curvature are equal when gradient, circuit, and cell addition liquid volumes are in flow equilibrium.

In another exemplary embodiment of the microfluidic gradient device, the transverse cross-sectional shape of the gradient channel is rectangular or curvalinear, the longitudinal cross-sectional shape of the gradient channel is rectangular or curvalinear, the transverse cross-sectional shape of the closed circuit channel is rectangular or curvalinear, the longitudinal cross-sectional shape of the closed circuit channel is rectangular or curvalinear, the transverse cross-sectional shape of the cell addition channel is rectangular or curvalinear, and the longitudinal cross-sectional shape of the cell addition channel is rectangular or curvalinear.

In another exemplary embodiment of the microfluidic gradient device, the shape of the source port perimeter is rectangular, polygonal or curvilinear, the shape of the sink port perimeter is rectangular, polygonal or curvilinear, and the shape of the cell addition port perimeter is rectangular, polygonal or curvilinear.

In another exemplary embodiment of the microfluidic gradient device, the device is constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

In another exemplary embodiment of the microfluidic gradient device, the sink assembly further comprises an air vent port, having an air vent port area in the range of 900 $\mu m^2$ to 9 $mm^2$, and the air vent port is connected to the sink reservoir.

Another aspect of the invention is a microfluidic gradient device comprising a source assembly comprising a source port, having a source port area and source port perimeter, and comprising a source reservoir, and comprising a source input reservoir, and comprising a source auxiliary channel having an auxiliary height, auxiliary width, auxiliary length and auxiliary transverse cross-sectional area, having an auxiliary flow resistance in the range of $1\times10^{6}$ to $1\times10^{15}$ N-s-$m^{-5}$, and having an auxiliary contact angle, and where the source port is connected to the source input reservoir, and where the source auxiliary channel is in fluidic communication with the source input reservoir and the source reservoir, and where the source assembly is adapted to contain a source liquid volume in the range of 75 pL to 110 μL defining an air/liquid interface within the source port having a source port radius of curvature, a sink assembly comprising a sink port, having a sink port area and a sink port perimeter, and a sink reservoir, where the sink port is connected to the sink reservoir, and the sink assembly is adapted to contain a sink liquid volume in the range of 500 pL to 100 μL defining an air/liquid interface within the sink port having a sink port radius of curvature, a gradient channel having a gradient height, gradient width, gradient length and gradient transverse cross-sectional area and having a gradient flow resistance in the range of $1\times10^{8}$ to $1\times10^{18}$ N-s-$m^{-5}$ and having a gradient contact angle and adapted to contain a gradient liquid volume in the range of 500 fL to 6 μL in fluid communication between the source and sink reservoirs, and, a closed circuit channel having a circuit height, circuit width, circuit length, and circuit transverse cross-sectional area and having a circuit flow resistance in the range of $1\times10^{6}$ to $1\times10^{15}$ N-s-$m^{-5}$ and having a circuit contact angle and adapted to contain a circuit liquid volume in the range of 50 pL to 400 μL and in fluid communication with the source and sink reservoirs, the ratio of the (gradient flow resistance):(circuit flow resistance) is in the range of (10-10,000):1.

In another exemplary embodiment of the microfluidic gradient device, the gradient height is in the range of 1 μm to 200 μm, wherein the gradient width is in the range of 10 μm to 3 mm, wherein the gradient length is in the range of 50 μm to 10 mm, wherein circuit height is in the range of 10 μm to 2 mm, wherein the circuit width is in the range of 50 μm to 4 mm, wherein the circuit length is in the range of 100 μm to 50 mm, wherein the auxiliary height is in the range of 10 μm to 2 mm, wherein the auxiliary width is in the range of 50 μm to 4 mm, wherein the auxiliary length is in the range of 50 μm to 10 mm, wherein the gradient transverse cross-sectional area is in the range of 10 $\mu m^2$ to $6\times10^{5}$ $\mu m^2$, wherein the circuit transverse cross-sectional area is in the range of 500 $\mu m^2$ to $8\times10^{6}$ $m^2$, wherein the auxiliary transverse cross-sectional area is in the range of 500 $\mu m^2$ to $8\times10^{6}$ $\mu m^2$, wherein the source port area is in the range of 900 $\mu m^2$ to 9 $mm^2$, and wherein the sink port area is in the range of 2500 $\mu m^2$ to 81 $mm^2$.

In another exemplary embodiment of the microfluidic gradient device, useful for chemotaxis assays, the gradient height is in the range of 15 μm to 200 μm, the gradient width is in the range of 100 μm to 3 mm, the gradient length is in the range of 500 μm to 4 mm, circuit height is in the range of 100 μm to 2 mm, the circuit width is in the range of 500 μm to 4 mm, the circuit length is in the range of 3 mm to 30 mm, the auxiliary height is in the range of 100 μm to 2 mm, the auxiliary width is in the range of 500 μm to 4 mm, the auxiliary length is in the range of 500 μm to 5 mm, the gradient transverse cross-sectional area is in the range of 1500 $\mu m^2$ to $6\times10^{5}$ $\mu m^2$, the circuit transverse cross-sectional area is in the range of $1\times10^{5}$ $\mu m^2$ to $8\times10^{6}$ $\mu m^2$, the auxiliary transverse cross-sectional area is in the range of $5\times10^{4}$ $\mu m^2$ to $8\times10^{6}$ $\mu m^2$, the source port area is in the range of 2500 $\mu m^2$ to 9 $mm^2$, and the sink port area is in the range of $1\times10^{4}$ $\mu m^2$ to 81 $mm^2$.

In another exemplary embodiment of the microfluidic gradient device, the gradient height is around 100 μm, the gradient width is around 2 mm, the gradient length is around 1 mm, the circuit height is around 1 mm, the circuit width is around 1 mm, the circuit length is around 9 mm, the auxiliary height is around 100 μm, the auxiliary width is around 1 mm, the auxiliary length is around 3 mm, the gradient transverse cross-sectional area is around $2\times10^{5}$ $\mu m^2$, the circuit transverse cross-sectional area is around $1\times10^{6}$ $\mu m^2$, the auxiliary transverse cross-sectional area is around $1\times10^{5}$ $\mu m^2$, the ratio of the (gradient flow resistance):(circuit flow resistance) is around 60:1, the gradient liquid volume is around 200 nL, the circuit liquid volume is around 9 μL, the auxiliary liquid volume is around 300 nL, the gradient flow resistance is around $6\times10^{9}$ N-s-$m^{-5}$, the circuit flow resistance is around $1\times10^{8}$ N-s-$m^{-5}$, the auxiliary flow resistance is around $3\times10^{10}$ N-s-$m^{-5}$, the source liquid volume is around 3 μL, the sink liquid volume is around 15 μL, the source input liquid volume is around 1.6 μL, the source port area is around 0.8 $mm^2$, and, the sink port area is around 2 $mm^2$.

In another exemplary embodiment of the microfluidic gradient device, the inner surface of the gradient channel has a gradient contact angle in the range of 0° to 60°, wherein the inner surface of the closed-circuit channel has a closed-circuit contact angle in the range of 0° to 60°, and wherein the inner surface of the auxiliary channel has a gradient contact angle in the range of 0° to 60°.

In another exemplary embodiment of the microfluidic gradient device, the source port radius of curvature and the sink port radius of curvature are equal when gradient, circuit, and auxiliary liquid volumes are in flow equilibrium.

In another exemplary embodiment of the microfluidic gradient device, the transverse cross-sectional shape of the gradient channel is rectangular or curvalinear, the longitudinal cross-sectional shape of the gradient channel is rectangular or curvalinear, the transverse cross-sectional shape of the closed circuit channel is rectangular or curvalinear, the longitudinal cross-sectional shape of the closed circuit channel is rectangular or curvalinear, and the transverse cross-sectional shape of the auxiliary channel is rectangular or curvalinear, the longitudinal cross-sectional shape of the auxiliary channel is rectangular or curvalinear.

In another exemplary embodiment of the microfluidic gradient device, the shape of the source port perimeter is rectangular, polygonal or curvilinear, and the shape of the sink port perimeter is rectangular, polygonal or curvilinear.

In another exemplary embodiment of the microfluidic gradient device, the device is constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

In another exemplary embodiment of the microfluidic gradient device, wherein the sink assembly further comprises an air vent port, having an air vent port area in the range of 900 $\mu m^2$ to 9 $mm^2$, and where the air vent port is connected to the sink reservoir.

Another aspect of the invention is a microfluidic gradient device comprising a source assembly comprising a source port, having a source port area and source port perimeter, and comprising a source reservoir, and comprising a source input reservoir, and comprising a source auxiliary channel having an auxiliary height, auxiliary width, auxiliary length and auxiliary transverse cross-sectional area, having an auxiliary flow resistance in the range of $1\times10^{6}$ to $1\times10^{15}$ N-s-$m^{-5}$, and having an auxiliary contact angle, and where the source port is connected to the source input reservoir, and where the source auxiliary channel is in fluidic communication with the source input reservoir and the source reservoir, and where the source assembly is adapted to contain a source liquid volume in the range of 75 pL to 110 μL defining an air/liquid interface within the source port having a source port radius of curvature, a sink assembly comprising a sink port having a sink port area and sink port perimeter, and comprising a sink reservoir, and comprising a cell addition port having a cell addition port area and a cell addition port perimeter, and comprising a cell addition reservoir, where the sink port is connected to the sink reservoir, and where the cell addition port is connected to the cell addition reservoir, and where the cell addition reservoir is in fluidic communication with the sink reservoir, and the sink assembly is adapted to contain a sink liquid volume in the range of 500 pL to 100 μL defining an air/liquid interface within the sink port having a sink port radius of curvature, and defining an air/liquid interface within the cell addition port having a cell addition port radius of curvature, a gradient channel having a gradient height, gradient width, gradient length and gradient transverse cross-sectional area and having a gradient flow resistance in the range of $1\times10^{8}$ to $1\times10^{18}$ N-s-m$^{-5}$ and having a gradient contact angle and adapted to contain a gradient liquid volume in the range of 500 fL to 6 μL in fluid communication between the source and sink reservoirs, and, a closed circuit channel having a circuit height, circuit width, circuit length, and circuit transverse cross-sectional area and having a circuit flow resistance in the range of $1\times10^{6}$ to $1\times10^{15}$ N-s-m$^{-5}$ and having a circuit contact angle and adapted to contain a circuit liquid volume in the range of 50 pL to 400 μL and in fluid communication with the source and sink reservoirs, the ratio of the (gradient flow resistance):(circuit flow resistance) is in the range of (10-10,000):1.

In another exemplary embodiment of the microfluidic gradient device, the gradient height is in the range of 1 μm to 200 μm, the gradient width is in the range of 10 μm to 3 mm, the gradient length is in the range of 10 μm to 10 mm, circuit height is in the range of 10 μm to 2 mm, the circuit width is in the range of 50 μm to 4 mm, the circuit length is in the range of 100 μm to 50 mm, the auxiliary height is in the range of 10 μm to 2 mm, the auxiliary width is in the range of 10 μm to 4 mm, the auxiliary length is in the range of 10 μm to 10 mm, the gradient transverse cross-sectional area is in the range of 10 μm$^2$ to $6\times10^{5}$ μm$^2$, the circuit transverse cross-sectional area is in the range of 500 μm$^2$ to $8\times10^{6}$ μm$^2$, the auxiliary transverse cross-sectional area is in the range of 500 μm$^2$ to $8\times10^{6}$ μm$^2$, the source port area is in the range of 900 μm$^2$ to 9 mm$^2$, the sink port area is in the range of 2500 μm$^2$ to 81 mm$^2$, and the cell addition port area is in the range of 900 μm$^2$ to 9 mm$^2$.

In another exemplary embodiment of the microfluidic gradient device, useful for chemotaxis assays, wherein the gradient height is in the range of 15 μm to 200 μm, the gradient width is in the range of 100 μm to 3 mm, the gradient length is in the range of 500 μm to 4 mm, circuit height is in the range of 100 μm to 2 mm, the circuit width is in the range of 500 μm to 4 mm, wherein the circuit length is in the range of 3 mm to 30 mm, the auxiliary height is in the range of 100 μm to 2 mm, the auxiliary width is in the range of 500 μm to 4 mm, the auxiliary length is in the range of 500 μm to 5 mm, the gradient transverse cross-sectional area is in the range of 1500 μm$^2$ to $6\times10^{5}$ μm$^2$, the circuit transverse cross-sectional area is in the range of $1\times10^{5}$ μm$^2$ to $8\times10^{6}$ μm$^2$, the auxiliary transverse cross-sectional area is in the range of $5\times10^{4}$ μm$^2$ to $8\times10^{6}$ μm$^2$, the source port area is in the range of 2500 μm$^2$ to 9 mm$^2$, the sink port area is in the range of $1\times10^{4}$ μm$^2$ to 81 mm$^2$, and the cell addition port area is in the range of 2500 μm$^2$ to 9 mm$^2$.

In another exemplary embodiment of the microfluidic gradient device, the gradient height is around 40 μm, the gradient width is around 0.3 mm, the gradient length is around 1.5 mm, circuit height is around 0.25 mm, the circuit width is around 1 mm, the circuit length is around 17 mm, auxiliary height is around 250 μm, the auxiliary width is around 1 mm, the auxiliary length is around 1 mm, the gradient transverse cross-sectional area is around $1.2\times10^{4}$ μm$^2$, the circuit transverse cross-sectional area is around $2.5\times10^{5}$ μm$^2$, the auxiliary transverse cross-sectional area is around $2.5\times10^{5}$ μm$^2$, the ratio of the (gradient flow resistance):(circuit flow resistance) is around 100:1, the gradient liquid volume is around 20 nL, the circuit liquid volume is around 4 μL, the gradient flow resistance is around $1.2\times10^{12}$ N-s-m$^{-5}$, the circuit flow resistance is around $1\times10^{10}$ N-s-m$^{-5}$, the auxiliary flow resistance is around $5\times10^{9}$ N-s-m$^{-5}$, the source liquid volume is around 0.5 μL, the sink liquid volume is around 5 μL, the source input liquid volume is around 0.3 μL, the source port area is around 0.8 mm$^2$, the sink port area is around 3 mm$^2$, and, the cell addition port area is around 0.2 mm$^2$.

In another exemplary embodiment of the microfluidic gradient device, the inner surface of the gradient channel has a gradient contact angle in the range of 0° to 60°, the inner surface of the closed-circuit channel has a closed-circuit contact angle in the range of 0° to 60°, and the inner surface of the auxiliary channel has a gradient contact angle in the range of 0° to 60°.

In another exemplary embodiment of the microfluidic gradient device, the source port radius of curvature, the cell addition port radius of curvature, and the sink port radius of curvature are equal when gradient, circuit, and auxiliary liquid volumes are in flow equilibrium.

In another exemplary embodiment of the microfluidic gradient device, the transverse cross-sectional shape of the gradient channel is rectangular or curvalinear, the longitudinal cross-sectional shape of the gradient channel is rectangular or curvalinear, the transverse cross-sectional shape of the closed circuit channel is rectangular or curvalinear, the longitudinal cross-sectional shape of the closed circuit channel is rectangular or curvalinear, and the transverse cross-sectional shape of the auxiliary channel is rectangular or curvalinear, the longitudinal cross-sectional shape of the auxiliary channel is rectangular or curvalinear.

In another exemplary embodiment of the microfluidic gradient device, the shape of the source port perimeter is rectangular, polygonal or curvilinear, the shape of the cell addition port perimeter is rectangular, polygonal or curvilinear, and the shape of the sink port perimeter is rectangular, polygonal or curvilinear.

In another exemplary embodiment of the microfluidic gradient device, the device is constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

In another exemplary embodiment of the microfluidic gradient device, the sink assembly further comprises an air vent port, having an air vent port area in the range of 900 μm$^2$ to 9 mm$^2$, and where the air vent port is connected to the sink reservoir.

Another aspect of the invention is a microfluidic gradient device comprising a source assembly comprising a source port, having a source port area and source port perimeter, and comprising a source reservoir, and comprising a source input reservoir, and comprising a source auxiliary channel having an auxiliary height, auxiliary width, auxiliary length and auxiliary transverse cross-sectional area, having an auxiliary flow resistance in the range of $1\times10^{6}$ to $1\times10^{15}$ N-s-m$^{-5}$, and having an auxiliary contact angle, and where the source port is connected to the source input reservoir, and where the source auxiliary channel is in fluidic communication with the source input reservoir and the source reservoir, and where the source assembly is adapted to contain a source liquid volume in the range of 75 pL to 110 μL defining an air/liquid interface within the source port having a source port radius of curvature, a sink assembly comprising a sink port, having a sink port area and a sink port perimeter, and a sink reservoir, where the sink port is connected to the sink reservoir, and the sink assembly is adapted to contain a sink liquid volume in the range of 500 pL to 100 μL defining an air/liquid interface within the sink port having a sink port radius of curvature, a gradient assembly comprising a gradient channel having a gradient height, gradient width, gradient length and gradient transverse cross-sectional area and having a gradient flow resistance in the range of $1\times10^{8}$ to $1\times10^{18}$ N-s-m$^{-5}$ and having a gradient contact angle, and comprising a cell addition port having a cell addition port area and cell addition port perimeter, and comprising a cell addition reservoir, where the cell addition port is connected to the cell addition reservoir and where the cell addition reservoir is in fluidic communication with the gradient channel, and where the gradient assembly is adapted to contain a gradient liquid volume in the range of 25 pL to 1 μL, defining an air/liquid interface within the cell addition port, having a cell addition port radius of curvature, and where the gradient liquid volume is in fluid communication between the source and sink reservoirs, and, a closed circuit channel having a circuit height, circuit width, circuit length, and circuit transverse cross-sectional area and having a circuit flow resistance in the range of $1\times10^{6}$ to $1\times10^{15}$ N-s-m$^{-5}$ and having a circuit contact angle and adapted to contain a circuit liquid volume in the range of 50 pL to 400 μL and in fluid communication with the source and sink reservoirs, and the ratio of the (gradient flow resistance):(circuit flow resistance) is in the range of (10-10,000):1.

In another exemplary embodiment of the microfluidic gradient device, the gradient height is in the range of 1 μm to 200 μm, the gradient width is in the range of 10 μm to 3 mm, the gradient length is in the range of 10 μm to 10 mm, circuit height is in the range of 10 μm to 2 mm, the circuit width is in the range of 50 μm to 4 mm, the circuit length is in the range of 100 μm to 50 mm, the auxiliary height is in the range of 10 μm to 2 mm, the auxiliary width is in the range of 50 μm to 4 mm, the auxiliary length is in the range of 10 μm to 10 mm, the gradient transverse cross-sectional area is in the range of 10 μm$^2$ to $6\times10^{5}$ μm$^2$, the circuit transverse cross-sectional area is in the range of 500 μm$^2$ to $8\times10^{6}$ μm$^2$, the auxiliary transverse cross-sectional area is in the range of 500 μm$^2$ to $8\times10^{6}$ μm$^2$, the source port area is in the range of 900 μm$^2$ to 9 mm$^2$, the sink port area is in the range of 2500 μm$^2$ to 81 mm$^2$, and the cell addition port area is in the range of 900 μm$^2$ to 9 mm$^2$.

In another exemplary embodiment of the microfluidic gradient device, useful for chemotaxis assays, the gradient height is in the range of 15 μm to 200 μm, the gradient width is in the range of 100 μm to 3 mm, the gradient length is in the range of 500 μm to 4 mm, circuit height is in the range of 100 μm to 2 mm, wherein the circuit width is in the range of 500 μm to 4 mm, wherein the circuit length is in the range of 3 mm to 30 mm, the auxiliary height is in the range of 100 μm to 2 mm, the auxiliary width is in the range of 500 μm to 4 mm, the auxiliary length is in the range of 500 μm to 5 mm, the gradient transverse cross-sectional area is in the range of 1500 μm$^2$ to $6\times10^{5}$ μm$^2$, the circuit transverse cross-sectional area is in the range of $1\times10^{5}$ μm$^2$ to $8\times10^{6}$ μm$^2$, the auxiliary transverse cross-sectional area is in the range of $5\times10^{4}$ μm$^2$ to $8\times10^{6}$ μm$^2$, the source port area is in the range of 2500 μm$^2$ to 9 mm$^2$, the sink port area is in the range of $1\times10^{4}$ μm$^2$ to 81 mm$^2$, and the cell addition port area is in the range of 2500 μm$^2$ to 9 mm$^2$.

In another exemplary embodiment of the microfluidic gradient device, the gradient height is around 50 μm, the gradient width is around 0.3 mm, the gradient length is around 3 mm, circuit height is around 0.4 mm, the circuit width is around 1 mm, the circuit length is around 15 mm, wherein auxiliary height is around 400 μm, the auxiliary width is around 1 mm, wherein the auxiliary length is around 0.6 mm, the gradient transverse cross-sectional area is around $1.5\times10^{4}$ μm$^2$, the circuit transverse cross-sectional area is around $4\times10^{5}$ μm$^2$, the auxiliary transverse cross-sectional area is around $4\times10^{5}$ μm$^2$, the ratio of the (gradient flow resistance):(circuit flow resistance) is around 300:1, the gradient liquid volume is around 45 nL, the circuit liquid volume is around 6 μL, the auxiliary liquid volume is around 240 nL, the gradient flow resistance is around $9\times10^{11}$ N-s-m$^{-5}$, the circuit flow resistance is around $3\times10^{9}$ N-s-m$^{-5}$, the auxiliary flow resistance is around $7\times10^{7}$ N-s-m$^{-5}$, the source liquid volume is around 0.5 μL, the sink liquid volume is around 6 μL, the source input liquid volume is around 0.4 μL, the source port area is around 0.8 mm$^2$, the sink port area is around 5 mm$^2$ and, the cell addition port area is around 0.8 mm$^2$.

In another exemplary embodiment of the microfluidic gradient device, the inner surface of the gradient channel has a gradient contact angle in the range of 0° to 60°, the inner surface of the closed-circuit channel has a closed-circuit contact angle in the range of 0° to 60°, and the inner surface of the auxiliary channel has a gradient contact angle in the range of 0° to 60°.

In another exemplary embodiment of the microfluidic gradient device, the source port radius of curvature, the cell addition port radius of curvature and the sink port radius of curvature are equal when gradient and circuit, and auxiliary liquid volumes are in flow equilibrium.

In another exemplary embodiment of the microfluidic gradient device, the transverse cross-sectional shape of the gradient channel is rectangular or curvalinear, the longitudinal cross-sectional shape of the gradient channel is rectangular or curvalinear, the transverse cross-sectional shape of the closed circuit channel is rectangular or curvalinear, the longitudinal cross-sectional shape of the closed circuit channel is rectangular or curvalinear, and the transverse cross-sectional shape of the auxiliary channel is rectangular or curvalinear, the longitudinal cross-sectional shape of the auxiliary channel is rectangular or curvalinear.

In another exemplary embodiment of the microfluidic gradient device, the shape of the source port perimeter is rectangular, polygonal or curvilinear, the shape of the cell addition port perimeter is rectangular, polygonal or curvilinear, and the shape of the sink port perimeter is rectangular, polygonal or curvilinear.

In another exemplary embodiment of the microfluidic gradient device, the device is constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

In another exemplary embodiment of the microfluidic gradient device, the sink assembly further comprises an air vent port, having an air vent port area in the range of 900 μm$^2$ to 9 mm$^2$, and where the air vent port is connected to the sink reservoir.

Another aspect of the invention is a microfluidic gradient device comprising a source assembly comprising a source port, having a source port area and source port perimeter, and comprising a source reservoir, and comprising a source input reservoir, and comprising a source auxiliary channel having an auxiliary height, auxiliary width, auxiliary length and auxiliary transverse cross-sectional area, having an auxiliary flow resistance in the range of $1\times10^{6}$ to $1\times10^{15}$ N-s-m$^{-5}$, and having an auxiliary contact angle, and where the source port is connected to the source input reservoir, and where the source auxiliary channel is in fluidic communication with the source input reservoir and the source reservoir, and where the source assembly is adapted to contain a source liquid volume in the range of 75 pL to 110 μL defining an air/liquid interface within the source port having a source port radius of curvature, a sink assembly comprising a sink port, having a sink port area and a sink port perimeter, and comprising a sink reservoir, where the sink port is connected to the sink reservoir, and the sink assembly is adapted to contain a sink liquid volume in the range of 500 pL to 100 μL defining an air/liquid interface within the sink port having a sink port radius of curvature, a gradient channel having a gradient height, gradient width, gradient length and gradient transverse cross-sectional area and having a gradient flow resistance in the range of $1\times10^{8}$ to $1\times10^{18}$ N-s-m$^{-5}$ and having a gradient contact angle and adapted to contain a gradient liquid volume in the range of 500 fL, to 6 μL in fluid communication between the source and sink reservoirs, and, a closed circuit channel having a circuit height, circuit width, circuit length, and circuit transverse cross-sectional area and having a circuit flow resistance in the range of $1\times10^{6}$ to $1\times10^{15}$ N-s-m$^{-5}$ and having a circuit contact angle and adapted to contain a circuit liquid volume in the range of 50 pL to 400 μL and in fluid communication with the source and sink reservoirs, a cell seeding assembly comprising a cell addition port, having a cell addition port area and a cell addition port perimeter, and comprising a cell addition reservoir, and comprising a cell addition channel having a cell addition height, cell addition width, cell addition length and cell addition transverse cross-sectional area, and having a cell addition flow resistance in the range of $5\times10^{6}$ to $6\times10^{13}$ N-s-m$^{-5}$, where the cell addition port is connected to the cell addition reservoir, and where the cell addition assembly is adapted to contain a cell addition liquid volume in the range of 30 pL to 65 μL defining an air/liquid interface within the cell addition port having a cell addition port radius of curvature, the ratio of the (gradient flow resistance):(circuit flow resistance) is in the range of (10-10,000):1.

In another exemplary embodiment of the microfluidic gradient device, the gradient height is in the range of 1 μm to 200 μm, the gradient width is in the range of 10 μm to 3 mm, the gradient length is in the range of 50 μm to 10 mm, circuit height is in the range of 10 μm to 2 mm, the circuit width is in the range of 50 μm to 4 mm, the circuit length is in the range of 100 μm to 50 mm, the auxiliary height is in the range of 10 μm to 2 mm, the auxiliary width is in the range of 50 μm to 4 mm, the auxiliary length is in the range of 50 μm to 10 mm, the cell addition height is in the range of 10 μm to 2 mm, the cell addition width is in the range of 10 μm to 3 mm, the cell addition length is in the range of 50 μm to 10 mm, the gradient transverse cross-sectional area is in the range of 10 μm$^2$ to $6\times10^{5}$ μm$^2$, the circuit transverse cross-sectional area is in the range of 500 μm$^2$ to $8\times10^{6}$ μm$^2$, the auxiliary transverse cross-sectional area is in the range of 500 μm$^2$ to $8\times10^{6}$ μm$^2$, the cell addition transverse cross-sectional area is in the range of 100 μm$^2$ to $6\times10^{6}$ μm$^2$, the source port area is in the range of 900 μm$^2$ to 9 mm$^2$, the sink port area is in the range of 2500 μm$^2$ to 81 mm$^2$, and the cell addition port area is in the range of 900 μm$^2$ to 9 mm$^2$.

In another exemplary embodiment of the microfluidic gradient device, useful for chemotaxis assays, the gradient height is in the range of 15 μm to 200 μm, the gradient width is in the range of 100 μm to 3 mm, the gradient length is in the range of 500 μm to 4 mm, circuit height is in the range of 100 μm to 2 mm, the circuit width is in the range of 500 μm to 4 mm, the circuit length is in the range of 3 mm to 30 mm, the auxiliary height is in the range of 100 μm to 2 mm, the auxiliary width is in the range of 500 μm to 4 mm, the auxiliary length is in the range of 500 μm to 5 mm, the cell addition height is in the range of 100 μm to 2 mm, the cell addition width is in the range of 100 μm to 3 mm, the cell addition length is in the range of 500 μm to 4 mm, the gradient transverse cross-sectional area is in the range of 1500 μm$^2$ to $6\times10^{5}$ μm$^2$, the circuit transverse cross-sectional area is in the range of $1\times10^{5}$ μm$^2$ to $8\times10^{6}$ μm$^2$, the auxiliary transverse cross-sectional area is in the range of $5\times10^{4}$ μm$^2$ to $8\times10^{6}$ μm$^2$, the cell addition transverse cross-sectional area is in the range of $2\times10^{4}$ μm$^2$ to $6\times10^{6}$ μm$^2$, the source port area is in the range of 2500 μm$^2$ to 9 mm$^2$, the sink port area is in the range of $1\times10^{4}$ μm$^2$ to 81 mm$^2$, and the cell addition port area is in the range of 2500 μm$^2$ to 9 mm$^2$.

In another exemplary embodiment of the microfluidic gradient device, the gradient height is around 50 μm, the gradient width is around 0.3 mm, the gradient length is around 3 mm, circuit height is around 0.4 mm, wherein the circuit width is around 1 mm, the circuit length is around 15 mm, auxiliary height is around 400 μm, the auxiliary width is around 1 mm, the auxiliary length is around 0.6 mm, cell addition height is around 0.4 mm, the cell addition width is around 1 mm, wherein the cell addition length is around 1.5 mm, the gradient transverse cross-sectional area is around $1.5\times10^{4}$ μm$^2$, the circuit transverse cross-sectional area is around 4×10 μm$^2$, the auxiliary transverse cross-sectional area is around $4\times10^{5}$ μm$^2$, the cell addition transverse cross-sectional area is around $4\times10^{5}$ μm$^2$, the ratio of the (gradient flow resistance):(circuit flow resistance) is around 300:1, the gradient liquid volume is around 45 nL, wherein the circuit liquid volume is around 6 μL, the auxiliary liquid volume is around 240 nL, the gradient flow resistance is around $9\times10^{11}$ N-s-m$^{-5}$, the circuit flow resistance is around $3\times10^{9}$ N-s-m$^{-5}$, the auxiliary flow resistance is around $7\times10^{7}$ N-s-m$^{-5}$, the cell addition flow resistance is around $3\times10^{8}$ N-s-m$^{-5}$, the source liquid volume is around 1 μL, the sink liquid volume is around 6 μL, the source input liquid volume is around 0.4 μL, the cell addition liquid volume is around 1 μL, the source port area is around 0.8 mm$^2$, the sink port area is around 5 mm$^2$, and the cell addition port area is around 0.8 mm$^2$.

In another exemplary embodiment of the microfluidic gradient device, the inner surface of the gradient channel has a gradient contact angle in the range of 0° to 60°, the inner surface of the closed-circuit channel has a closed-circuit contact angle in the range of 0° to 60°, the inner surface of the cell addition channel has a cell addition contact angle in the range of 0° to 60°, and the inner surface of the auxiliary channel has a gradient contact angle in the range of 0° to 60°.

In another exemplary embodiment of the microfluidic gradient device, the source port radius of curvature, cell addition port radius of curvature, and the sink port radius of curvature are equal when gradient, circuit, auxiliary and cell addition liquid volumes are in flow equilibrium.

In another exemplary embodiment of the microfluidic gradient device, the transverse cross-sectional shape of the gradient channel is rectangular or curvalinear, the longitudinal cross-sectional shape of the gradient channel is rectangular or curvalinear, the transverse cross-sectional shape of the closed circuit channel is rectangular or curvalinear, the longitudinal cross-sectional shape of the closed circuit channel is rectangular or curvalinear, the transverse cross-sectional shape of the cell addition channel is rectangular or curvalinear, the longitudinal cross-sectional shape of the cell addition channel is rectangular or curvalinear, and the transverse cross-sectional shape of the auxiliary channel is rectangular or curvalinear, the longitudinal cross-sectional shape of the auxiliary channel is rectangular or curvalinear.

In another exemplary embodiment of the microfluidic gradient device, the shape of the source port perimeter is rectangular, polygonal or curvilinear, wherein the shape of the sink port perimeter is rectangular, polygonal or curvilinear, and wherein the shape of the cell addition port perimeter is rectangular, polygonal or curvilinear.

In another exemplary embodiment of the microfluidic gradient device, the device is constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

In another exemplary embodiment of the microfluidic gradient device, the sink assembly further comprises an air vent port, having an air vent port area in the range of 900 $\mu m^2$ to 9 $mm^2$, and where the air vent port is connected to the sink reservoir.

Another aspect of the invention is a method of using any one of the microfluidic gradient devices in any order or combination; providing a volume of source liquid in the source assembly, a volume of sink liquid in the sink assembly, a volume of gradient liquid in the gradient channel, a volume of circuit liquid in the closed circuit channel, the gradient and circuit liquid volumes are in flow equilibrium, and, the source port radius of curvature and the sink port radius of curvature are equal.

Another aspect of the invention is a method of using any one of the microfluidic gradient devices in any order or combination; providing a volume of source liquid in the source assembly, a volume of sink liquid in the sink assembly, a volume of gradient liquid in the gradient channel, a volume of circuit liquid in the closed circuit channel, the gradient and circuit liquid volumes are in flow equilibrium, and, the source port radius of curvature, the sink port radius of curvature, and the cell addition port radius of curvature are equal.

Another aspect of the invention is a method of using any one of the microfluidic gradient devices in any order or combination; providing a volume of source liquid in the source assembly, a volume of sink liquid in the sink assembly, a volume of gradient liquid in the gradient assembly, a volume of circuit liquid in the closed circuit channel, the gradient and circuit liquid volumes are in flow equilibrium, and, the source port radius of curvature, the sink port radius of curvature, and the cell addition port radius of curvature are equal.

Another aspect of the invention is a method of using any one of the microfluidic gradient devices in any order or combination; providing a volume of source liquid in the source assembly, a volume of sink liquid in the sink assembly, a volume of cell addition liquid in the cell addition assembly, a volume of gradient liquid in the gradient channel, a volume of circuit liquid in the closed circuit channel, the gradient, circuit and cell addition liquid volumes are in flow equilibrium, and, the source port radius of curvature, the sink port radius of curvature and cell addition port radius of curvature are equal.

Another aspect of the invention is a method of using any one of the microfluidic gradient device in any order or combination; providing a volume of source liquid in the source assembly, a volume of sink liquid in the sink assembly, a volume of gradient liquid in the gradient channel, a volume of circuit liquid in the closed circuit channel, the gradient and circuit liquid volumes are in flow equilibrium, and, the source port radius of curvature and the sink port radius of curvature are equal.

Another aspect of the invention is a method of using any one of the microfluidic gradient devices in any order or combination; providing a volume of source liquid in the source assembly, a volume of sink liquid in the sink assembly, a volume of gradient liquid in the gradient channel, a volume of circuit liquid in the closed circuit channel, the gradient, circuit, and auxiliary liquid volumes are in flow equilibrium, and, the source port radius of curvature, the sink port radius of curvature, and the cell addition port radius of curvature are equal.

Another aspect of the invention is a method of using any one of the microfluidic gradient devices in any order or combination; providing a volume of source liquid in the source assembly, a volume of sink liquid in the sink assembly, a volume of cell addition liquid in the cell addition assembly, a volume of gradient liquid in the gradient channel, a volume of circuit liquid in the closed circuit channel, the gradient, circuit, auxiliary and cell addition liquid volumes are in flow equilibrium, and, the source port radius of curvature, the sink port radius of curvature and cell addition port radius of curvature are equal.

In another exemplary embodiment of any of the methods herein, the liquids comprise phosphate buffered saline.

In another exemplary embodiment of any of the methods herein, one or more of the liquids further comprise a fluorescent dye.

In another exemplary embodiment of any of the methods herein, the concentration of fluorescent dye is around 0.1 mg/mL.

In another exemplary embodiment of any of the methods herein, the liquids comprise cell culture media.

In another exemplary embodiment of any of the methods herein, the cell culture media is DMEM, or EGM2MV.

In another exemplary embodiment of any of the methods herein, the cell culture media further contains fetal bovine serum, or fetal calf serum.

In another exemplary embodiment of any of the methods herein, the volume of the sink liquid, gradient liquid and/or cell addition liquid further comprises cells.

In another exemplary embodiment of any of the methods herein, the cells comprise primary cells or cell lines possessing the characteristics of granulocytes, mononuclear leukocytes, or human neutrophils.

In another exemplary embodiment of any of the methods herein, the cells comprise primary neutrophils, or primary eosinophils, or primary basophils, or primary lymphocytes, or primary monocytes, or primary macrophages.

In another exemplary embodiment of any of the methods herein, the cells comprise primary cancer cells, or cancer cell line cells.

In another exemplary embodiment of any of the methods herein, the cells comprise primary vascular endothelial cells or endothelial cell-derived cell line cells.

In another exemplary embodiment of any of the methods herein, the cells comprise non-adherent, motile cells.

In another exemplary embodiment of any of the methods herein, the cells comprise bacteria, or sperm cells.

In another exemplary embodiment of any of the methods herein, the cells comprise primary neuronal cells.

In another exemplary embodiment of any of the methods herein, the volume of the sink liquid, gradient liquid and/or cell addition liquid further comprises beads containing biomolecules.

In another exemplary embodiment of any of the methods herein, the volume of the source liquid further comprises a bioactive substance.

In another exemplary embodiment of any of the methods herein, the bioactive substance is a chemoattractant or chemokine.

In another exemplary embodiment of any of the methods herein, the chemoattractant is Interleukin-8, or formyl-methionine-leucine-phenylalanine.

In another exemplary embodiment of any of the methods herein, the bioactive substance is an amino acids or a combination of two or more amino acids.

In another exemplary embodiment of any of the methods herein, the bioactive substance is epidermal growth factor, or transforming growth factor-beta, or ephrin.

In another exemplary embodiment of any of the methods herein, the radius of curvature at equilibrium is in the range of 0.01 mm to infinity, or −0.01 to negative infinity.

In another exemplary embodiment of any of the methods herein, one or more of the liquids is provided by wick-filling.

In another exemplary embodiment of any of the methods herein, one or more of the liquids is provided by pipetting to the source port, sink port or cell addition port and subsequent equilibration of fluid volumes.

In another exemplary embodiment of any of the methods herein, the provision of all volumes together with an assay medium fluid, and comprising, in any order, the following; partially replacing the volume of the source assembly with a second fluid comprising chemoattractant medium, partially replacing the volume of the sink assembly, gradient assembly or cell addition assembly with a third fluid containing a cell suspension.

In another exemplary embodiment of any of the methods herein, the provision of all volumes together with an assay medium fluid, and comprising, in any order, the following; partially replacing the volume of the source assembly with a second fluid comprising chemoattractant medium, partially replacing the volume of the sink assembly, gradient assembly or cell addition assembly with a third fluid containing a cell suspension, and partially replacing the volume of the source assembly, sink assembly, gradient assembly, cell addition assembly, gradient channel and/or closed-circuit channel with a fourth fluid containing a readout reagent.

In another exemplary embodiment of any of the methods herein, one or more of the steps is repeated one or more times.

In another exemplary embodiment of any of the methods herein, the assay medium further comprises a bio-active compound or drug.

In another exemplary embodiment of any of the methods herein, the readout reagent is an antibody, fluorophore-conjugated antibody, an enzyme-conjugated antibody, a histological staining reagent, an immuno-cytochemical staining reagent or an enzyme substrate.

One aspect of the invention includes a microfluidic gradient device having a source assembly adapted to contain a source liquid volume in the range of 25 pL to 15 μL defining a source assembly air/liquid interface having a source assembly radius of curvature comprising a source port having a source port area and source port perimeter in fluid communication with a source reservoir, a sink assembly adapted to contain a sink liquid volume in the range of 500 pL to 100 μL defining a sink assembly air/liquid interface having a sink assembly radius of curvature comprising a sink port having a sink port area and a sink port perimeter in fluid communication with a sink reservoir, a gradient channel adapted to contain a gradient fluid volume in the range of 500 fL, to 6 μL, the gradient channel having a gradient height, gradient width, gradient length, gradient transverse cross-sectional area, gradient flow resistance in the range of $1\times10^{8}$ to $1\times10^{18}$ N-s-m$^{-5}$, and, gradient contact angle, the gradient channel in fluid communication with the source reservoir and sink reservoir, and, a closed circuit channel adapted to contain a circuit liquid volume in the range of 50 pL to 400 μL, the closed circuit channel having a circuit height, circuit width, circuit length, circuit transverse cross-sectional area, circuit flow resistance in the range of $1\times10^{6}$ to $1\times10^{15}$ N-s-m$^{-5}$, and, circuit contact angle, the closed circuit channel in fluid communication with the source reservoir and sink reservoir, wherein the ratio (gradient flow resistance):(circuit flow resistance) is in the range of (10-10,000):1.

Another aspect of the invention includes a microfluidic gradient device having a source assembly adapted to contain a source liquid volume in the range of 25 pL to 15 μL defining a source assembly air/liquid interface having a source assembly radius of curvature comprising a source port having a source port area and source port perimeter in fluid communication with a source reservoir, a sink assembly adapted to contain a sink liquid volume in the range of 500 pL to 100 μL defining a sink assembly air/liquid interface having a sink assembly radius of curvature comprising a sink port having a sink port area and sink port perimeter in fluid communication with a sink reservoir, a cell addition assembly adapted to contain a cell addition assembly liquid volume defining a cell addition assembly air/liquid interface having a cell addition assembly radius of curvature comprising a cell addition port having a cell addition port area and a cell addition port perimeter in fluid communication with a cell addition reservoir, the cell addition reservoir in fluid communication with the sink reservoir, a gradient channel adapted to contain a gradient liquid volume in the range of 500 fL to 6 μL having a gradient height, gradient width, gradient length, gradient transverse cross-sectional area, gradient flow resistance in the range of $1\times10^{8}$ to $1\times10^{18}$ N-s-m$^{-5}$, and, gradient contact angle, the gradient channel in fluid communication with the source reservoir and sink reservoir, and, a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-m$^{-5}$, and, circuit contact angle, the closed circuit channel in fluid communication with the source reservoir and sink reservoir, wherein the ratio (gradient flow resistance):(circuit flow resistance) is in the range of (10-10,000):1.

Another aspect of the invention includes a microfluidic gradient device having a source assembly adapted to contain a source liquid volume in the range of 25 pL to 15 μL defining a source assembly air/liquid interface having a source assembly radius of curvature comprising a source port having a source port area and source port perimeter in fluid communication with a source reservoir, a sink assembly adapted to contain a sink liquid volume in the range of 500 pL to 100 μL defining a sink assembly air/liquid interface having a sink assembly radius of curvature comprising a sink port having a sink port area and sink port perimeter in fluid communication with a sink reservoir, a gradient channel adapted to contain a gradient liquid volume in the range of 25 pL to 6 μL having a gradient height, gradient width, gradient length, gradient transverse cross-sectional area, gradient flow resistance in the range of $1\times10^{8}$ to $1\times10^{18}$ N-s-m$^{-5}$, and, gradient contact angle, the gradient channel in fluid communication with the source reservoir and sink reservoir, a cell addition assembly adapted to contain a cell addition assembly liquid volume defining a cell addition assembly air/liquid interface having a cell addition assembly radius of curvature comprising a cell addition port having a cell addition port area and a cell addition port perimeter in fluid communication with a cell addition reservoir, the cell addition reservoir in fluid communication with the gradient channel, and, a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-m$^{-5}$, and, circuit contact angle, the closed circuit channel in fluid communication with the source reservoir and sink reservoir, wherein the ratio (gradient flow resistance):(circuit flow resistance) is in the range of (10-10,000):1.

Another aspect of the invention includes a microfluidic gradient device having a source assembly adapted to contain a source liquid volume in the range of 25 pL to 15 μL defining a source assembly air/liquid interface having a source assembly radius of curvature comprising a source port having a source port area and source port perimeter in fluid communication with a source reservoir, a sink assembly adapted to contain a sink liquid volume in the range of 500 pL to 100 μL defining a sink assembly air/liquid interface having a sink assembly radius of curvature comprising a sink port having a sink port area and sink port perimeter in fluid communication with a sink reservoir, a gradient channel adapted to contain a gradient liquid volume in the range of 500 fL to 6 μL having a gradient height, gradient width, gradient length, gradient transverse cross-sectional area, gradient flow resistance in the range of $1\times10^{8}$ to $1\times10^{18}$ N-s-$m^{-5}$, and, gradient contact angle, the gradient channel in fluid communication with the source reservoir and sink reservoir, a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-$m^{-5}$, and, circuit contact angle, the closed circuit channel in fluid communication with the source reservoir and sink reservoir, and, a cell seeding assembly adapted to contain a cell seeding assembly liquid volume in the range of 30 pL to 65 μL defining a cell seeding assembly air/liquid interface having a cell seeding assembly radius of curvature comprising a cell addition port having a cell addition port area and a cell addition port perimeter in fluid communication with a cell addition reservoir in fluid communication with a cell addition channel in fluid communication with the gradient channel having a cell addition height, cell addition width, cell addition length, cell addition transverse cross-sectional area, and, cell addition flow resistance in the range of $5\times10^{6}$ to $6\times10^{13}$ N-s-$m^{-5}$, wherein the ratio (gradient flow resistance):(circuit flow resistance) is in the range of (10-10,000):1.

Another aspect of the invention includes a microfluidic gradient device having a source assembly adapted to contain a source liquid volume in the range of 75 pL to 110 μL defining a source assembly air/liquid interface having a source assembly radius of curvature comprising a source port having a source port area and source port perimeter in fluid communication with a source input reservoir, and, a source auxiliary channel in fluid communication with the source input reservoir and a source reservoir having an auxiliary height, auxiliary width, auxiliary length, auxiliary transverse cross-sectional area, auxiliary flow resistance in the range of $1\times10^{6}$ to $1\times10^{15}$ N-s-$m^{-5}$, and, auxiliary contact angle, a sink assembly adapted to contain a sink liquid volume in the range of 500 pL to 100 μL defining a sink assembly air/liquid interface having a sink assembly radius of curvature comprising a sink port having a sink port area and sink port perimeter in fluid communication with a sink reservoir, a gradient channel adapted to contain a gradient liquid volume in the range of 500 fL to 6 μL having a gradient height, gradient width, gradient length, gradient transverse cross-sectional area, gradient flow resistance in the range of $1\times10^{8}$ to $1\times10^{18}$ N-s-$m^{-5}$, and, gradient contact angle, the gradient channel in fluid communication with the source reservoir and sink reservoir, and, a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-$m^{-5}$, and, circuit contact angle, the closed circuit channel in fluid communication with the source reservoir and sink reservoir, wherein the ratio (gradient flow resistance):(circuit flow resistance) is in the range of (10-10,000):1.

Another aspect of the invention includes a microfluidic gradient device having a source assembly adapted to contain a source liquid volume in the range of 75 pL to 110 μL defining a source assembly air/liquid interface having a source assembly radius of curvature comprising: a source port having a source port area and source port perimeter in fluid communication with a source input reservoir, and, a source auxiliary channel in fluid communication with the source input reservoir and a source reservoir having an auxiliary height, auxiliary width, auxiliary length, auxiliary transverse cross-sectional area, auxiliary flow resistance in the range of $1\times10^{6}$ to $1\times10^{15}$ N-s-$m^{-5}$, and, auxiliary contact angle, a sink assembly adapted to contain a sink liquid volume in the range of 500 pL to 100 μL defining a sink assembly air/liquid interface having a sink assembly radius of curvature comprising a sink port having a sink port area and a sink port perimeter in fluid communication with a sink reservoir, a cell addition assembly adapted to contain a cell addition assembly fluid defining a cell addition assembly air/liquid interface having a cell addition assembly radius of curvature comprising a cell addition port having a cell addition port area and a cell addition port perimeter in fluid communication with a cell addition reservoir in fluid communication with the sink reservoir, a gradient channel adapted to contain a gradient liquid volume in the range of 500 fL to 6 μL having a gradient height, gradient width, gradient length, gradient transverse cross-sectional area, gradient flow resistance in the range of $1\times10^{8}$ to $1\times10^{18}$ N-s-$m^{-5}$, and, gradient contact angle, the gradient channel in fluid communication with the source reservoir and sink reservoir, and, a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-$m^{-5}$, and, circuit contact angle, the closed circuit channel in fluid communication with the source reservoir and sink reservoir, wherein the ratio (gradient flow resistance):(circuit flow resistance) is in the range of (10-10,000):1.

Another aspect of the invention includes a microfluidic gradient device having a source assembly adapted to contain a source liquid volume in the range of 75 pL to 110 μL defining a source assembly air/liquid interface having a source assembly radius of curvature comprising: a source port having a source port area and source port perimeter in fluid communication with a source input reservoir, and, a source auxiliary channel in fluid communication with the source input reservoir and a source reservoir having an auxiliary height, auxiliary width, auxiliary length, auxiliary transverse cross-sectional area, auxiliary flow resistance in the range of $1\times10^{6}$ to $1\times10^{15}$ N-s-$m^{-5}$, and, auxiliary contact angle, a sink assembly adapted to contain a sink liquid volume in the range of 500 pL to 100 μL defining a sink assembly air/liquid interface having a sink assembly radius of curvature comprising a sink port having a sink port area and a sink port perimeter in fluid communication with a sink reservoir, a gradient assembly adapted to contain a gradient assembly liquid volume in the range of 25 pL to 11 μL defining a gradient assembly air/liquid interface comprising: a cell addition port having a cell addition port area and cell addition port perimeter in fluid communication with a cell addition reservoir, a gradient channel adapted to contain a gradient channel liquid volume in fluid communication with the cell addition reservoir, source reservoir and sink reservoir having a gradient height, gradient width, gradient length, gradient transverse cross-sectional area, gradient flow resistance in the range of $1\times10^{8}$ to $1\times10^{8}$ N-s-m$^{-5}$, and gradient contact angle, and, a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-m$^{-5}$, and, circuit contact angle, the closed circuit channel in fluid communication with the source reservoir and sink reservoir, wherein the ratio of the (gradient flow resistance):(circuit flow resistance) is in the range of (10-10,000):1.

Yet another aspect of the invention includes a microfluidic gradient device having: a source assembly adapted to contain a source liquid volume in the range of 75 pL to 110 μL defining a source assembly air/liquid interface having a source assembly radius of curvature comprising: a source port having a source port area and source port perimeter in fluid communication with a source input reservoir, and, a source auxiliary channel in fluid communication with the source input reservoir and a source reservoir having an auxiliary height, auxiliary width, auxiliary length, auxiliary transverse cross-sectional area, auxiliary flow resistance in the range of $1\times10^{6}$ to $1\times10^{15}$ N-s-m$^{-5}$, and, auxiliary contact angle, a sink assembly adapted to contain a sink liquid volume in the range of 500 pL to 100 μL defining a sink assembly air/liquid interface having a sink assembly radius of curvature comprising a sink port having a sink port area and a sink port perimeter in fluid communication with a sink reservoir, a gradient channel adapted to contain a gradient channel liquid volume in the range of 500 fL to 6 μL in fluid communication with the source reservoir and sink reservoir having a gradient height, gradient width, gradient length, gradient transverse cross-sectional area, gradient flow resistance in the range of $1\times10^{8}$ to $1\times10^{18}$ N-s-m$^{-5}$, and gradient contact angle, a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-m$^{-5}$, and, circuit contact angle, the closed circuit channel in fluid communication with the source reservoir and sink reservoir, a cell seeding assembly adapted to contain a cell seeding assembly liquid volume in the range of 30 pL to 65 μL defining a cell seeding assembly air/liquid interface having a cell seeding assembly radius of curvature comprising: a cell addition port having a cell addition port area and a cell addition port perimeter in fluid communication with a cell addition reservoir in fluid communication with a cell addition reservoir, and, a cell addition channel in fluid communication with the gradient channel having a cell addition height, cell addition width, cell addition length, cell addition transverse cross-sectional area, and, cell addition flow resistance in the range of $5\times10^{6}$ to $6\times10^{13}$ N-s-m$^{-5}$, wherein the ratio of the (gradient flow resistance):(circuit flow resistance) is in the range of (10-10,000):1.

Other objects, advantages and features of the present invention will become apparent from the following specifications taken in conjunction with accompanying drawings.

DETAILED DESCRIPTION OF THE INVENTION

Figure 1:
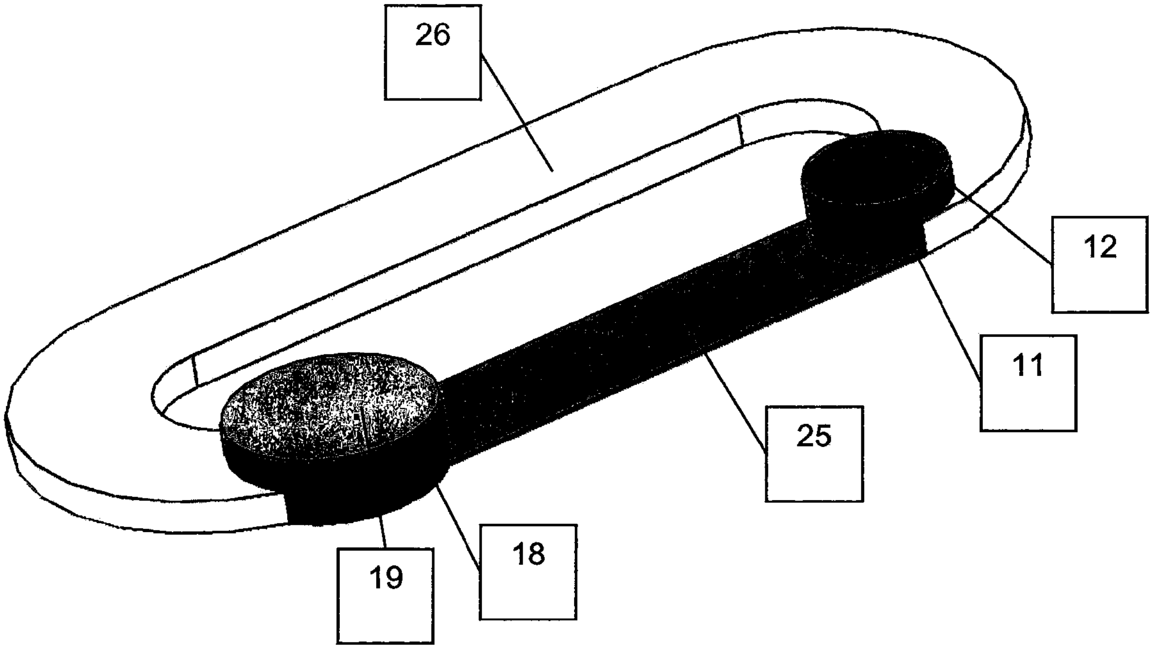
FIG. 1 is a perspective view of one embodiment of the microfluidic gradient device of the present invention, whereby the flow resistance of the gradient channel is approximately 300× higher than the flow resistance of the closed circuit channel.

The present invention is broadly summarized as a novel and non-obvious device and method providing a stable, static fluid gradient on a microfluidic scale, which is suitable for testing and analyzing chemotaxis.

One aspect of the invention is a microfluidic method and device for testing and analyzing chemotaxis by providing a stable, static fluid gradient. The device includes a sink reservoir for receiving biological cellular material and a source reservoir for receiving a chemoattractant. The biological cellular material migrates through a low fluid volume microfluidic gradient channel located between the source and sink reservoirs.

The fluid in the gradient channel is static and stable, due to a high fluid volume closed circuit bypass microfluidic channel also in fluid communication with the source and sink reservoirs, whereby the bypass channel relieves any pressure differential imparted across the gradient channel. Microfluidic passive pumping is disclosed in U.S. Pat. No. 7,189,580, which is hereby incorporated herein by reference in its entirety.

Another aspect of the invention is a microfluidic method and device for testing and analyzing molecular interactions in the presence of a stable, static gradient of an agonistic or antagonistic substance. The device includes a gradient channel for receiving readout molecules as a surface coating, or as a coating on small beads (1-20 μm diameter) and assay molecules in solution. The device also includes a source reservoir to receive the agonistic or antagonistic substance. The substance forms a gradient across the length of the gradient channel located between the source and sink reservoirs. The gradient allows a continuous readout of concentrations across the span of the gradient. The assay molecules may be an enzyme and suitable substrate. The readout molecules may be an antibody that can bind the product of the enzyme-substrate reaction. The density of bound product can be detected by conventional sandwich immunosorbent assay, which involves introducing a secondary antibody having a fluorophore or a chromogenic enzyme attached to the antibody.

Migration is a cellular action which is involved in many physiological and pathophysiological processes. For example, during wound healing, platelets and immune cells release soluble factors known as chemokines that diffuse to the nearest blood vessel forming a gradient. Upon sensing this signal, leukocytes enter the wounded tissue from the blood stream and move toward increasing concentration of the chemokine gradient. Such leukocyte behavior is referred to as chemotaxis. Chemotaxis is a directional form of cell migration. Cytokines are a different set of soluble factors that can prompt leukocytes to move faster, but not in a directional manner. Such non-directional form of cell migration is referred to as cytokinesis.

One object of the present invention to provide a method to form a stable gradient. Another object of the present invention to provide a method of forming a stable gradient unaffected by fluid level disturbances, surface tension, evaporation, and other sources of pressure differentials. Another object of the present invention to provide a method of patterning particles within the stable gradient volume formed in the device.

As shown in FIG. 1, one embodiment of the microfluidic gradient device and microfluidic chemotaxis device includes a gradient channel 25 (also referred to as a conduit) in fluid communication with opposing fluid reservoirs including a source reservoir 11 and a sink reservoir 18. The height of the gradient channel 25 is less than the height of the source reservoir 11 or sink reservoir 18. The volume of the gradient channel 25 is less than the volume of the source reservoir 11 or the sink reservoir 18. The source reservoir 11 and sink reservoir 18 must each have sufficient capacity to maintain a static, stable gradient in the gradient channel 25 over the time period of interest, given the flux of gradient substance from the source reservoir 11 to the sink reservoir 18, largely determined by the gradient substance concentration in the source reservoir 11, the gradient channel 25 length and gradient channel 25 cross-sectional area.

The device also includes a closed circuit channel 26, which is also referred to as a bypass channel. The flow resistance of the closed circuit channel 26 is also significantly less than the flow resistance within the gradient channel 25. The flow resistance of the gradient channel 25 is approximately 300× higher than the flow resistance of the closed circuit channel 26, and a disturbance between the sink reservoir 18 and the source reservoir 11 leading to displacement of 0.1 μL of volume produces around 15 μm of mean longitudinal displacement in the gradient channel 25, indicating stability of the gradient in gradient channel 25.

A source port 12 is connected to the source reservoir 11, providing access to the volume of the source reservoir 11 from the outside. A sink port 19 is connected to the sink reservoir 18, providing access to the volume of the sink reservoir 18 from the outside. The source port 12 and sink port 19 are sized and shaped appropriately to allow for fluid addition using pipettes, and automated liquid handling robotics, including non-contact dispensing instruments such as ultrasonic and inkjet dispensers. If needed the ports are also suitably shaped to facilitate microfluidic passive pumping.

The longitudinal shape of the gradient channel 25 and closed circuit channel 26 may be rectangular so as to form a linear concentration gradient. The longitudinal shape of the gradient channel 25 and closed circuit channel 26 may also be curvalinear. The transverse cross-sectional shape of the gradient channel 25 and closed circuit channel 26 may be either rectangular or curvalinear. The length of the closed circuit channel 26 is predetermined such that diffusion through the closed circuit channel 26 does not transport the substance of interest to the sink reservoir 18 via the closed circuit channel 26 over the time period of interest.

To form a static and stable gradient in the gradient channel 25, the device is first filled with an appropriate fluid, such as phosphate buffered saline solution, or cell culture media. A solution containing a substance of interest may be added to the source reservoir 11 through the use of the source port 12, such that the solution fills the reservoir. Over time the substance diffuses through the gradient channel 25 into the sink reservoir 18, forming a gradient.

Should a disturbance occur over the course of an experiment producing a pressure gradient between the source reservoir 11 and the sink reservoir 18, the pressure gradient will be dissipated by liquid flow primarily through the closed circuit channel 26. The liquid flows primarily through the closed circuit channel 26 instead of the gradient channel 25 due to the significant difference in fluid flow resistance. By predetermining specific resistances for the gradient channel 25 and the closed circuit channel 26, any disturbance caused by a pressure gradient is limited below a predetermined volume displacement. The effect of the displacement can be predicted via finite element modeling of the flow pattern in the microfluidic device.

Figure 2:
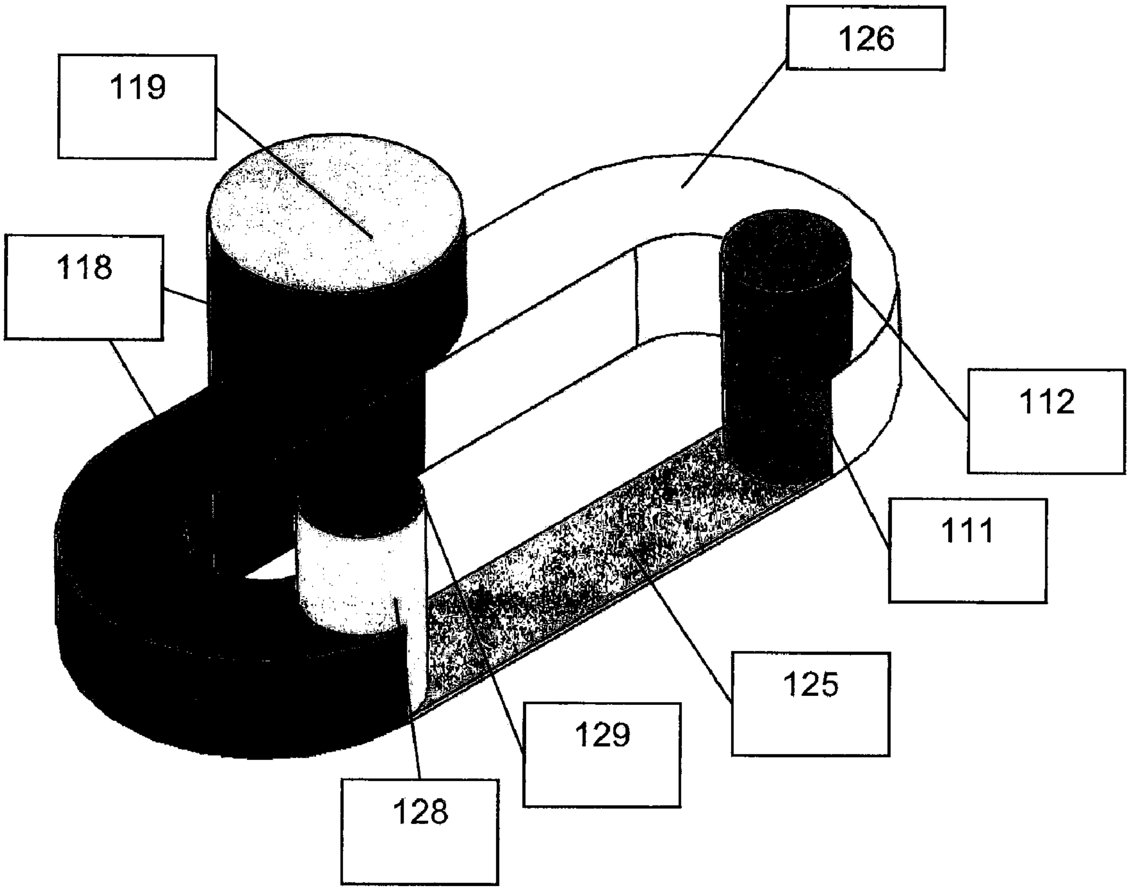
FIG. 2 is a perspective view of another embodiment of the microfluidic gradient device of the present invention, whereby the flow resistance of the gradient channel is approximately 5000× higher than the flow resistance of the closed circuit channel.

Another embodiment of the invention is shown in FIG. 2. This embodiment of the microfluidic gradient device and microfluidic chemotaxis device includes a gradient channel 125 (also referred to as a conduit) in fluid communication with opposing fluid reservoirs including a source reservoir 111 and a sink reservoir 118. The height of the gradient channel 125 is less than the height of the source reservoir 111 or sink reservoir 118. The volume of the gradient channel 125 is less than the volume of the source reservoir 111 or the sink reservoir 118. The source reservoir 111 and sink reservoir 118 must each have sufficient capacity to maintain a static, stable gradient in the gradient channel 125 over the time period of interest, given the flux of gradient substance from the source reservoir 111 to the sink reservoir 118, largely determined by the gradient substance concentration in the source reservoir 111, the gradient channel 125 length and gradient channel 125 cross-sectional area.

The device also includes a closed circuit channel 126, which is also referred to as a bypass channel. The flow resistance of the closed circuit channel 126 is also significantly less than the flow resistance within the gradient channel 125. The flow resistance of the gradient channel 125 is approximately 5000× higher than the flow resistance of the closed circuit channel 126, and a disturbance between the sink reservoir 118 and the source reservoir 111 leading to displacement of 0.1 μL of volume produces around 500 nm of mean longitudinal displacement in the gradient channel 125, indicating good stability of the gradient in gradient channel 125.

A source port 112 is connected to the source reservoir 111, providing access to the volume of the source reservoir 111 from the outside. A sink port 119 is connected to the sink reservoir 118, providing access to the volume of the sink reservoir 118 from the outside. The source port 112 and sink port 119 are sized and shaped appropriately to allow for fluid addition using pipettes, and automated liquid handling robotics, including non-contact dispensing instruments such as ultrasonic and inkjet dispensers. If needed the ports are also suitably shaped to facilitate microfluidic passive pumping.

The device also includes a cell addition reservoir 128, which is in fluidic communication with the sink reservoir 118. A cell addition port 129 is connected to the cell addition reservoir 128 and provides access to the call addition reservoir from the outside. The cell addition port 129 is sized and shaped appropriately to allow for fluid addition using pipettes, and automated liquid handling robotics, including non-contact dispensing instruments such as ultrasonic and inkjet dispensers. If needed the cell addition port 129 is also suitably shaped to facilitate microfluidic passive pumping. Cells may be provided in the devices by pipetting a cell suspension to the cell addition port 129.

The longitudinal shape of the gradient channel 125 and closed circuit channel 126 may be rectangular so as to form a linear concentration gradient. The longitudinal shape of the gradient channel 125 and closed circuit channel 126 may also be curvalinear. The transverse cross-sectional shape of the gradient channel 125 and closed circuit channel 126 may be either rectangular or curvalinear. The length of the closed circuit channel 126 is predetermined such that diffusion through the closed circuit channel 126 does not transport the substance of interest to the sink reservoir 118 via the closed circuit channel 126 over the time period of interest.

To form a static and stable gradient in the gradient channel 125, the device is first filled with an appropriate fluid, such as phosphate buffered saline solution, or cell culture media. A solution containing a substance of interest may be added to the source reservoir 11 through the use of the source port 112, such that the solution fills the reservoir. Over time the substance diffuses through the gradient channel 125 into the sink reservoir 118, forming a gradient. Should a disturbance occur over the course of an experiment producing a pressure gradient between the source reservoir 111 and the sink reservoir 118, the pressure gradient will be dissipated by liquid flow primarily through the closed circuit channel 126. The liquid flows primarily through the closed circuit channel 126 instead of the gradient channel 125 due to the significant difference in fluid flow resistance. By predetermining specific resistances for the gradient channel 125 and the closed circuit channel 126, any disturbance caused by a pressure gradient is limited below a predetermined volume displacement. The effect of the displacement can be predicted via finite element modeling of the flow pattern in the microfluidic device.

Figure 3:
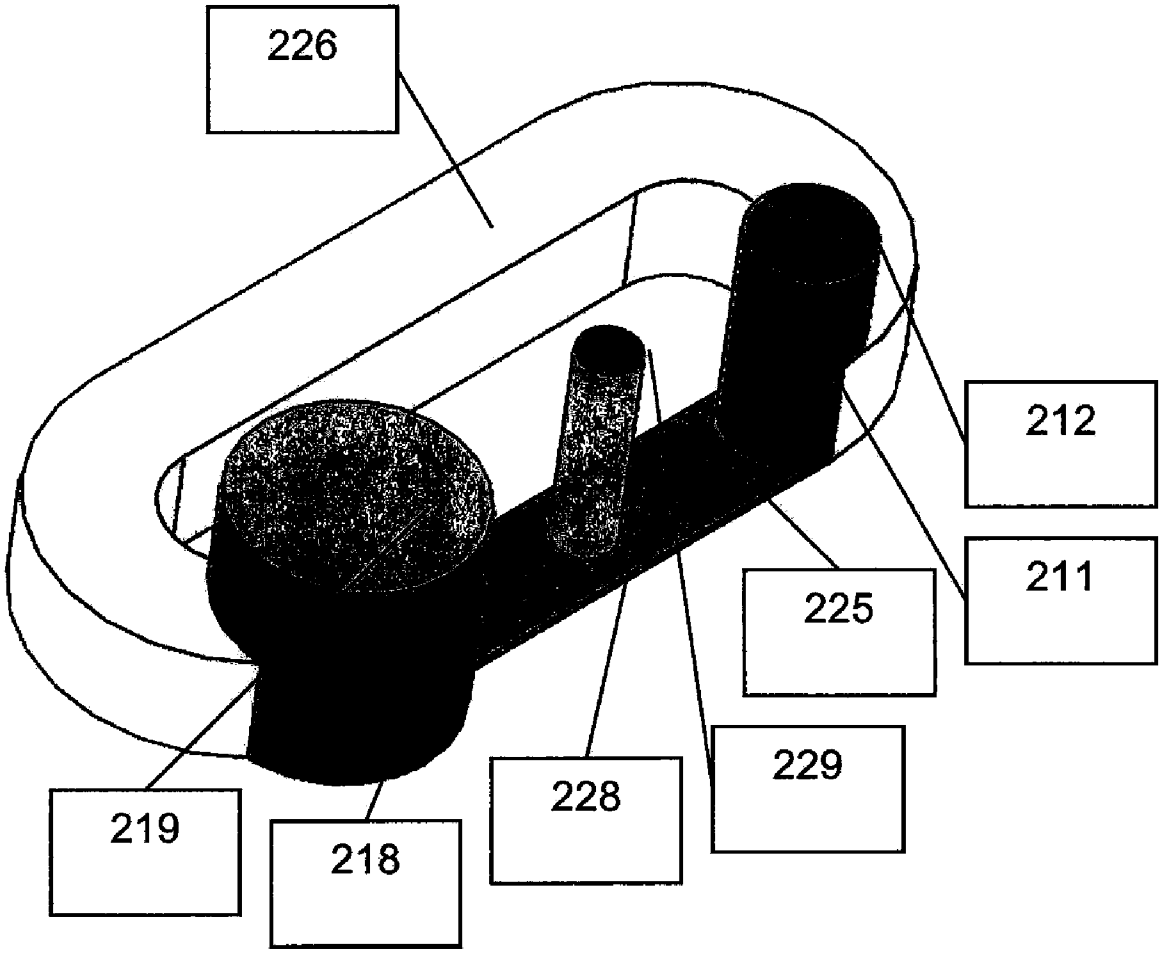
FIG. 3 is a perspective view of another embodiment of the microfluidic gradient device of the present invention whereby the flow resistance of the gradient channel is approximately 3000× higher than the flow resistance of the closed circuit channel.

Another embodiment of the invention is shown in FIG. 3. This embodiment of the microfluidic gradient device and microfluidic chemotaxis device includes a gradient channel 225 (also referred to as a conduit) in fluid communication with opposing fluid reservoirs including a source reservoir 211 and a sink reservoir 218. The height of the gradient channel 225 is less than the height of the source reservoir 211 or sink reservoir 218. The volume of the gradient channel 225 is less than the volume of the source reservoir 211 or the sink reservoir 218. The source reservoir 211 and sink reservoir 218 must each have sufficient capacity to maintain a static, stable gradient in the gradient channel 225 over the time period of interest, given the flux of gradient substance from the source reservoir 211 to the sink reservoir 218, largely determined by the gradient substance concentration in the source reservoir 211, the gradient channel 225 length and gradient channel 225 cross-sectional area.

The device also includes a closed circuit channel 226, which is also referred to as a bypass channel. The flow resistance of the closed circuit channel 226 is also significantly less than the flow resistance within the gradient channel 225. The flow resistance of the gradient channel 225 is approximately 3000× higher than the flow resistance of the closed circuit channel 226, and a disturbance between the sink reservoir 218 and the source reservoir 211 leading to displacement of 0.1 μL of volume produces around 1 μm of mean longitudinal displacement in the gradient channel 225, indicating good stability of the gradient in gradient channel 225.

A source port 212 is connected to the source reservoir 211, providing access to the volume of the source reservoir 211 from the outside. A sink port 219 is connected to the sink reservoir 218, providing access to the volume of the sink reservoir 218 from the outside. The source port 212 and sink port 219 are sized and shaped appropriately to allow for fluid addition using pipettes, and automated liquid handling robotics, including non-contact dispensing instruments such as ultrasonic and inkjet dispensers. If needed the ports are also suitably shaped to facilitate microfluidic passive pumping.

The device also includes a cell addition reservoir 228, which is in fluidic communication with the gradient channel 225. A cell addition port 229 is connected to the cell addition reservoir 228 and provides access to the call addition reservoir from the outside. The cell addition port 229 is sized and shaped appropriately to allow for fluid addition using pipettes, and automated liquid handling robotics, including non-contact dispensing instruments such as ultrasonic and inkjet dispensers. If needed the cell addition port 229 is also suitably shaped to facilitate microfluidic passive pumping. Cells may be provided in the devices by pipetting a cell suspension to the cell addition port 229.

The longitudinal shape of the gradient channel 225 and closed circuit channel 226 may be rectangular so as to form a linear concentration gradient. The longitudinal shape of the gradient channel 225 and closed circuit channel 226 may also be curvalinear. The transverse cross-sectional shape of the gradient channel 225 and closed circuit channel 226 may be either rectangular or curvalinear. The length of the closed circuit channel 226 is predetermined such that diffusion through the closed circuit channel 226 does not transport the substance of interest to the sink reservoir 218 via the closed circuit channel 226 over the time period of interest.

To form a static and stable gradient in the gradient channel 225, the device is first filled with an appropriate fluid, such as phosphate buffered saline solution, or cell culture media. A solution containing a substance of interest may be added to the source reservoir 211 through the use of the source port 212, such that the solution fills the reservoir. Over time the substance diffuses through the gradient channel 225 into the sink reservoir 218, forming a gradient, Should a disturbance occur over the course of an experiment producing a pressure gradient between the source reservoir 211 and the sink reservoir 218, the pressure gradient will be dissipated by liquid flow primarily through the closed circuit channel 226. The liquid flows primarily through the closed circuit channel 226 instead of the gradient channel 225 due to the significant difference in fluid flow resistance. By predetermining specific resistances for the gradient channel 225 and the closed circuit channel 226, any disturbance caused by a pressure gradient is limited below a predetermined volume displacement. The effect of the displacement can be predicted via finite element modeling of the flow pattern in the microfluidic device.

Figure 4:
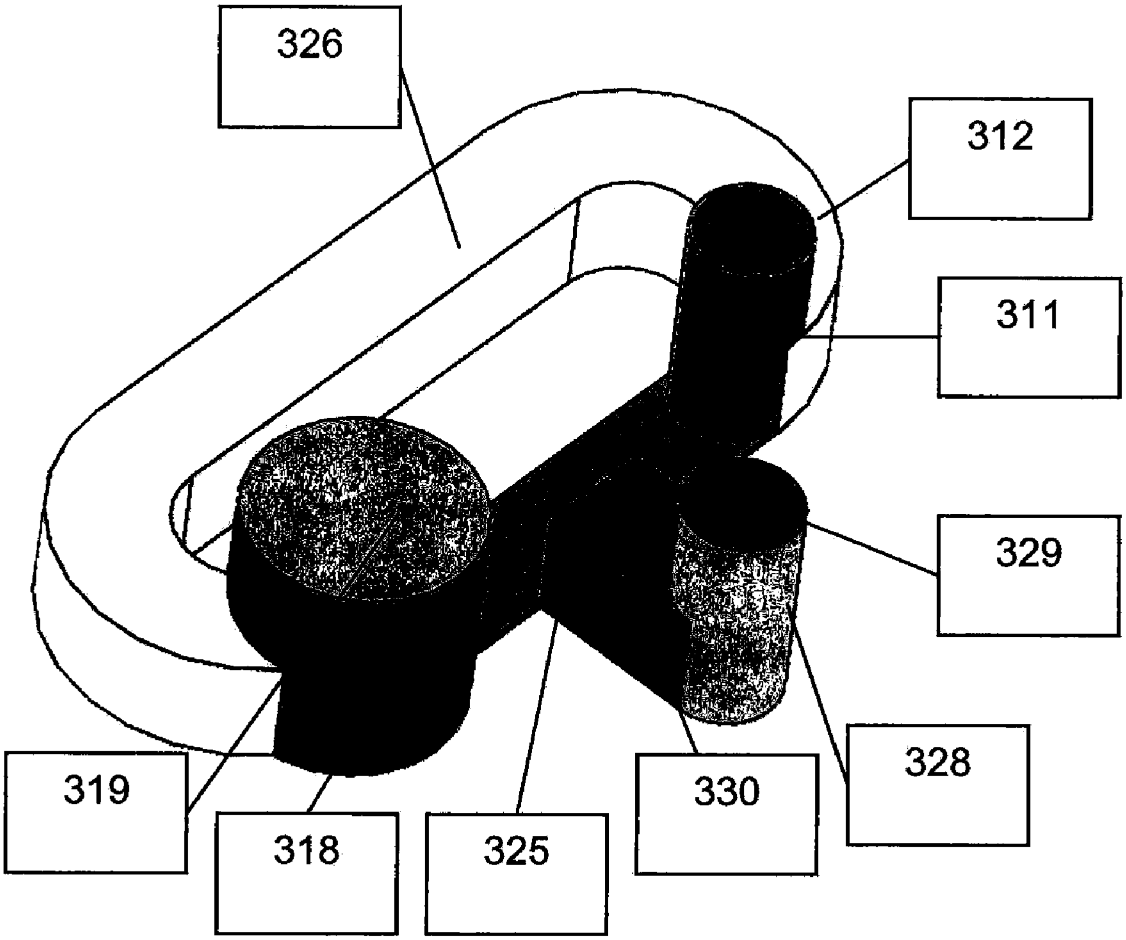
FIG. 4 is a perspective view of another embodiment of the microfluidic gradient device of the present invention whereby the flow resistance of the gradient channel is approximately 3000× higher than the flow resistance of the closed circuit channel.

Another embodiment of the invention is shown in FIG. 4. This embodiment of the microfluidic gradient device and microfluidic chemotaxis device includes a gradient channel 325 (also referred to as a conduit) in fluid communication with opposing fluid reservoirs including a source reservoir 311 and a sink reservoir 318. The height of the gradient channel 325 is less than the height of the source reservoir 311 or sink reservoir 318. The volume of the gradient channel 325 is less than the volume of the source reservoir 311 or the sink reservoir 318. The source reservoir 311 and sink reservoir 318 must each have sufficient capacity to maintain a static, stable gradient in the gradient channel 325 over the time period of interest, given the flux of gradient substance from the source reservoir 311 to the sink reservoir 318, largely determined by the gradient substance concentration in the source reservoir 311, the gradient channel 325 length and gradient channel 325 cross-sectional area.

The device also includes a closed circuit channel 326, which is also referred to as a bypass channel. The flow resistance of the closed circuit channel 326 is also significantly less than the flow resistance within the gradient channel 325. The flow resistance of the gradient channel 325 is approximately 3000× higher than the flow resistance of the closed circuit channel 326, and a disturbance between the sink reservoir 318 and the source reservoir 311 leading to displacement of 0.1 μL of volume produces around 1 μm of mean longitudinal displacement in the gradient channel 325, indicating good stability of the gradient in gradient channel 325.

A source port 312 is connected to the source reservoir 311, providing access to the volume of the source reservoir 311 from the outside. A sink port 319 is connected to the sink reservoir 318, providing access to the volume of the sink reservoir 318 from the outside. The source port 312 and sink port 319 are sized and shaped appropriately to allow for fluid addition using pipettes, and automated liquid handling robotics, including non-contact dispensing instruments such as ultrasonic and inkjet dispensers. If needed the ports are also suitably shaped to facilitate microfluidic passive pumping.

The device also includes a cell addition reservoir 328 and a cell addition channel. The cell addition channel is in fluid communication with the gradient channel 325 and the cell addition reservoir 328 and provides access to the call addition reservoir from the outside. A cell addition port 329 is connected to the cell addition reservoir 328. The cell addition port 329 is sized and shaped appropriately to allow for fluid addition using pipettes, and automated liquid handling robotics, including non-contact dispensing instruments such as ultrasonic and inkjet dispensers. If needed the cell addition port 329 is also suitably shaped to facilitate microfluidic passive pumping. Cells may be provided in the devices by pipetting a cell suspension to the cell addition port 329.

The longitudinal shape of the gradient channel 325 and closed circuit channel 326 may be rectangular so as to form a linear concentration gradient. The longitudinal shape of the gradient channel 325 and closed circuit channel 326 may also be curvalinear. The transverse cross-sectional shape of the gradient channel 325 and closed circuit channel 326 may be either rectangular or curvalinear. The length of the closed circuit channel 326 is predetermined such that diffusion through the closed circuit channel 326 does not transport the substance of interest to the sink reservoir 318 via the closed circuit channel 326 over the time period of interest. To form a static and stable gradient in the gradient channel 325, the device is first filled with an appropriate fluid, such as phosphate buffered saline solution, or cell culture media. A solution containing a substance of interest may be added to the source reservoir 311 through the use of the source port 312, such that the solution fills the reservoir. Over time the substance diffuses through the gradient channel 325 into the sink reservoir 318, forming a gradient. Should a disturbance occur over the course of an experiment producing a pressure gradient between the source reservoir 311 and the sink reservoir 318, the pressure gradient will be dissipated by liquid flow primarily through the closed circuit channel 326. The liquid flows primarily through the closed circuit channel 326 instead of the gradient channel 325 due to the significant difference in fluid flow resistance. By predetermining specific resistances for the gradient channel 325 and the closed circuit channel 326, any disturbance caused by a pressure gradient is limited below a predetermined volume displacement. The effect of the displacement can be predicted via finite element modeling of the flow pattern in the microfluidic device.

Figure 5:
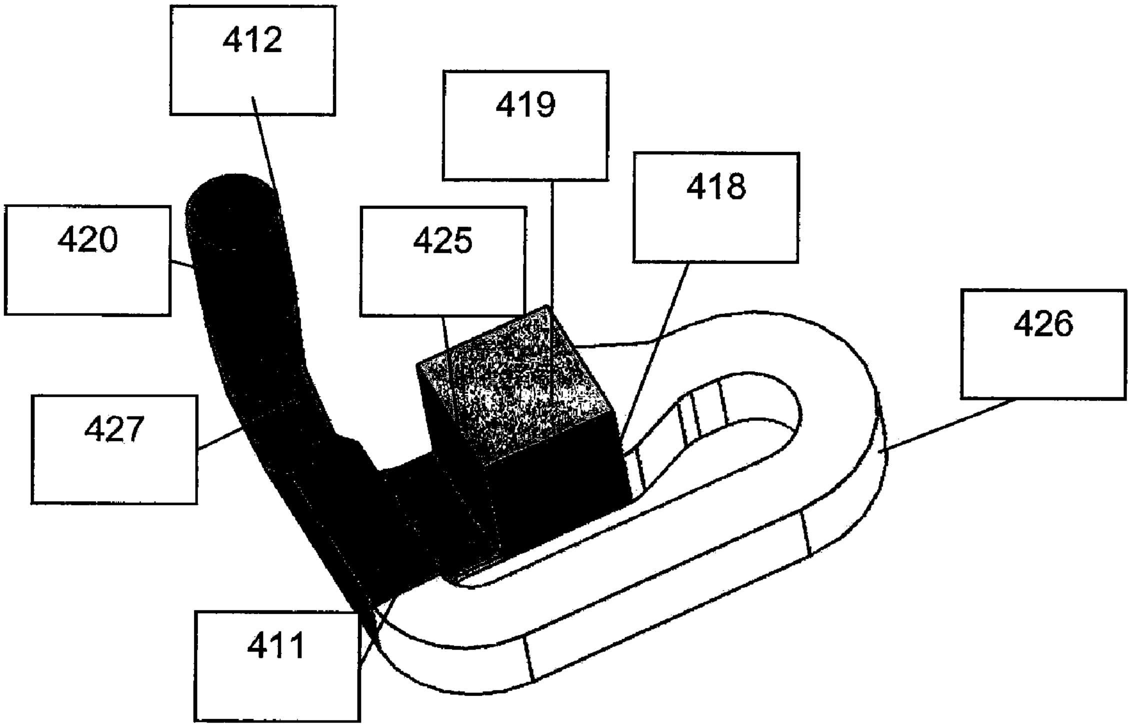
FIG. 5 is a perspective view of another embodiment of the microfluidic gradient device of the present invention whereby the flow resistance of the gradient channel is approximately 60× higher than the flow resistance of the closed circuit channel.

Another embodiment of the invention is shown in FIG. 5. This embodiment of the microfluidic gradient device and microfluidic chemotaxis device includes a gradient channel 425 (also referred to as a conduit) in fluid communication with opposing fluid reservoirs including a source reservoir 411 and a sink reservoir 418. The height of the gradient channel 425 is less than the height of the source reservoir 411 or sink reservoir 418. The volume of the gradient channel 425 is less than the volume of the source reservoir 411 or the sink reservoir 418. The source reservoir 411 and sink reservoir 418 must each have sufficient capacity to maintain a static, stable gradient in the gradient channel 425 over the time period of interest, given the flux of gradient substance from the source reservoir 411 to the sink reservoir 418, largely determined by the gradient substance concentration in the source reservoir 411, the gradient channel 425 length and gradient channel 425 cross-sectional area.

The device also includes a closed circuit channel 426, which is also referred to as a bypass channel. The flow resistance of the closed circuit channel 426 is also significantly less than the flow resistance within the gradient channel 425. The flow resistance of the gradient channel 425 is approximately 60× higher than the flow resistance of the closed circuit channel 426, and a disturbance between the sink reservoir 418 and the source reservoir 411 leading to displacement of 0.1 μL of volume produces around 10 μm of mean longitudinal displacement in the gradient channel 425, indicating good stability of the gradient in gradient channel 425.

A source port 412 is connected to the source input reservoir 420, providing access to the volume of the source input reservoir 420 from the outside. A sink port 419 is connected to the sink reservoir 418, providing access to the volume of the sink reservoir 418 from the outside. The auxiliary channel is in fluid communication with the source input reservoir 420 and the source reservoir 411. The source port 412 and sink port 419 are sized and shaped appropriately to allow for fluid addition using pipettes, and automated liquid handling robotics, including non-contact dispensing instruments such as ultrasonic and inkjet dispensers. If needed the ports are also suitably shaped to facilitate microfluidic passive pumping.

The longitudinal shape of the gradient channel 425 and closed circuit channel 426 may be rectangular so as to form a linear concentration gradient. The longitudinal shape of the gradient channel 425 and closed circuit channel 426 may also be curvalinear. The transverse cross-sectional shape of the gradient channel 425 and closed circuit channel 426 may be either rectangular or curvalinear. The length of the closed circuit channel 426 is predetermined such that diffusion through the closed circuit channel 426 does not transport the substance of interest to the sink reservoir 418 via the closed circuit channel 426 over the time period of interest.

To form a static and stable gradient in the gradient channel 425, the device is first filled with an appropriate fluid, such as phosphate buffered saline solution, or cell culture media. A solution containing a substance of interest may be added to the source reservoir 411 through the use of the source port 412, such that the solution fills the reservoir. Over time the substance diffuses through the gradient channel 425 into the sink reservoir 418, forming a gradient. Should a disturbance occur over the course of an experiment producing a pressure gradient between the source reservoir 411 and the sink reservoir 418, the pressure gradient will be dissipated by liquid flow primarily through the closed circuit channel 426. The liquid flows primarily through the closed circuit channel 426 instead of the gradient channel 425 due to the significant difference in fluid flow resistance. By predetermining specific resistances for the gradient channel 425 and the closed circuit channel 426, any disturbance caused by a pressure gradient is limited below a predetermined volume displacement. The effect of the displacement can be predicted via finite element modeling of the flow pattern in the microfluidic device.

Figure 6:
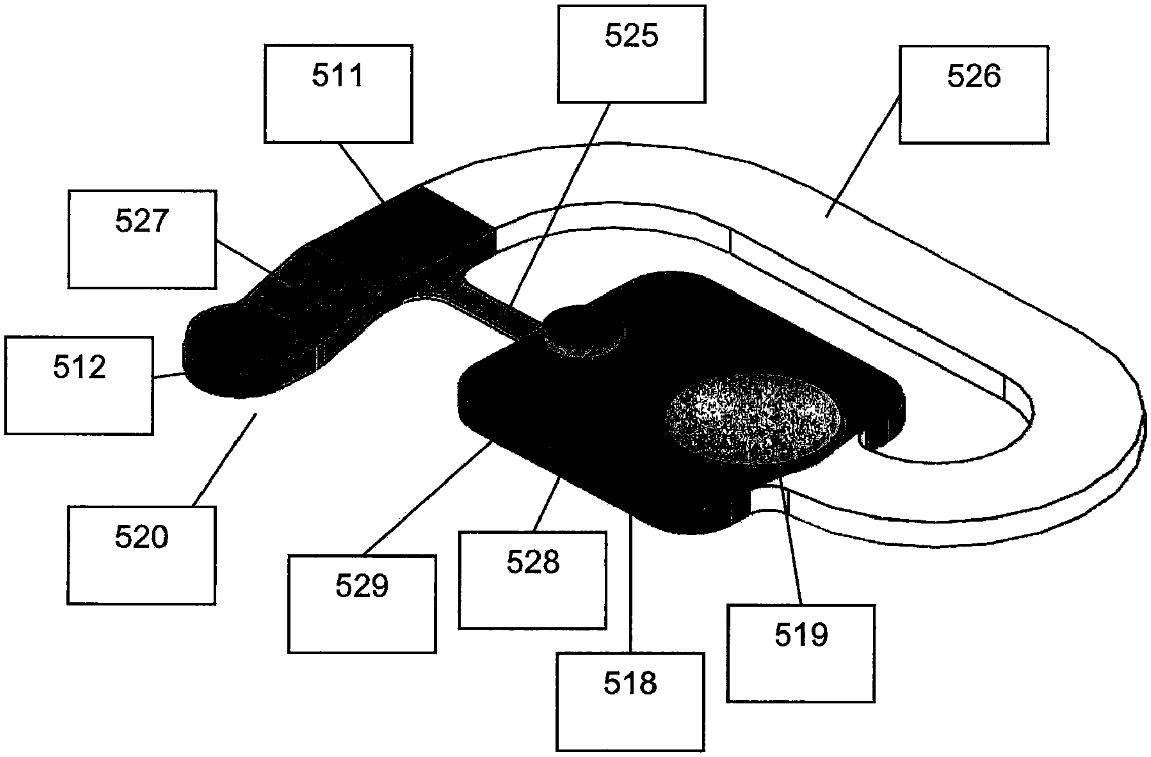
FIG. 6 is a perspective view of another embodiment of the microfluidic gradient device of the present invention whereby the flow resistance of the gradient channel is approximately 100× higher than the flow resistance of the closed circuit channel.

Another embodiment of the invention is shown in FIG. 6. This embodiment of the microfluidic gradient device and microfluidic chemotaxis device includes a gradient channel 525 (also referred to as a conduit) in fluid communication with opposing fluid reservoirs including a source reservoir 511 and a sink reservoir 518. The height of the gradient channel 525 is less than the height of the source reservoir 511 or sink reservoir 518. The volume of the gradient channel 525 is less than the volume of the source reservoir 511 or the sink reservoir 518. The source reservoir 511 and sink reservoir 518 must each have sufficient capacity to maintain a static, stable gradient in the gradient channel 525 over the time period of interest, given the flux of gradient substance from the source reservoir 511 to the sink reservoir 518, largely determined by the gradient substance concentration in the source reservoir 511, the gradient channel 525 length and gradient channel 525 cross-sectional area.

The device also includes a closed circuit channel 526, which is also referred to as a bypass channel. The flow resistance of the closed circuit channel 526 is also significantly less than the flow resistance within the gradient channel 525. The flow resistance of the gradient channel 525 is approximately 100× higher than the flow resistance of the closed circuit channel 526, and a disturbance between the sink reservoir 518 and the source reservoir 511 leading to displacement of 0.1 μL of volume produces around 90 μm of mean longitudinal displacement in the gradient channel 525, indicating good stability of the gradient in gradient channel 525.

A source port 512 is connected to the source input reservoir 520, providing access to the volume of the source input reservoir 520 from the outside. A sink port 519 is connected to the sink reservoir 518, providing access to the volume of the sink reservoir 518 from the outside. The auxiliary channel is in fluid communication with the source input reservoir 520 and the source reservoir 511. The source port 512 and sink port 519 are sized and shaped appropriately to allow for fluid addition using pipettes, and automated liquid handling robotics, including non-contact dispensing instruments such as ultrasonic and inkjet dispensers. If needed the ports are also suitably shaped to facilitate microfluidic passive pumping.

The device also includes a cell addition reservoir 528, which is in fluidic communication with the sink reservoir 518. A cell addition port 529 is connected to the cell addition reservoir 528. The cell addition port 529 is sized and shaped appropriately to allow for fluid addition using pipettes, and automated liquid handling robotics, including non-contact dispensing instruments such as ultrasonic and inkjet dispensers. If needed the cell addition port 529 is also suitably shaped to facilitate microfluidic passive pumping.

The longitudinal shape of the gradient channel 525 and closed circuit channel 526 may be rectangular so as to form a linear concentration gradient. The longitudinal shape of the gradient channel 525 and closed circuit channel 526 may also be curvalinear. The transverse cross-sectional shape of the gradient channel 525 and closed circuit channel 526 may be either rectangular or curvalinear. The length of the closed circuit channel 526 is predetermined such that diffusion through the closed circuit channel 526 does not transport the substance of interest to the sink reservoir 518 via the closed circuit channel 526 over the time period of interest.

To form a static and stable gradient in the gradient channel 525, the device is first filled with an appropriate fluid, such as phosphate buffered saline solution, or cell culture media. A solution containing a substance of interest may be added to the source reservoir 511 through the use of the source port 512, such that the solution fills the reservoir. Over time the substance diffuses through the gradient channel 525 into the sink reservoir 518, forming a gradient. Should a disturbance occur over the course of an experiment producing a pressure gradient between the source reservoir 511 and the sink reservoir 518, the pressure gradient will be dissipated by liquid flow primarily through the closed circuit channel 526. The liquid flows primarily through the closed circuit channel 526 instead of the gradient channel 525 due to the significant difference in fluid flow resistance. By predetermining specific resistances for the gradient channel 525 and the closed circuit channel 526, any disturbance caused by a pressure gradient is limited below a predetermined volume displacement. The effect of the displacement can be predicted via finite element modeling of the flow pattern in the microfluidic device.

Figure 7:
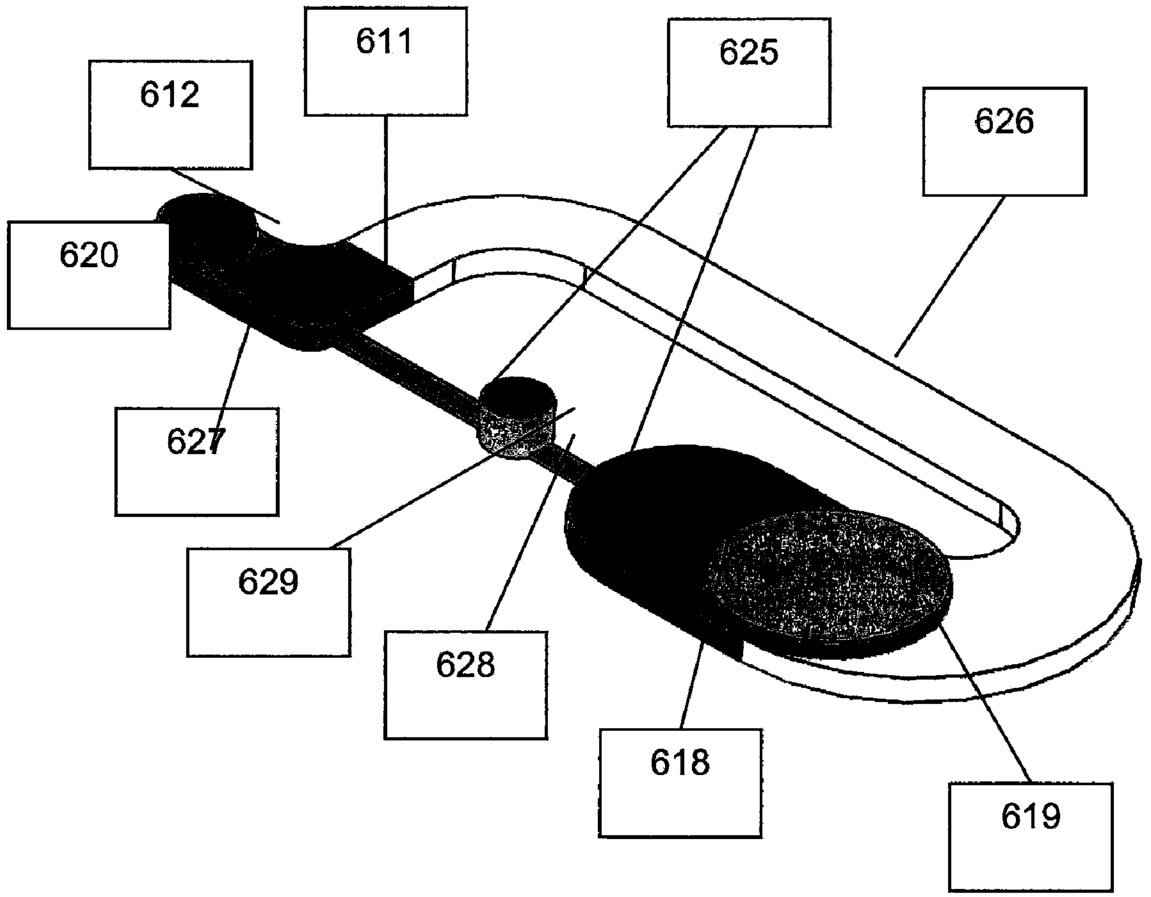
FIG. 7 is a perspective view of another embodiment of the microfluidic gradient device of the present invention whereby the flow resistance of the gradient channel is approximately 300× higher than the flow resistance of the closed circuit channel.

Another embodiment of the invention is shown in FIG. 7. This embodiment of the microfluidic gradient device and microfluidic chemotaxis device includes a gradient channel 625 (also referred to as a conduit) in fluid communication with opposing fluid reservoirs including a source reservoir 611 and a sink reservoir 618. The height of the gradient channel 625 is less than the height of the source reservoir 611 or sink reservoir 618. The volume of the gradient channel 625 is less than the volume of the source reservoir 611 or the sink reservoir 618. The source reservoir 611 and sink reservoir 618 must each have sufficient capacity to maintain a static, stable gradient in the gradient channel 625 over the time period of interest, given the flux of gradient substance from the source reservoir 611 to the sink reservoir 618, largely determined by the gradient substance concentration in the source reservoir 611, the gradient channel 625 length and gradient channel 625 cross-sectional area.

The device also includes a closed circuit channel 626, which is also referred to as a bypass channel. The flow resistance of the closed circuit channel 626 is also significantly less than the flow resistance within the gradient channel 625. The flow resistance of the gradient channel 625 is approximately 300× higher than the flow resistance of the closed circuit channel 626, and a disturbance between the sink reservoir 618 and the source reservoir 611 leading to displacement of 0.1 μL of volume produces around 25 μm of mean longitudinal displacement in the gradient channel 625, indicating good stability of the gradient in gradient channel 625.

A source port 612 is connected to the source input reservoir 620, providing access to the volume of the source input reservoir 620 from the outside. A sink port 619 is connected to the sink reservoir 618, providing access to the volume of the sink reservoir 618 from the outside. The auxiliary channel is in fluid communication with the source input reservoir 620 and the source reservoir 611. The source port 612 and sink port 619 are sized and shaped appropriately to allow for fluid addition using pipettes, and automated liquid handling robotics, including non-contact dispensing instruments such as ultrasonic and inkjet dispensers. If needed the ports are also suitably shaped to facilitate microfluidic passive pumping.

The device also includes a cell addition reservoir 628, which is in fluidic communication with the gradient channel 625. A cell addition port 629 is connected to the cell addition reservoir 628 and provides access to the call addition reservoir from the outside. The cell addition port 629 is sized and shaped appropriately to allow for fluid addition using pipettes, and automated liquid handling robotics, including non-contact dispensing instruments such as ultrasonic and inkjet dispensers. If needed the cell addition port 629 is also suitably shaped to facilitate microfluidic passive pumping. Cells may be provided in the devices by pipetting a cell suspension to the cell addition port 629.

The longitudinal shape of the gradient channel 625 and closed circuit channel 626 may be rectangular so as to form a linear concentration gradient. The longitudinal shape of the gradient channel 625 and closed circuit channel 626 may also be curvalinear. The transverse cross-sectional shape of the gradient channel 625 and closed circuit channel 626 may be either rectangular or curvalinear. The length of the closed circuit channel 626 is predetermined such that diffusion through the closed circuit channel 626 does not transport the substance of interest to the sink reservoir 618 via the closed circuit channel 626 over the time period of interest.

To form a static and stable gradient in the gradient channel 625, the device is first filled with an appropriate fluid, such as phosphate buffered saline solution, or cell culture media. A solution containing a substance of interest may be added to the source reservoir 611 through the use of the source port 612, such that the solution fills the reservoir. Over time the substance diffuses through the gradient channel 625 into the sink reservoir 618, forming a gradient. Should a disturbance occur over the course of an experiment producing a pressure gradient between the source reservoir 611 and the sink reservoir 618, the pressure gradient will be dissipated by liquid flow primarily through the closed circuit channel 626. The liquid flows primarily through the closed circuit channel 626 instead of the gradient channel 625 due to the significant difference in fluid flow resistance. By predetermining specific resistances for the gradient channel 625 and the closed circuit channel 626, any disturbance caused by a pressure gradient is limited below a predetermined volume displacement. The effect of the displacement can be predicted via finite element modeling of the flow pattern in the microfluidic device.

Figure 8:
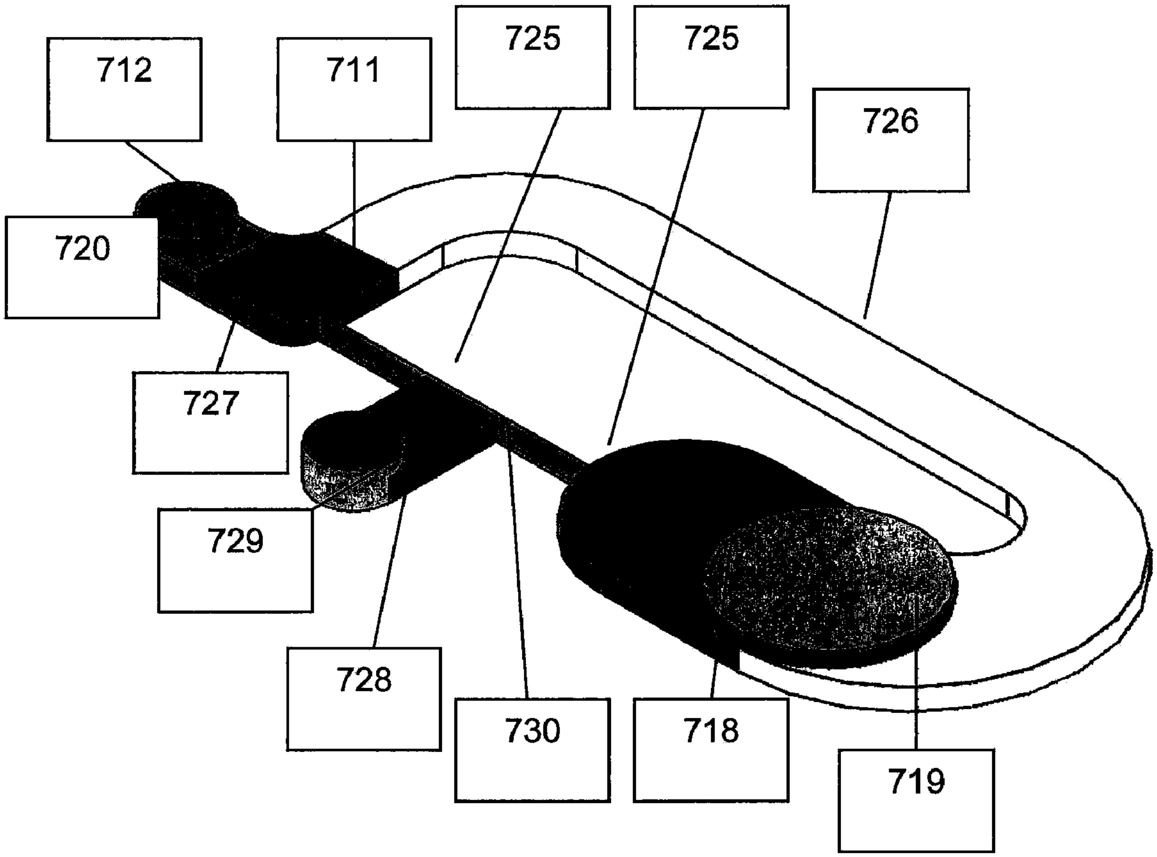
FIG. 8 is a perspective view of another embodiment of the microfluidic gradient device of the present invention whereby the flow resistance of the gradient channel is approximately 300× higher than the flow resistance of the closed circuit channel.

Another embodiment of the invention is shown in FIG. 8. This embodiment of the microfluidic gradient device and microfluidic chemotaxis device includes a gradient channel 725 (also referred to as a conduit) in fluid communication with opposing fluid reservoirs including a source reservoir 711 and a sink reservoir 718. The height of the gradient channel 725 is less than the height of the source reservoir 711 or sink reservoir 718. The volume of the gradient channel 725 is less than the volume of the source reservoir 711 or the sink reservoir 718. The source reservoir 711 and sink reservoir 718 must each have sufficient capacity to maintain a static, stable gradient in the gradient channel 725 over the time period of interest, given the flux of gradient substance from the source reservoir 711 to the sink reservoir 718, largely determined by the gradient substance concentration in the source reservoir 711, the gradient channel 725 length and gradient channel 725 cross-sectional area.

The device also includes a closed circuit channel 726, which is also referred to as a bypass channel. The flow resistance of the closed circuit channel 726 is also significantly less than the flow resistance within the gradient channel 725. The flow resistance of the gradient channel 725 is approximately 300× higher than the flow resistance of the closed circuit channel 726, and a disturbance between the sink reservoir 718 and the source reservoir 711 leading to displacement of 0.1 μL of volume produces around 25 μm of mean longitudinal displacement in the gradient channel 725, indicating good stability of the gradient in gradient channel 725.

A source port 712 is connected to the source input reservoir 720, providing access to the volume of the source input reservoir 720 from the outside. A sink port 719 is connected to the sink reservoir 718, providing access to the volume of the sink reservoir 718 from the outside. The auxiliary channel is in fluid communication with the source input reservoir 720 and the source reservoir 711. The source port 712 and sink port 719 are sized and shaped appropriately to allow for fluid addition using pipettes, and automated liquid handling robotics, including non-contact dispensing instruments such as ultrasonic and inkjet dispensers. If needed the ports are also suitably shaped to facilitate microfluidic passive pumping.

The device also includes a cell addition reservoir 728 and a cell addition channel. The cell addition channel is in fluid communication with the gradient channel 725 and the cell addition reservoir 728 and provides access to the call addition reservoir from the outside. A cell addition port 729 is connected to the cell addition reservoir 728. The cell addition port 729 is sized and shaped appropriately to allow for fluid addition using pipettes, and automated liquid handling robotics, including non-contact dispensing instruments such as ultrasonic and inkjet dispensers. If needed the cell addition port 729 is also suitably shaped to facilitate microfluidic passive pumping. Cells may be provided in the devices by pipetting a cell suspension to the cell addition port.

The longitudinal shape of the gradient channel 725 and closed circuit channel 726 may be rectangular so as to form a linear concentration gradient. The longitudinal shape of the gradient channel 725 and closed circuit channel 726 may also be curvalinear. The transverse cross-sectional shape of the gradient channel 725 and closed circuit channel 726 may be either rectangular or curvalinear. The length of the closed circuit channel 726 is predetermined such that diffusion through the closed circuit channel 726 does not transport the substance of interest to the sink reservoir 718 via the closed circuit channel 726 over the time period of interest.

To form a static and stable gradient in the gradient channel 725, the device is first filled with an appropriate fluid, such as phosphate buffered saline solution, or cell culture media. A solution containing a substance of interest may be added to the source reservoir 711 through the use of the source port 712, such that the solution fills the reservoir. Over time the substance diffuses through the gradient channel 725 into the sink reservoir 718, forming a gradient. Should a disturbance occur over the course of an experiment producing a pressure gradient between the source reservoir 711 and the sink reservoir 718, the pressure gradient will be dissipated by liquid flow primarily through the closed circuit channel 726. The liquid flows primarily through the closed circuit channel 726 instead of the gradient channel 725 due to the significant difference in fluid flow resistance. By predetermining specific resistances for the gradient channel 725 and the closed circuit channel 726, any disturbance caused by a pressure gradient is limited below a predetermined volume displacement. The effect of the displacement can be predicted via finite element modeling of the flow pattern in the microfluidic device.

EXAMPLES

Device manufacturing. A three-layer master mold was made using UV-curable epoxy (SU-8 25, SU-8 100, Microchem Corp.) on 6-inch polished silicon wafers. The mold structure was replicated in poly(dimethylsiloxane) (PDMS, Dow Corning). The PDMS replica was placed either on a 3 in.×1 in. glass slide or in a 35 mm polystyrene (PS) petri dish. PDMS spontaneously formed a reversible bond on glass and polystyrene.

Alternatively, devices can be manufactured via hot embossing. An embossing tool is produced via milling in aluminum, carbon steel or stainless steel. The faces corresponding to the device top and/or bottom, and channel top or bottom are mirror polished to provide optical clarity. A thin polystyrene sheet in the range of 0.375-2 mm, with optical surface finish, is placed between the two halves of the embossing tool and heated above the melting point of polystyrene (approximately 120 degrees C.) for a period of time, and subsequently cooled down. A polystyrene film ranging 25-250 μm thick is punched or drilled to provide access holes to the channels. Alternatively, the embossed sheet is punched or drilled to provide access to the channels. The polystyrene film is bonded to the embossed sheet to seal the channels.

Alternatively, a different material may be used for sheet and film, including cyclo-olefin polymer (COP), cyclo-olefin co-polymer (COC), polycarbonate (PC), polypropylene (PP), poly-methyl-methacrylate (PMMA), poly-ethylene-terephthalate (PET), high density polyethylene (HDPE), poly-methyl-pentene (PMP), high-impact polystyrene (HIPS), styrene-butadiene copolymer (SBC), acetonitrile-butadiene-styrene co-polymer (ABS) and cellulose acetate.

Bonding is achieved by placing the film and sheet together in a stack and applying heat and pressure until a diffusion bond is realized.

Alternatively, bonding can be achieved by laser welding, ultrasonic welding, adhesive bonding, ultra-violet light curable adhesive bonding, solvent bonding, solvent-assisted thermal bonding, plasma-assisted thermal bonding, microwave bonding, inductive bonding, vibration welding or hot tool welding.

Figure 9:
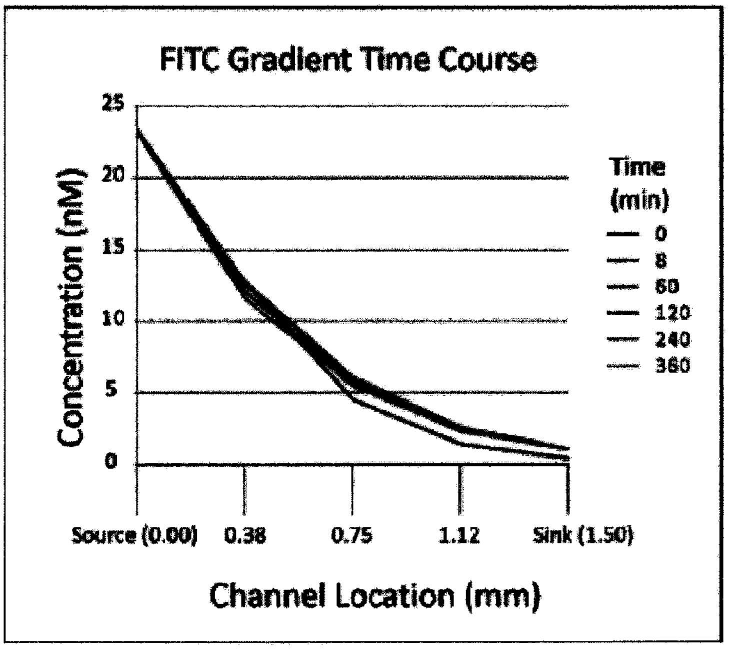
FIG. 9 shows the distribution of fluorescein isothiocyanate (FITC) concentration along the length of the gradient channel of a polystyrene microfluidic device analogous to that shown in FIG. 5. Initially the entire channel network is filled with RPMI+10% FBS. A source of 100 nM FITC in RPMI+10% FBS is then provided in the source assembly at the left hand side of the gradient channel. A gradient is establish over 30 minutes and remains stable for at least 360 minutes.

Characterization using fluorescent molecules. Next, the device fabricated from polystyrene was wick-filled with RPMI media containing 10% fetal bovine serum (FBS). A fluorescent dye solution (FITC, Sigma-Aldrich) was prepared at 100 nM concentration in RPMI containing 10% FBS. The experiment was initiated by dispensing 2 μL of the dye solution at the source access port. Subsequently, the distribution of the dye was monitored on an inverted microscope equipped with a monitoring assembly including a broad spectrum light source, a suitable excitation filter, a dichroic mirror, and a high sensitivity charge coupled device (CCD) camera. The gradient concentration plots showing the fluorescence intensity distribution over 6 hours is shown in FIG. 9. A gradient formed in the channel was consistent with diffusion of the dye molecule into the channel.

Figure 10:
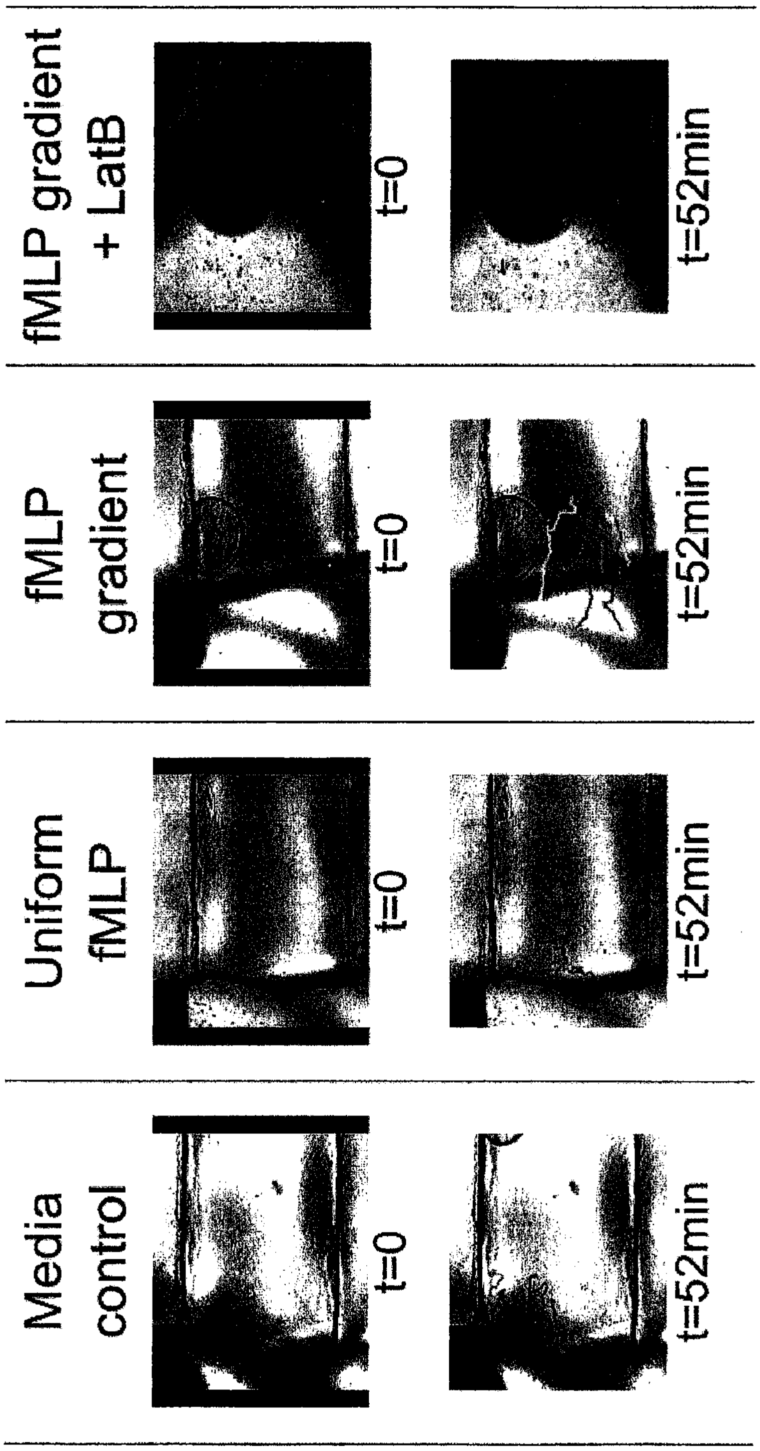
FIG. 10 shows a time course of phase contrast photomicrograph images. The images show four different polystyrene microfluidic channels analogous to that shown in FIG. 6. Each channel was used of one of four different conditions under investigation: 1) Media control, 2) uniform chemoattractant, 3) chemo-attractant gradient and 4) chemo-attractant gradient with inhibitor. For conditions 1 and 3 each channel network was wick-filled with EGM2MV cell culture media via the source input port. For condition 2 the channel network was wick-filled with EGM2MV cell culture media containing 10 nM formyl-Met-Leu-Phe (fMLP, Sigma-Aldrich). For condition 4 the channel network was wick-filled with EGM2MV cell culture media containing 5 μM Latrunculin B (Sigma-Aldrich). Next, for conditions 3 and 4, a 1.2 μL drop of 1 μM fMLP was added to the source input using a handheld pipette. For condition 4 the fMLP solution also contained Latrunculin B at the same concentration as the media to ensure a uniform concentration of the inhibitor during the study. This volume flowed into the source volume via passive pumping. Lastly, for all four conditions, a 1.5 μL drop of freshly isolated primary neutrophils at roughly at a concentration of roughly 5,000 cells/μL were added to the cell addition port. The photo-micrographs indicate the paths along which cells migrate over 52 minutes under the above conditions.
Figure 11:
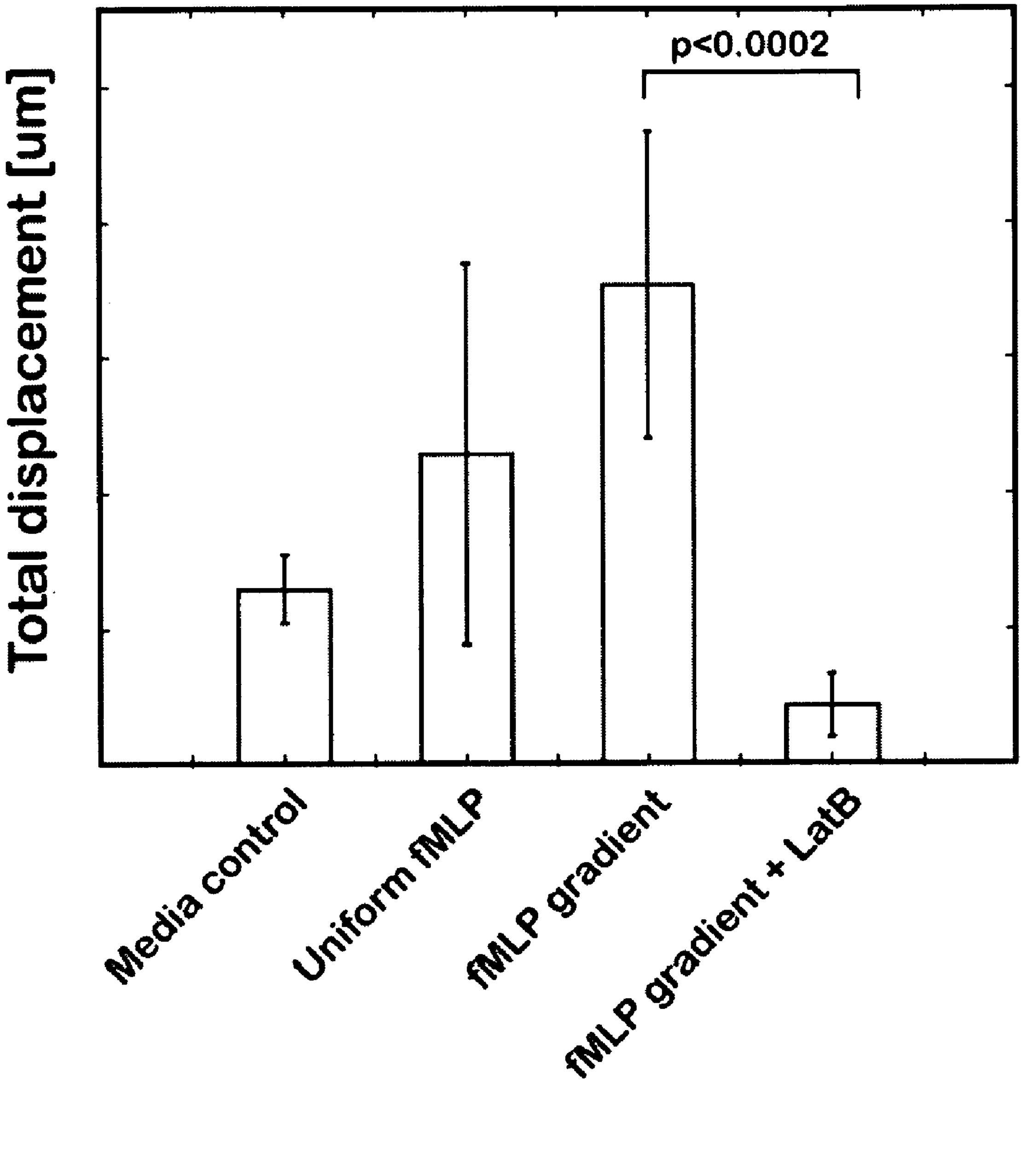
FIG. 11 shows the mean total displacement of cells tracked over a period of 52 minutes under the four different conditions listed under the description of FIG. 10 above. The standard deviation for different cells is indicated by the error bars. Cells were found to migrate further in the presence of uniform fMLP concentration compared to absence of fMLP. Cell migrated further still in the presence of an fMLP gradient, but migration up an fMLP gradient was strongly inhibited in the presence of Latrunculin B. The difference between cells responding to an fMLP gradient, to that of cells responding to an fMLP gradient in the presence of Latrunculin B was found to be significant as assessed by the student's T-test.
Figure 12A:
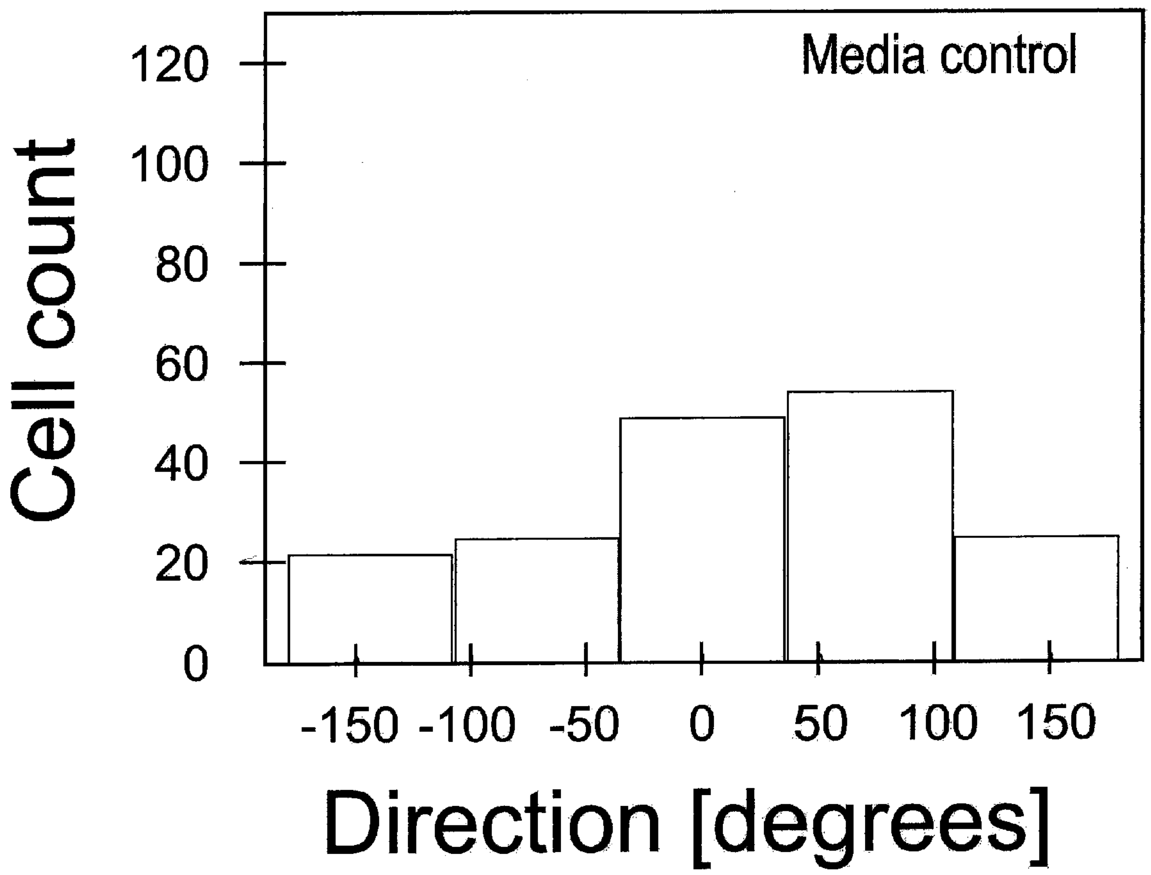
FIG. 12 Shows the direction of displacement vectors for cells tracked over a period of 52 minutes under the four different conditions listed under the description of FIG. 10 above. The direction of 0 degrees was oriented directly up the gradient channel. The plots were scaled in proportion to number of cells tracked. The analysis indicates a slight preference for migrating up the channel in the presence of uniform fMLP concentration compared to absence of fMLP. In the presence of an fMLP gradient cells exhibited a strong preference for migrating in the direction of increasing concentration of the gradient, but this preference was abolished in the presence of Latrunculin B.
Figure 12B:
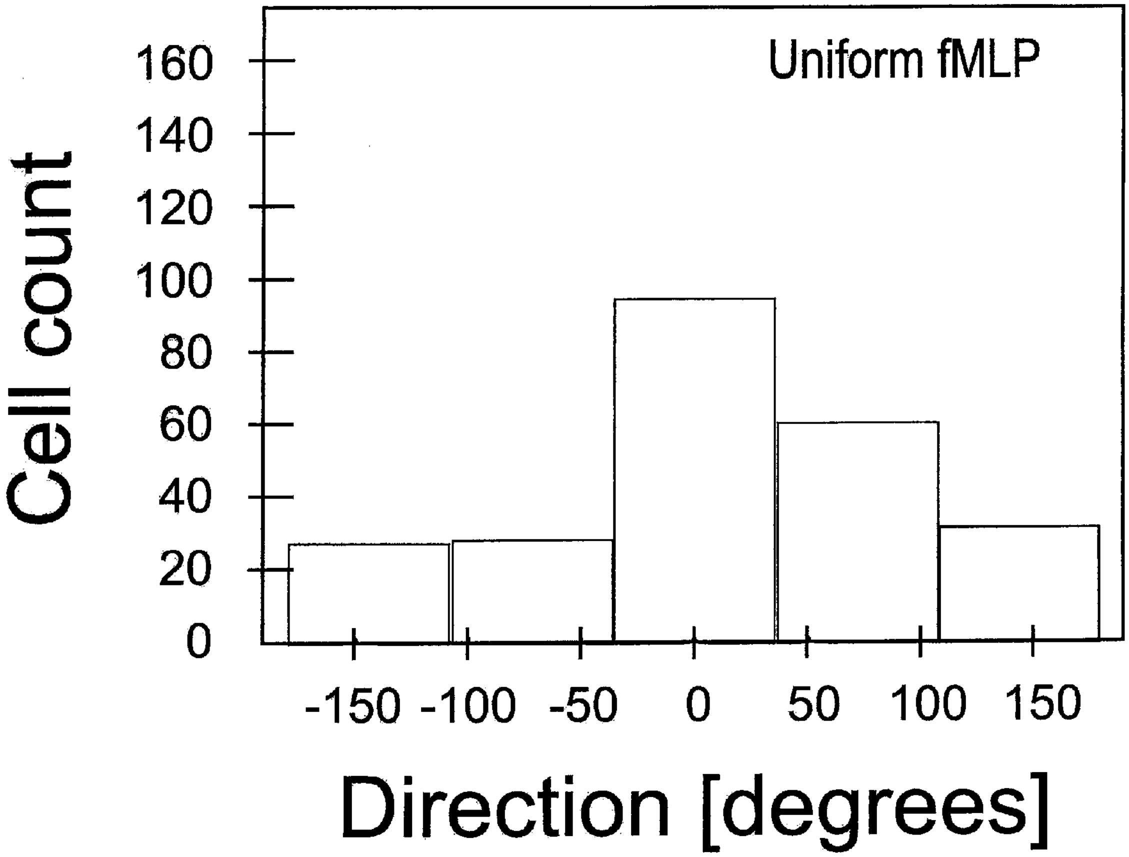
Figure 12C:
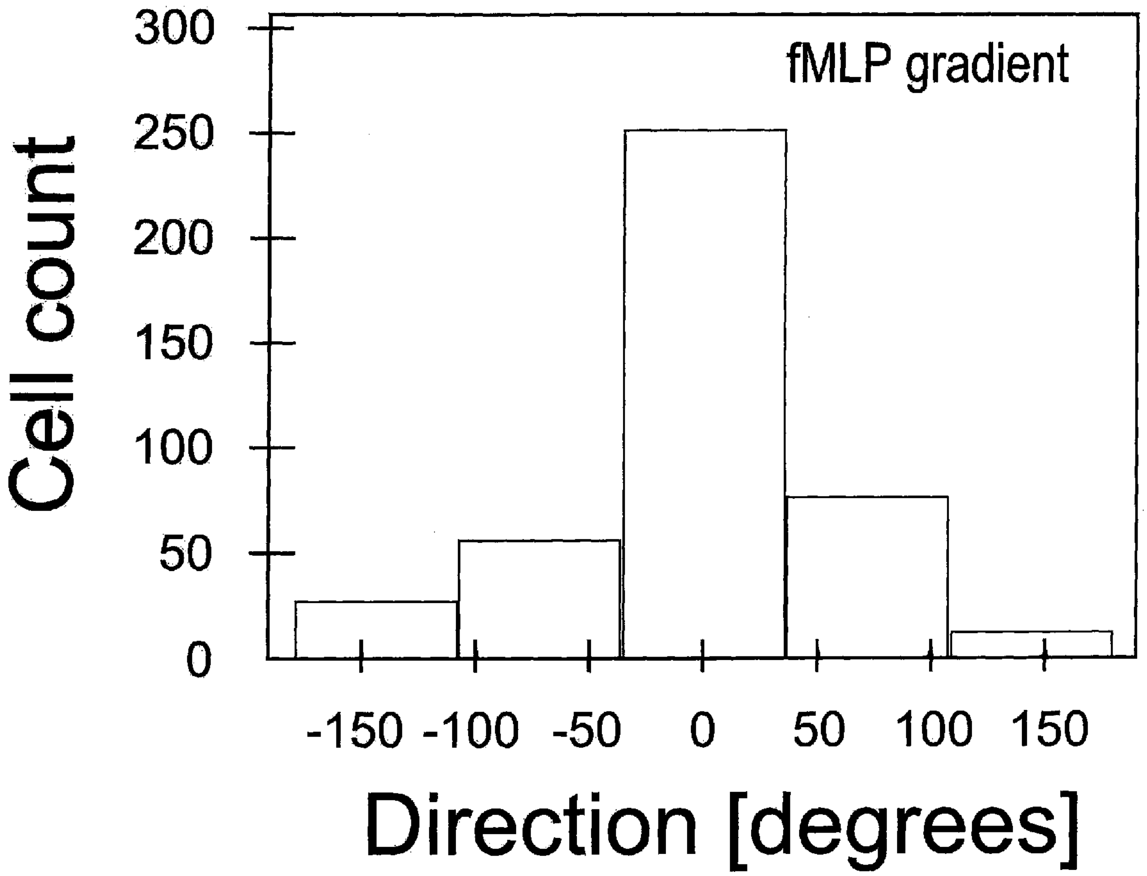
Figure 12D:
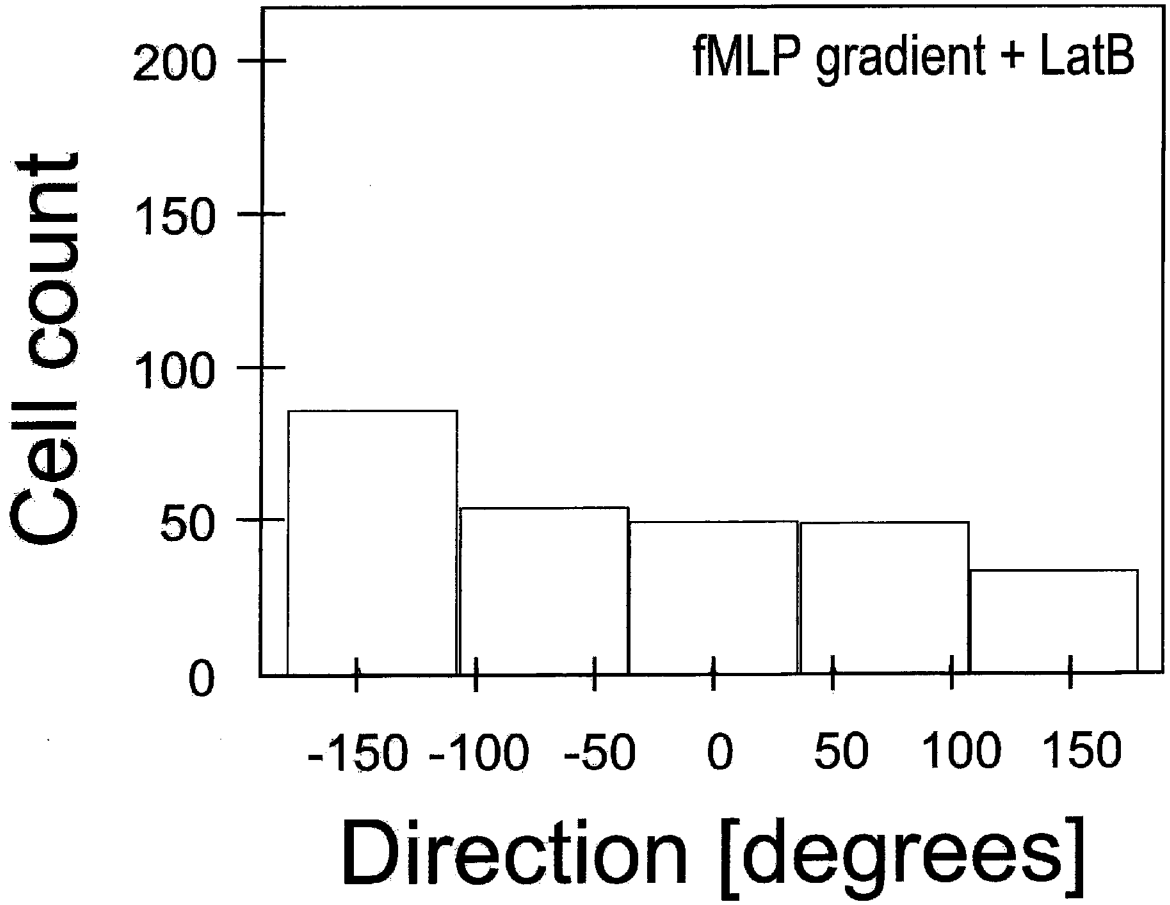

Human neutrophil cell culture media and chemo-attractant solution were prepared using conventional protocols. (See, Nuzzi P A at al., Analysis of neutrophil chemotaxis, *Methods in Molecular Biology* 370:23-26, 2007). Primary human neutrophils were acquired from donors under approved protocol. (See University of Wisconsin Institutional Review Board and National Institutes of Health Protection concerning protection of human subjects regulations). Four channel networks in a polystyrene device were prepared. Each channel was used to test one of four different conditions: 1) Media control, 2) uniform chemo-attractant, 3) chemo-attractant gradient and 4) chemo-attractant gradient with inhibitor. For conditions 1 and 3 each channel network was wick-filled with EGM2MV cell culture media via the source input port. For condition 2 the channel network was wick-filled with EGM2MV cell culture media containing 10 nM formyl-Met-Leu-Phe (fMLP, Sigma-Aldrich). For condition 4 the channel network was wick-filled with EGM2MV cell culture media containing 5 μM Latrunculin B (Sigma-Aldrich). Next, for conditions 3 and 4, a 1.2 μL drop of 1 μM fMLP was added to the source input using a handheld pipette. For condition 4 the fMLP solution also contained Latrunculin B at the same concentration as the media to ensure a uniform concentration of the inhibitor during the study. This volume flowed into the source volume via passive pumping. Lastly, for all four conditions, a 1.5 μL drop of freshly isolated primary neutrophils at roughly at a concentration of roughly 5,000 cells/μL were added to the cell addition port. The cells are visible as dark features in FIG. 10, and data representing analysis of cell tracking results are shown in FIGS. 11 and 12.

The cells that were seeded in the device loaded with a chemo-attractant showed significant migration into the gradient channel. Thus, formation of chemoattractant gradient was demonstrated Cell movement in the channel geometry in response to the gradient was also demonstrated.

The disclosure of every patent, patent application, and publication cited herein is hereby incorporated herein by reference in its entirety.

It is understood that certain adaptations of the invention described in this disclosure are a matter of routine optimization for those skilled in the art, and can be implemented without departing from the spirit of the invention, or the scope of the appended claims.

We claim:

1. A microfluidic gradient device comprising:

a source assembly adapted to contain a source liquid volume in the range of 25 pL to 15 μL defining a source assembly air/liquid interface having a source assembly radius of curvature comprising a source port having a source port area and source port perimeter in fluid communication with a source reservoir;

a sink assembly adapted to contain a sink liquid volume in the range of 500 pL to 100 μL defining a sink assembly air/liquid interface having a sink assembly radius of curvature comprising a sink port having a sink port area and a sink port perimeter in fluid communication with a sink reservoir;

a gradient channel adapted to contain a gradient fluid volume in the range of 500 fL to 6 μL, the gradient channel having a gradient height, gradient width, gradient length, gradient transverse cross-sectional area, gradient flow resistance in the range of $1\times10^8$ to $1\times10^{18}$ N-s-m$^{-5}$, and, gradient contact angle, the gradient channel in fluid communication with the source reservoir and sink reservoir; and a closed circuit channel adapted to contain a circuit liquid volume in the range of 50 pL to 400 μL, the closed circuit channel having a circuit height, circuit width, circuit length, circuit transverse cross-sectional area, circuit flow resistance in the range of $1\times10^6$ to $1\times10^{15}$ N-s-m$^{-5}$, and, circuit contact angle, the closed circuit channel in fluid communication with the source reservoir and sink reservoir, wherein the ratio (gradient flow resistance):(circuit flow resistance) is in the range of (10-10,000):1.

2. The microfluidic gradient device of claim 1, wherein the gradient height is in the range of 1 μm to 200 μm, wherein the gradient width is in the range of 10 μm to 3 mm, wherein the gradient length is in the range of 50 μm to 10 mm, wherein circuit height is in the range of 10 μm to 2 mm, wherein the circuit width is in the range of 50 μm to 4 mm, wherein the circuit length is in the range of 100 μm to 50 mm, wherein the gradient transverse cross-sectional area is in the range of 10 μm$^2$ to $6\times10^5$ μm$^2$, wherein the circuit transverse cross-sectional area is in the range of 500 μm$^2$ to $8\times10^6$ μm$^2$, wherein the source port area is in the range of 900 μm$^2$ to 9 mm$^2$, and wherein the sink port area is in the range of 2500 μm$^2$ to 81 mm$^2$.

3. The microfluidic gradient device of claim 1, useful for chemotaxis assays, wherein the gradient height is in the range of 15 μm to 200 μm, wherein the gradient width is in the range of 100 μm to 3 mm, wherein the gradient length is in the range of 500 μm to 4 mm, wherein circuit height is in the range of 100 μm to 2 mm, wherein the circuit width is in the range of 500 μm to 4 mm, wherein the circuit length is in the range of 3 mm to 30 mm, wherein the gradient transverse cross-sectional area is in the range of 1500 μm$^2$ to $6\times10^5$ μm$^2$, wherein the circuit transverse cross-sectional area is in the range of $1\times10^5$ μm$^2$ to $8\times10^6$ μm$^2$, wherein the source port area is in the range of 2500 μm$^2$ to 9 mm$^2$, and wherein the sink port area is in the range of $1\times10^4$ μm$^2$ to 81 mm$^2$.

4. The microfluidic gradient device of claim 1, wherein gradient height is around 25 μm, wherein the gradient width is around 1 mm, wherein the gradient length is around 3 mm, wherein circuit height is around 250 μm, wherein the circuit width is around 1 mm, wherein the circuit length is around 20 mm, wherein the gradient transverse cross-sectional area is around $2.5\times10^4$ μm$^2$, wherein the circuit transverse cross-sectional area is around $2.5\times10^5$ μm$^2$, wherein the ratio of the (gradient flow resistance):(circuit flow resistance) is around 200:1, wherein the gradient liquid volume is around 75 nL, wherein the circuit liquid volume is around 5 μL, wherein the gradient flow resistance is around $2\times10^{12}$ N-s-m$^{-5}$, wherein the circuit flow resistance is around $1\times10^{10}$ N-s-m$^{-5}$, wherein the source liquid volume is around 0.5 μL, wherein the sink liquid volume is around 16 μL, wherein the source port area is around 0.8 mm$^2$, and, wherein the sink port area is around 2 mm$^2$.

5. The microfluidic gradient device of any one of claims 1-4, wherein the inner surface of the gradient channel has a gradient contact angle in the range of 0° to 60°, and wherein the inner surface of the closed-circuit channel has a closed-circuit contact angle in the range of 0° to 60°.

6. The microfluidic gradient device of any one of claims 1-4, wherein the source port radius of curvature and the sink port radius of curvature are equal when gradient and circuit liquid volumes are in flow equilibrium.

7. The microfluidic gradient device of any one of claims 1-4, wherein the transverse cross-sectional shape of the gradient channel is rectangular or curvalinear, wherein the longitudinal cross-sectional shape of the gradient channel is rectangular or curvalinear, wherein the transverse cross-sectional shape of the closed circuit channel is rectangular or curvalinear, and wherein the longitudinal cross-sectional shape of the closed circuit channel is rectangular or curvalinear.

8. The microfluidic gradient device of any of claims 1-4, wherein the shape of the source port perimeter is rectangular, polygonal or curvilinear, and wherein the shape of the sink port perimeter is rectangular, polygonal or curvilinear.

9. The microfluidic gradient device of any one of claims 1-4, constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

10. The microfluidic gradient device of any one of claims 1-4, wherein the sink assembly further comprises an air vent port, having an air vent port area in the range of 900 μm$^2$ to 9 mm$^2$, and where the air vent port is connected to the sink reservoir.

11. A microfluidic gradient device comprising:

a source assembly adapted to contain a source liquid volume in the range of 25 pL to 15 μL defining a source assembly air/liquid interface having a source assembly radius of curvature comprising a source port having a source port area and source port perimeter in fluid communication with a source reservoir;

a sink assembly adapted to contain a sink liquid volume in the range of 500 pL to 100 μL defining a sink assembly air/liquid interface having a sink assembly radius of curvature comprising a sink port having a sink port area and sink port perimeter in fluid communication with a sink reservoir;

a cell addition assembly adapted to contain a cell addition assembly liquid volume defining a cell addition assembly air/liquid interface having a cell addition assembly radius of curvature comprising a cell addition port having a cell addition port area and a cell addition port perimeter in fluid communication with a cell addition reservoir, the cell addition reservoir in fluid communication with the sink reservoir;

a gradient channel adapted to contain a gradient liquid volume in the range of 500 fL to 6 μL having a gradient height, gradient width, gradient length, gradient transverse cross-sectional area, gradient flow resistance in the range of $1\times10^{8}$ to $1\times10^{18}$ N-s-m$^{-5}$, and, gradient contact angle, the gradient channel in fluid communication with the source reservoir and sink reservoir; and a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-m$^{-5}$, and, circuit contact angle, the closed circuit channel in fluid communication with the source reservoir and sink reservoir, wherein the ratio (gradient flow resistance):(circuit flow resistance) is in the range of (10-10,000):1.

12. The microfluidic gradient device of claim 11, wherein the gradient height is in the range of 1 μm to 200 μm, wherein the gradient width is in the range of 10 μm to 3 mm, wherein the gradient length is in the range of 50 μm to 10 mm, wherein circuit height is in the range of 10 μm to 2 mm, wherein the circuit width is in the range of 50 μm to 4 mm, wherein the circuit length is in the range of 100 μm to 50 mm, wherein the gradient transverse cross-sectional area is in the range of 10 μm$^2$ to $6\times10^{5}$ μm$^2$, wherein the circuit transverse cross-sectional area is in the range of 500 μm$^2$ to $8\times10^{6}$ μm$^2$, wherein the source port area is in the range of 900 μm$^2$ to 9 mm$^2$, wherein the sink port area is in the range of 2500 μm$^2$ to 81 mm$^2$, and wherein the cell addition port area is in the range of 900 μm$^2$ to 9 mm$^2$.

13. The microfluidic gradient device of claim 11, useful for chemotaxis assays, wherein the gradient height is in the range of 15 μm to 200 μm, wherein the gradient width is in the range of 100 μm to 3 mm, wherein the gradient length is in the range of 500 μm to 4 mm, wherein circuit height is in the range of 100 μm to 2 mm, wherein the circuit width is in the range of 500 μm to 4 mm, wherein the circuit length is in the range of 3 mm to 30 mm, wherein the gradient transverse cross-sectional area is in the range of 1500 μm$^2$ to $6\times10^{5}$ μm$^2$, wherein the circuit transverse cross-sectional area is in the range of $1\times10^{5}$ μm$^2$ to $8\times10^{6}$ μm$^2$, wherein the source port area is in the range of 2500 μm$^2$ to 9 mm$^2$, wherein the sink port area is in the range of $1\times10^{4}$ μm$^2$ to 81 mm$^2$, and wherein the cell addition port area is in the range of 2500 μm$^2$ to 9 mm$^2$.

14. The microfluidic gradient device of claim 11, wherein gradient height is around 50 μm, wherein the gradient width is around 1 mm, wherein the gradient length is around 3.5 mm, wherein circuit height is around 1 mm, wherein the circuit width is around 1 mm, wherein the circuit length is around 6 mm, wherein the gradient transverse cross-sectional area is around $5\times10^{4}$ μm$^2$, wherein the circuit transverse cross-sectional area is around $1\times10^{6}$ μm$^2$, wherein the ratio of the (gradient flow resistance):(circuit flow resistance) is around 5000:1, wherein the gradient liquid volume is around 175 nL, wherein the circuit liquid volume is around 6 μL, wherein the gradient flow resistance is around $3.5\times10^{11}$ N-s-m$^{-5}$, wherein the circuit flow resistance is around $7\times10^{7}$ N-s-m$^{-5}$, wherein the source liquid volume is around 1.5 μL, wherein the sink liquid volume is around 11 μL, wherein the source port area is around 0.8 mm$^2$, wherein the sink port area is around 3 mm$^2$, and, wherein the cell addition port area is around 0.8 mm$^2$.

15. The microfluidic gradient device of any one of claims 11-14, wherein the inner surface of the gradient channel has a gradient contact angle in the range of 0° to 60°, and wherein the inner surface of the closed-circuit channel has a closed-circuit contact angle in the range of 0° to 60°.

16. The microfluidic gradient device of any one of claims 11-14, wherein the source port radius of curvature, the cell addition port radius of curvature, and the sink port radius of curvature are equal when gradient and circuit liquid volumes are in flow equilibrium.

17. The microfluidic gradient device of any one of claims 11-14, wherein the transverse cross-sectional shape of the gradient channel is rectangular or curvalinear, wherein the longitudinal cross-sectional shape of the gradient channel is rectangular or curvalinear, wherein the transverse cross-sectional shape of the closed circuit channel is rectangular or curvalinear, and wherein the longitudinal cross-sectional shape of the closed circuit channel is rectangular or curvalinear.

18. The microfluidic gradient device of any of claims 11-14, wherein the shape of the source port perimeter is rectangular, polygonal or curvilinear, wherein the shape of the cell addition port perimeter is rectangular, polygonal or curvilinear, and wherein the shape of the sink port perimeter is rectangular, polygonal or curvilinear.

19. The microfluidic gradient device of any one of claims 11-14, constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

20. The microfluidic gradient device of any one of claims 11-14, wherein the sink assembly further comprises an air vent port, having an air vent port area in the range of 900 μm$^2$ to 9 mm$^2$, and where the air vent port is connected to the sink reservoir.

21. A microfluidic gradient device comprising:

a source assembly adapted to contain a source liquid volume in the range of 25 pL to 15 μL defining a source assembly air/liquid interface having a source assembly radius of curvature comprising a source port having a source port area and source port perimeter in fluid communication with a source reservoir;

a sink assembly adapted to contain a sink liquid volume in the range of 500 pL to 100 μL defining a sink assembly air/liquid interface having a sink assembly radius of curvature comprising a sink port having a sink port area and sink port perimeter in fluid communication with a sink reservoir;

a gradient channel adapted to contain a gradient liquid volume in the range of 25 pL to 6 μL having a gradient height, gradient width, gradient length, gradient transverse cross-sectional area, gradient flow resistance in the range of $1\times10^{18}$ to $1\times10^{18}$ N-s-m$^{-5}$, and, gradient contact angle, the gradient channel in fluid communication with the source reservoir and sink reservoir;

a cell addition assembly adapted to contain a cell addition assembly liquid volume defining a cell addition assembly air/liquid interface having a cell addition assembly radius of curvature comprising a cell addition port having a cell addition port area and a cell addition port perimeter in fluid communication with a cell addition reservoir, the cell addition reservoir in fluid communication with the gradient channel; and a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-m$^{-5}$, and, circuit contact angle, the closed circuit channel in fluid communication with the source reservoir and sink reservoir, wherein the ratio (gradient flow resistance):(circuit flow resistance) is in the range of (10-10,000):1.

22. The microfluidic gradient device of claim 21, wherein the gradient height is in the range of 1 μm to 200 μm, wherein the gradient width is in the range of 10 μm to 3 mm, wherein the gradient length is in the range of 50 μm to 10 mm, wherein the circuit height is in the range of 10 μm to 2 mm, wherein the circuit width is in the range of 50 μm to 4 mm, wherein the circuit length is in the range of 100 μm to 50 mm, wherein the gradient transverse cross-sectional area is in the range of 10 μm$^2$ to $6\times10^{5}$ μm$^2$, wherein the circuit transverse cross-sectional area is in the range of 500 μm$^2$ to $8\times10^{6}$ μm$^2$, wherein the source port area is in the range of 900 μm$^2$ to 9 mm$^2$, wherein the sink port area is in the range of 2500 μm$^2$ to 81 mm$^2$, and wherein the cell addition port area is in the range of 900 μm$^2$ to 9 mm$^2$.

23. The microfluidic gradient device of claim 21, useful for chemotaxis assays, wherein the gradient height is in the range of 15 μm to 200 μm, wherein the gradient width is in the range of 100 μm to 3 mm, wherein the gradient length is in the range of 500 μm to 4 mm, wherein circuit height is in the range of 100 μm to 2 mm, wherein the circuit width is in the range of 500 μm to 4 mm, wherein the circuit length is in the range of 3 mm to 30 mm, wherein the gradient transverse cross-sectional area is in the range of 1500 μm$^2$ to $6\times10^{5}$ μm$^2$, wherein the circuit transverse cross-sectional area is in the range of $1\times10^{5}$ μm$^2$ to $8\times10^{6}$ μm$^2$, wherein the source port area is in the range of 2500 μm$^2$ to 9 mm$^2$, wherein the sink port area is in the range of $1\times10^{4}$ μm$^2$ to 81 mm$^2$, and wherein the cell addition port area is in the range of 2500 μm$^2$ to 9 mm$^2$.

24. The microfluidic gradient device of any one of claims 21-23, wherein the transverse cross-sectional shape of the gradient channel is rectangular or curvalinear, wherein the longitudinal cross-sectional shape of the gradient channel is rectangular or curvalinear, wherein the transverse cross-sectional shape of the closed circuit channel is rectangular or curvalinear, and wherein the longitudinal cross-sectional shape of the closed circuit channel is rectangular or curvalinear.

25. The microfluidic gradient device of any of claims 21-23, wherein the shape of the source port perimeter is rectangular, polygonal or curvilinear, wherein the shape of the cell addition port perimeter is rectangular, polygonal or curvilinear, and wherein the shape of the sink port perimeter is rectangular, polygonal or curvilinear.

26. A microfluidic gradient device comprising:

a source assembly adapted to contain a source liquid volume in the range of 25 pL to 15 μL defining a source assembly air/liquid interface having a source assembly radius of curvature comprising a source port having a source port area and source port perimeter in fluid communication with a source reservoir;

a sink assembly adapted to contain a sink liquid volume in the range of 500 pL to 100 μL defining a sink assembly air/liquid interface having a sink assembly radius of curvature comprising a sink port having a sink port area and sink port perimeter in fluid communication with a sink reservoir;

a gradient channel adapted to contain a gradient liquid volume in the range of 500 fL to 6 μL having a gradient height, gradient width, gradient length, gradient transverse cross-sectional area, gradient flow resistance in the range of $1\times10^{8}$ to $1\times10^{18}$ N-s-m$^{-5}$, and, gradient contact angle, the gradient channel in fluid communication with the source reservoir and sink reservoir;

a closed circuit channel adapted to contain a circuit liquid volume in the range of 50 pL to 400 μL having a circuit height, circuit width, circuit length, circuit transverse cross-sectional area, circuit flow resistance in the range of $1\times10^{6}$ to $1\times10^{15}$ N-s-m$^{-5}$, and, circuit contact angle, the closed circuit channel in fluid communication with the source reservoir and sink reservoir; and a cell seeding assembly adapted to contain a cell seeding assembly liquid volume in the range of 30 pL to 65 μL defining a cell seeding assembly air/liquid interface having a cell seeding assembly radius of curvature comprising:

a cell addition port having a cell addition port area and a cell addition port perimeter in fluid communication with a cell addition reservoir in fluid communication with a cell addition channel in fluid communication with the gradient channel having a cell addition height, cell addition width, cell addition length, cell addition transverse cross-sectional area, and, cell addition flow resistance in the range of $5\times10^{6}$ to $6\times10^{13}$ N-s-m$^{-5}$, wherein the ratio (gradient flow resistance):(circuit flow resistance) is in the range of (10-10,000):1.

27. The microfluidic gradient device of claim 26, wherein the gradient height is in the range of 1 μm to 200 μm, wherein the gradient width is in the range of 10 μm to 3 mm, wherein the gradient length is in the range of 50 μm to 10 mm, wherein circuit height is in the range of 10 μm to 2 mm, wherein the circuit width is in the range of 50 μm to 4 mm, wherein the circuit length is in the range of 100 μm to 50 mm, wherein the cell addition height is in the range of 10 μm to 2 mm, wherein the cell addition width is in the range of 10 μm to 3 mm, wherein the cell addition length is in the range of 50 μm to 10 mm, wherein the gradient transverse cross-sectional area is in the range of 10 μm$^2$ to $6\times10^{5}$ μm$^2$, wherein the circuit transverse cross-sectional area is in the range of 500 μm$^2$ to $8\times10^{6}$ μm$^2$, wherein the cell addition transverse cross-sectional area is in the range of 100 μm$^2$ to $6\times10^{6}$ μm$^2$, wherein the source port area is in the range of 900 μm$^2$ to 9 mm$^2$, wherein the sink port area is in the range of 2500 μm$^2$ to 81 mm$^2$, and wherein the cell addition port area is in the range of 900 μm$^2$ to 9 mm$^2$.

28. The microfluidic gradient device of claim 26, useful for chemotaxis assays, wherein the gradient height is in the range of 15 μm to 200 μm, wherein the gradient width is in the range of 100 μm to 3 mm, wherein the gradient length is in the range of 500 μm to 4 mm, wherein circuit height is in the range of 100 μm to 2 mm, wherein the circuit width is in the range of 500 μm to 4 mm, wherein the circuit length is in the range of 3 mm to 30 mm, wherein the cell addition height is in the range of 100 μm to 2 mm, wherein the cell addition width is in the range of 100 μm to 3 mm, wherein the cell addition length is in the range of 500 μm to 4 mm, wherein the gradient transverse cross-sectional area is in the range of 1500 μm$^2$ to $6\times10^{5}$ μm$^2$, wherein the circuit transverse cross-sectional area is in the range of $1\times10^{5}$ μm$^2$ to $8\times10^{6}$ μm$^2$, wherein the cell addition transverse cross-sectional area is in the range of $2\times10^{4}$ μm$^2$ to $6\times10^{6}$ μm$^2$, wherein the source port area is in the range of 2500 μm$^2$ to 9 mm$^2$, wherein the sink port area is in the range of $1\times10^{4}$ μm$^2$ to 81 mm$^2$, and wherein the cell addition port area is in the range of 2500 μm$^2$ to 9 mm$^2$.

29. A microfluidic gradient device comprising:

a source assembly adapted to contain a source liquid volume in the range of 75 pL to 110 μL defining a source assembly air/liquid interface having a source assembly radius of curvature comprising:

a source port having a source port area and source port perimeter in fluid communication with a source input reservoir;

a source auxiliary channel in fluid communication with the source input reservoir and a source reservoir having an auxiliary height, auxiliary width, auxiliary length, auxiliary transverse cross-sectional area, auxiliary flow resistance in the range of $1\times10^6$ to $1\times10^{15}$ N-s-$m^{-5}$, and, auxiliary contact angle;

a sink assembly adapted to contain a sink liquid volume in the range of 500 pL to 100 μL defining a sink assembly air/liquid interface having a sink assembly radius of curvature comprising a sink port having a sink port area and sink port perimeter in fluid communication with a sink reservoir;

a gradient channel adapted to contain a gradient liquid volume in the range of 500 fL to 6 μL having a gradient height, gradient width, gradient length, gradient transverse cross-sectional area, gradient flow resistance in the range of $1\times10^8$ to $1\times10^{18}$ N-s-$m^{-5}$, and, gradient contact angle, the gradient channel in fluid communication with the source reservoir and sink reservoir; and a closed circuit channel adapted to contain a circuit liquid volume in the range of 50 pL to 400 μL having a circuit height, circuit width, circuit length, circuit transverse cross-sectional area, circuit flow resistance in the range of $1\times10^6$ to $1\times10^{15}$ N-s-$m^{-5}$, and, circuit contact angle, the closed circuit channel in fluid communication with the source reservoir and sink reservoir, wherein the ratio (gradient flow resistance):(circuit flow resistance) is in the range of (10-10,000):1.

30. The microfluidic gradient device of claim 29, wherein the gradient height is in the range of 1 μm to 200 μm, wherein the gradient width is in the range of 10 μm to 3 mm, wherein the gradient length is in the range of 50 μm to 10 mm, wherein circuit height is in the range of 10 μm to 2 mm, wherein the circuit width is in the range of 50 μm to 4 mm, wherein the circuit length is in the range of 100 μm to 50 mm, wherein the auxiliary height is in the range of 10 μm to 2 mm, wherein the auxiliary width is in the range of 50 μm to 4 mm, wherein the auxiliary length is in the range of 50 μm to 10 mm, wherein the gradient transverse cross-sectional area is in the range of 10 $\mu m^2$ to $6\times10^5$ $\mu m^2$, wherein the circuit transverse cross-sectional area is in the range of 500 $\mu m^2$ to $8\times10^6$ $\mu m^2$, wherein the auxiliary transverse cross-sectional area is in the range of 500 $\mu m^2$ to $8\times10^6$ $\mu m^2$, wherein the source port area is in the range of 900 $\mu m^2$ to 9 $mm^2$, and wherein the sink port area is in the range of 2500 $\mu m^2$ to 81 $mm^2$.

31. The microfluidic gradient device of claim 29, useful for chemotaxis assays, wherein the gradient height is in the range of 15 μm to 200 μm, wherein the gradient width is in the range of 100 μm to 3 mm, wherein the gradient length is in the range of 500 μm to 4 mm, wherein circuit height is in the range of 100 μm to 2 mm, wherein the circuit width is in the range of 500 μm to 4 mm, wherein the circuit length is in the range of 3 mm to 30 mm, wherein the auxiliary height is in the range of 100 μm to 2 mm, wherein the auxiliary width is in the range of 500 μm to 4 mm, wherein the auxiliary length is in the range of 500 μm to 5 mm, wherein the gradient transverse cross-sectional area is in the range of 1500 $\mu m^2$ to $6\times10^5$ $\mu m^2$, wherein the circuit transverse cross-sectional area is in the range of $1\times10^5$ $\mu m^2$ to $8\times10^6$ $\mu m^2$, wherein the auxiliary transverse cross-sectional area is in the range of $5\times10^4$ $\mu m^2$ to $8\times10^6$ $\mu m^2$, wherein the source port area is in the range of 2500 $\mu m^2$ to 9 $mm^2$, and wherein the sink port area is in the range of $1\times10^4$ $\mu m^2$ to 81 $mm^2$.

32. The microfluidic gradient device of claim 29, wherein the gradient height is around 100 μm, wherein the gradient width is around 2 mm, wherein the gradient length is around 1 mm, wherein the circuit height is around 1 mm, wherein the circuit width is around 1 mm, wherein the circuit length is around 9 mm, wherein the auxiliary height is around 100 μm, wherein the auxiliary width is around 1 mm, wherein the auxiliary length is around 3 mm, wherein the gradient transverse cross-sectional area is around $2\times10^5$ $\mu m^2$, wherein the circuit transverse cross-sectional area is around $1\times10^6$ $\mu m^2$, wherein the auxiliary transverse cross-sectional area is around $1\times10^5$ $\mu m^2$, wherein the ratio of the (gradient flow resistance):(circuit flow resistance) is around 60:1, wherein the gradient liquid volume is around 200 nL, wherein the circuit liquid volume is around 9 μL, wherein the auxiliary liquid volume is around 300 nL, wherein the gradient flow resistance is around $6\times10^9$ N-s-$m^{-5}$, wherein the circuit flow resistance is around $1\times10^8$ N-s-$m^{-5}$, wherein the auxiliary flow resistance is around $3\times10^{10}$ N-s-$m^{-5}$, wherein the source liquid volume is around 3 μL, wherein the sink liquid volume is around 15 μL, wherein the source input liquid volume is around 1.6 μL, wherein the source port area is around 0.8 $mm^2$, and, wherein the sink port area is around 2 $mm^2$.

33. The microfluidic gradient device of any one of claims 29-32, wherein the inner surface of the gradient channel has a gradient contact angle in the range of 0° to 60°, wherein the inner surface of the closed-circuit channel has a closed-circuit contact angle in the range of 0° to 60°, and wherein the inner surface of the auxiliary channel has a gradient contact angle in the range of 0° to 60°.

34. The microfluidic gradient device of any one of claims 29-32, wherein the source port radius of curvature and the sink port radius of curvature are equal when gradient, circuit, and auxiliary liquid volumes are in flow equilibrium.

35. The microfluidic gradient device of any one of claims 29-32, wherein the transverse cross-sectional shape of the gradient channel is rectangular or curvalinear, wherein the longitudinal cross-sectional shape of the gradient channel is rectangular or curvalinear, wherein the transverse cross-sectional shape of the closed circuit channel is rectangular or curvalinear, wherein the longitudinal cross-sectional shape of the closed circuit channel is rectangular or curvalinear, and wherein the transverse cross-sectional shape of the auxiliary channel is rectangular or curvalinear, wherein the longitudinal cross-sectional shape of the auxiliary channel is rectangular or curvalinear.

36. The microfluidic gradient device of any of claims 29-32, wherein the shape of the source port perimeter is rectangular, polygonal or curvilinear, and wherein the shape of the sink port perimeter is rectangular, polygonal or curvilinear.

37. The microfluidic gradient device of any one of claims 29-32, constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

38. The microfluidic gradient device of any one of claims 29-32, wherein the sink assembly further comprises an air vent port, having an air vent port area in the range of 900 $\mu m^2$ to 9 $mm^2$, and where the air vent port is connected to the sink reservoir.

39. A microfluidic gradient device comprising:

a source assembly adapted to contain a source liquid volume in the range of 75 pL to 110 μL defining a source assembly air/liquid interface having a source assembly radius of curvature comprising:

a source port having a source port area and source port perimeter in fluid communication with a source input reservoir;

a source auxiliary channel in fluid communication with the source input reservoir and a source reservoir having an auxiliary height, auxiliary width, auxiliary length, auxiliary transverse cross-sectional area, auxiliary flow resistance in the range of $1\times10^6$ to $1\times10^{15}$ N-s-m$^{-5}$, and, auxiliary contact angle;

a sink assembly adapted to contain a sink liquid volume in the range of 500 pL to 100 μL defining a sink assembly air/liquid interface having a sink assembly radius of curvature comprising a sink port having a sink port area and a sink port perimeter in fluid communication with a sink reservoir;

a cell addition assembly adapted to contain a cell addition assembly fluid defining a cell addition assembly air/liquid interface having a cell addition assembly radius of curvature comprising a cell addition port having a cell addition port area and a cell addition port perimeter in fluid communication with a cell addition reservoir in fluid communication with the sink reservoir;

a gradient channel adapted to contain a gradient liquid volume in the range of 500 fL to 6 μL having a gradient height, gradient width, gradient length, gradient transverse cross-sectional area, gradient flow resistance in the range of $1\times10^8$ to $1\times10^{18}$ N-s-m$^{-5}$, and, gradient contact angle, the gradient channel in fluid communication with the source reservoir and sink reservoir; and a closed circuit channel adapted to contain a circuit liquid volume in the range of 50 pL to 400 μL having a circuit height, circuit width, circuit length, circuit transverse cross-sectional area, circuit flow resistance in the range of $1\times10^6$ to $1\times10^{15}$ N-s-m$^{-5}$, and, circuit contact angle, the closed circuit channel in fluid communication with the source reservoir and sink reservoir, wherein the ratio (gradient flow resistance):(circuit flow resistance) is in the range of (10-10,000):1.

40. The microfluidic gradient device of claim 39, wherein the gradient height is in the range of 1 μm to 200 μm, wherein the gradient width is in the range of 10 μm to 3 mm, wherein the gradient length is in the range of 50 μm to 10 mm, wherein circuit height is in the range of 10 μm to 2 mm, wherein the circuit width is in the range of 50 μm to 4 mm, wherein the circuit length is in the range of 100 μm to 50 mm, wherein the auxiliary height is in the range of 10 μm to 2 mm, wherein the auxiliary width is in the range of 50 μm to 4 mm, wherein the auxiliary length is in the range of 50 μm to 10 mm, wherein the gradient transverse cross-sectional area is in the range of 10 μm$^2$ to $6\times10^5$ μm$^2$, wherein the circuit transverse cross-sectional area is in the range of 500 μm$^2$ to $8\times10^6$ μm$^2$, wherein the auxiliary transverse cross-sectional area is in the range of 500 μm$^2$ to $8\times10^6$ μm$^2$, wherein the source port area is in the range of 900 μm$^2$ to 9 mm$^2$, wherein the sink port area is in the range of 2500 μm$^2$ to 81 mm$^2$, and wherein the cell addition port area is in the range of 900 μm$^2$ to 9 mm$^2$.

41. The microfluidic gradient device of claim 39, useful for chemotaxis assays, wherein the gradient height is in the range of 15 μm to 200 μm, wherein the gradient width is in the range of 100 μm to 3 mm, wherein the gradient length is in the range of 500 μm to 4 mm, wherein circuit height is in the range of 100 μm to 2 mm, wherein the circuit width is in the range of 500 μm to 4 mm, wherein the circuit length is in the range of 3 mm to 30 mm, wherein the auxiliary height is in the range of 100 μm to 2 mm, wherein the auxiliary width is in the range of 500 μm to 4 mm, wherein the auxiliary length is in the range of 500 μm to 5 mm, wherein the gradient transverse cross-sectional area is in the range of 1500 μm$^2$ to $6\times10^5$ μm$^2$, wherein the circuit transverse cross-sectional area is in the range of $1\times10^5$ μm$^2$ to $8\times10^6$ μm$^2$, wherein the auxiliary transverse cross-sectional area is in the range of $5\times10^4$ μm$^2$ to $8\times10^6$ μm$^2$, wherein the source port area is in the range of 2500 μm$^2$ to 9 mm$^2$, wherein the sink port area is in the range of $1\times10^4$ μm$^2$ to 81 mm$^2$, and wherein the cell addition port area is in the range of 2500 μm$^2$ to 9 mm$^2$.

42. The microfluidic gradient device of claim 39, wherein the gradient height is around 40 μm, wherein the gradient width is around 0.3 mm, wherein the gradient length is around 1.5 mm, wherein circuit height is around 0.25 mm, wherein the circuit width is around 1 mm, wherein the circuit length is around 17 mm, wherein auxiliary height is around 250 μm, wherein the auxiliary width is around 1 mm, wherein the auxiliary length is around 1 mm, wherein the gradient transverse cross-sectional area is around $1.2\times10^4$ μm$^2$, wherein the circuit transverse cross-sectional area is around $2.5\times10^5$ μm$^2$, wherein the auxiliary transverse cross-sectional area is around $2.5\times10^5$ μm$^2$, wherein the ratio of the (gradient flow resistance):(circuit flow resistance) is around 100:1, wherein the gradient liquid volume is around 20 nL, wherein the circuit liquid volume is around 4 μL, wherein the gradient flow resistance is around $1.2\times10^{12}$ N-s-m$^{-5}$, wherein the circuit flow resistance is around $1\times10^{10}$ N-s-m$^{-5}$, wherein the auxiliary flow resistance is around $5\times10^9$ N-s-m$^{-5}$, wherein the source liquid volume is around 0.5 μL, wherein the sink liquid volume is around 5 μL, wherein the source input liquid volume is around 0.3 μL, wherein the source port area is around 0.8 mm$^2$, wherein the sink port area is around 3 mm$^2$, and, wherein the cell addition port area is around 0.2 mm$^2$.

43. The microfluidic gradient device of any one of claims 39-42, wherein the inner surface of the gradient channel has a gradient contact angle in the range of 0° to 60°, wherein the inner surface of the closed-circuit channel has a closed-circuit contact angle in the range of 0° to 60°, and wherein the inner surface of the auxiliary channel has a gradient contact angle in the range of 0° to 60°.

44. The microfluidic gradient device of any one of claims 39-42, wherein the source port radius of curvature, the cell addition port radius of curvature, and the sink port radius of curvature are equal when gradient, circuit, and auxiliary liquid volumes are in flow equilibrium.

45. The microfluidic gradient device of any one of claims 39-42, wherein the transverse cross-sectional shape of the gradient channel is rectangular or curvalinear, wherein the longitudinal cross-sectional shape of the gradient channel is rectangular or curvalinear, wherein the transverse cross-sectional shape of the closed circuit channel is rectangular or curvalinear, wherein the longitudinal cross-sectional shape of the closed circuit channel is rectangular or curvalinear, and wherein the transverse cross-sectional shape of the auxiliary channel is rectangular or curvalinear, wherein the longitudinal cross-sectional shape of the auxiliary channel is rectangular or curvalinear.

46. The microfluidic gradient device of any of claims 39-42, wherein the shape of the source port perimeter is rectangular, polygonal or curvilinear, wherein the shape of the cell addition port perimeter is rectangular, polygonal or curvilinear, and wherein the shape of the sink port perimeter is rectangular, polygonal or curvilinear.

47. The microfluidic gradient device of any one of claims 39-42, constructed from poly(dimethylsiloxane) bonded to glass, or polystyrene bonded to a polystyrene film, or cyclo-olefin polymer bonded to cyclo-olefin polymer film, or cyclo-olefin co-polymer bonded to cyclo-olefin co-polymer film.

48. The microfluidic gradient device of any one of claims 39-42, wherein the sink assembly further comprises an air vent port, having an air vent port area in the range of 900 $\mu m^2$ to 9 $mm^2$, and where the air vent port is connected to the sink reservoir.

49. A microfluidic gradient device comprising:

a source assembly adapted to contain a source liquid volume in the range of 75 pL to 110 μL defining a source assembly air/liquid interface having a source assembly radius of curvature comprising:

a source port having a source port area and source port perimeter in fluid communication with a source input reservoir;

a source auxiliary channel in fluid communication with the source input reservoir and a source reservoir having an auxiliary height, auxiliary width, auxiliary length, auxiliary transverse cross-sectional area, auxiliary flow resistance in the range of $1\times10^6$ to $1\times10^{15}$ N-s-$m^{-5}$, and, auxiliary contact angle;

a sink assembly adapted to contain a sink liquid volume in the range of 500 pL to 100 μL defining a sink assembly air/liquid interface having a sink assembly radius of curvature comprising a sink port having a sink port area and a sink port perimeter in fluid communication with a sink reservoir;

a gradient assembly adapted to contain a gradient assembly liquid volume in the range of 25 pL to 11 μL defining a gradient assembly air/liquid interface comprising:

a cell addition port having a cell addition port area and cell addition port perimeter in fluid communication with a cell addition reservoir;

a gradient channel adapted to contain a gradient channel liquid volume in fluid communication with the cell addition reservoir, source reservoir and sink reservoir having a gradient height, gradient width, gradient length, gradient transverse cross-sectional area, gradient flow resistance in the range of $1\times10^8$ to $1\times10^{18}$ N-s-$m^{-5}$, and gradient contact angle; and a closed circuit channel adapted to contain a circuit liquid volume in the range of 50 pL to 400 μL having a circuit height, circuit width, circuit length, circuit transverse cross-sectional area, circuit flow resistance in the range of $1\times10^6$ to $1\times10^{15}$ N-s-$m^{-5}$, and, circuit contact angle, the closed circuit channel in fluid communication with the source reservoir and sink reservoir, wherein the ratio of the (gradient flow resistance):(circuit flow resistance) is in the range of (10-10,000):1.

50. The microfluidic gradient device of claim 49, wherein the gradient height is in the range of 1 μm to 200 μm, wherein the gradient width is in the range of 10 μm to 3 mm, wherein the gradient length is in the range of 50 μm to 10 mm, wherein circuit height is in the range of 10 μm to 2 mm, wherein the circuit width is in the range of 50 μm to 4 mm, wherein the circuit length is in the range of 100 μm to 50 mm, wherein the auxiliary height is in the range of 10 μm to 2 mm, wherein the auxiliary width is in the range of 50 μm to 4 mm, wherein the auxiliary length is in the range of 50 μm to 10 mm, wherein the gradient transverse cross-sectional area is in the range of 10 $\mu m^2$ to $6\times10^5$ $\mu m^2$, wherein the circuit transverse cross-sectional area is in the range of 500 $\mu m^2$ to $8\times10^6$ $\mu m^2$, wherein the auxiliary transverse cross-sectional area is in the range of 500 $\mu m^2$ to $8\times10^6$ $\mu m^2$, wherein the source port area is in the range of 900 $\mu m^2$ to 9 $mm^2$, wherein the sink port area is in the range of 2500 $\mu m^2$ to 81 $mm^2$, and wherein the cell addition port area is in the range of 900 $\mu m^2$ to 9 $mm^2$.

51. The microfluidic gradient device of claim 49, useful for chemotaxis assays, wherein the gradient height is in the range of 15 μm to 200 μm, wherein the gradient width is in the range of 100 μm to 3 mm, wherein the gradient length is in the range of 500 μm to 4 mm, wherein circuit height is in the range of 100 μm to 2 mm, wherein the circuit width is in the range of 500 μm to 4 mm, wherein the circuit length is in the range of 3 mm to 30 mm, wherein the auxiliary height is in the range of 100 μm to 2 mm, wherein the auxiliary width is in the range of 500 μm to 4 mm, wherein the auxiliary length is in the range of 500 μm to 5 mm, wherein the gradient transverse cross-sectional area is in the range of 1500 $\mu m^2$ to $6\times10^5$ $\mu m^2$, wherein the circuit transverse cross-sectional area is in the range of $1\times10^5$ $\mu m^2$ to $8\times10^6$ $\mu m^2$, wherein the auxiliary transverse cross-sectional area is in the range of $5\times10^4$ $\mu m^2$ to $8\times10^6$ $\mu m^2$, wherein the source port area is in the range of 2500 $\mu m^2$ to 9 $mm^2$, wherein the sink port area is in the range of $1\times10^4$ $\mu m^2$ to 81 $mm^2$, and wherein the cell addition port area is in the range of 2500 $\mu m^2$ to 9 $mm^2$.

52. The microfluidic gradient device of any one of claims 49-51, wherein the transverse cross-sectional shape of the gradient channel is rectangular or curvalinear, wherein the longitudinal cross-sectional shape of the gradient channel is rectangular or curvalinear, wherein the transverse cross-sectional shape of the closed circuit channel is rectangular or curvalinear, wherein the longitudinal cross-sectional shape of the closed circuit channel is rectangular or curvalinear, and wherein the transverse cross-sectional shape of the auxiliary channel is rectangular or curvalinear, wherein the longitudinal cross-sectional shape of the auxiliary channel is rectangular or curvalinear.

53. The microfluidic gradient device of any of claims 49-51, wherein the shape of the source port perimeter is rectangular, polygonal or curvilinear, wherein the shape of the cell addition port perimeter is rectangular, polygonal or curvilinear, and wherein the shape of the sink port perimeter is rectangular, polygonal or curvilinear.

54. A microfluidic gradient device comprising:

a source assembly adapted to contain a source liquid volume in the range of 75 pL to 110 μL defining a source assembly air/liquid interface having a source assembly radius of curvature comprising:

a source port having a source port area and source port perimeter in fluid communication with a source input reservoir;

a source auxiliary channel in fluid communication with the source input reservoir and a source reservoir having an auxiliary height, auxiliary width, auxiliary length, auxiliary transverse cross-sectional area, auxiliary flow resistance in the range of $1\times10^6$ to $1\times10^{15}$ N-s-$m^{-5}$, and, auxiliary contact angle;

a sink assembly adapted to contain a sink liquid volume in the range of 500 pL to 100 μL defining a sink assembly air/liquid interface having a sink assembly radius of curvature comprising a sink port having a sink port area and a sink port perimeter in fluid communication with a sink reservoir;

a gradient channel adapted to contain a gradient channel liquid volume in the range of 500 fL to 6 μL in fluid communication with the source reservoir and sink reservoir having a gradient height, gradient width, gradient length, gradient transverse cross-sectional area, gradient flow resistance in the range of $1\times10^8$ to $1\times10^{18}$ N-s-$m^{-5}$, and gradient contact angle;

a closed circuit channel adapted to contain a circuit liquid volume in the range of 50 pL to 400 μL having a circuit height, circuit width, circuit length, circuit transverse cross-sectional area, circuit flow resistance in the range of $1\times10^6$ to $1\times10^{15}$ N-s-m$^{-5}$, and, circuit contact angle, the closed circuit channel in fluid communication with the source reservoir and sink reservoir;

a cell seeding assembly adapted to contain a cell seeding assembly liquid volume in the range of 30 pL to 65 μL defining a cell seeding assembly air/liquid interface having a cell seeding assembly radius of curvature comprising:

a cell addition port having a cell addition port area and a cell addition port perimeter in fluid communication with a cell addition reservoir in fluid communication with a cell addition reservoir; and a cell addition channel in fluid communication with the gradient channel having a cell addition height, cell addition width, cell addition length, cell addition transverse cross-sectional area, and, cell addition flow resistance in the range of $5\times10^6$ to $6\times10^{13}$ N-s-m$^{-5}$, wherein the ratio of the (gradient flow resistance):(circuit flow resistance) is in the range of (10-10,000):1.

55. The microfluidic gradient device of claim 54, wherein the gradient height is in the range of 1 μm to 200 μm, wherein the gradient width is in the range of 10 μm to 3 mm, wherein the gradient length is in the range of 50 μm to 10 mm, wherein circuit height is in the range of 10 μm to 2 mm, wherein the circuit width is in the range of 50 μm to 4 mm, wherein the circuit length is in the range of 100 μm to 50 mm, wherein the auxiliary height is in the range of 10 μm to 2 mm, wherein the auxiliary width is in the range of 50 μm to 4 mm, wherein the auxiliary length is in the range of 50 μm to 10 mm, wherein the cell addition height is in the range of 10 μm to 2 mm, wherein the cell addition width is in the range of 10 μm to 3 mm, wherein the cell addition length is in the range of 50 μm to 10 mm, wherein the gradient transverse cross-sectional area is in the range of 10 μm$^2$ to $6\times10^5$ μm$^2$, wherein the circuit transverse cross-sectional area is in the range of 500 μm$^2$ to $8\times10^6$ μm$^2$, wherein the auxiliary transverse cross-sectional area is in the range of 500 μm$^2$ to $8\times10^6$ μm$^2$, wherein the cell addition transverse cross-sectional area is in the range of 100 μm$^2$ to $6\times10^6$ μm$^2$, wherein the source port area is in the range of 900 μm$^2$ to 9 mm$^2$, wherein the sink port area is in the range of 2500 μm$^2$ to 81 mm$^2$, and wherein the cell addition port area is in the range of 900 μm$^2$ to 9 mm$^2$.

56. The microfluidic gradient device of claim 54, useful for chemotaxis assays, wherein the gradient height is in the range of 15 μm to 200 μm, wherein the gradient width is in the range of 100 μm to 3 mm, wherein the gradient length is in the range of 500 μm to 4 mm, wherein circuit height is in the range of 100 μm to 2 mm, wherein the circuit width is in the range of 500 μm to 4 mm, wherein the circuit length is in the range of 3 mm to 30 mm, wherein the auxiliary height is in the range of 100 μm to 2 mm, wherein the auxiliary width is in the range of 500 μm to 4 mm, wherein the auxiliary length is in the range of 500 μm to 5 mm, wherein the cell addition height is in the range of 100 μm to 2 mm, wherein the cell addition width is in the range of 100 μm to 3 mm, wherein the cell addition length is in the range of 500 μm to 4 mm, wherein the gradient transverse cross-sectional area is in the range of 1500 μm$^2$ to $6\times10^5$ μm$^2$, wherein the circuit transverse cross-sectional area is in the range of $1\times10^5$ μm$^2$ to $8\times10^6$ μm$^2$, wherein the auxiliary transverse cross-sectional area is in the range of $5\times10^4$ μm$^2$ to $8\times10^6$ μm$^2$, wherein the cell addition transverse cross-sectional area is in the range of $2\times10^4$ μm$^2$ to $6\times10^6$ μm$^2$, wherein the source port area is in the range of 2500 μm$^2$ to 9 mm$^2$, wherein the sink port area is in the range of $1\times10^4$ μm$^2$ to 81 mm$^2$, and wherein the cell addition port area is in the range of 2500 μm$^2$ to 9 mm$^2$.

57. The device of claim 1, 11, 21, 29, 39, 49, or 54 wherein the radius of curvature at equilibrium is in the range of 0.01 mm to infinity, or −0.01 to negative infinity.

58. A method comprising, in any order or combination:

providing the microfluidic gradient device of claim 1;

providing a volume of source liquid in the source assembly;

providing a volume of sink liquid in the sink assembly;

providing a volume of gradient liquid in the gradient channel; and providing a volume of circuit liquid in the closed circuit channel;

wherein gradient and circuit liquid channel volumes are in flow equilibrium, and wherein the source assembly radius of curvature and the sink assembly radius of curvature are equal.

59. A method comprising, in any order or combination:

providing the microfluidic gradient device of claim 11;

providing a volume of source liquid in the source assembly;

providing a volume of sink liquid in the sink assembly;

providing a volume of gradient liquid in the gradient channel; and providing a volume of circuit liquid in the closed circuit channel;

wherein gradient and circuit liquid volumes are in flow equilibrium, and, wherein the source port radius of curvature, the sink port radius of curvature, and the cell addition port radius of curvature are equal.

60. A method comprising, in any order or combination:

providing the microfluidic gradient device of claim 26;

providing a volume of source liquid in the source assembly;

providing a volume of sink liquid in the sink assembly;

providing a volume of cell addition liquid in the cell addition assembly;

providing a volume of gradient liquid in the gradient channel; and providing a volume of circuit liquid in the closed circuit channel, wherein gradient, circuit and cell addition liquid volumes are in flow equilibrium, and wherein the source port radius of curvature, the sink port radius of curvature and cell addition port radius of curvature are equal.

61. A method comprising, in any order or combination:

providing the microfluidic gradient device of claim 29;

providing a volume of source liquid in the source assembly;

providing a volume of sink liquid in the sink assembly;

providing a volume of gradient liquid in the gradient channel; and providing a volume of circuit liquid in the closed circuit channel;

wherein gradient and circuit liquid volumes are in flow equilibrium, and wherein the source port radius of curvature and the sink port radius of curvature are equal.

62. A method comprising, in any order or combination:

providing the microfluidic gradient device of claim 39 or 49;

providing a volume of source liquid in the source assembly;

providing a volume of sink liquid in the sink assembly;

providing a volume of gradient liquid in the gradient channel; and providing a volume of circuit liquid in the closed circuit channel;

wherein gradient, circuit, and auxiliary liquid volumes are in flow equilibrium, and wherein the source port radius of curvature, the sink port radius of curvature, and the cell addition port radius of curvature are equal.

63. A method comprising, in any order or combination:

providing the microfluidic gradient device of claim 54;

providing a volume of source liquid in the source assembly;

providing a volume of sink liquid in the sink assembly;

providing a volume of cell addition liquid in the cell addition assembly;

providing a volume of gradient liquid in the gradient channel; and providing a volume of circuit liquid in the closed circuit channel;

wherein gradient, circuit, auxiliary and cell addition liquid volumes are in flow equilibrium, and wherein the source port radius of curvature, the sink port radius of curvature and cell addition port radius of curvature are equal.

64. The method of claim 58, wherein the liquids comprise phosphate buffered saline, cell culture medium such as DMEM, RPMI or EGM2MV, or cell culture media containing fetal bovine serum or fetal calf serum.

65. The method of claim 64, wherein the volume of the sink liquid, gradient liquid and/or cell addition liquid further comprises cells.

66. The method of claim 65, wherein the cells comprise primary cells or cell lines possessing the characteristics of granulocytes, or mononuclear leukocytes or human neutrophils, including any of the following types individually or in combination of two or more: primary neutrophils, primary eosinophils, primary basophils, primary lymphocytes, primary monocytes, primary macrophages, HL-60 cells, THP-1 cells, RAW 264.1 cells.

67. The method of claim 65, wherein the cells comprise adherent cells capable of migration, including primary cancer cells, cancer cell line cells, primary neuronal cells, primary vascular endothelial cells or endothelial cell-derived cell line cells.

68. The method of claim 65, wherein the cells comprise non-adherent, motile cells, such as bacteria or sperm cells.

69. The method of any one of claims 65-68, wherein the volume of the source liquid further comprises a bioactive substance, such as a chemoattractant or chemokine.

70. The method of claim 69, wherein the chemoattractant is Interleukin-8, or formyl-methionine-leucine-phenylalanine.

71. The method of claim 70, wherein the bioactive substance is epidermal growth factor, transforming growth factor-beta, ephrin, an amino acid or a combination of two or more amino acids.

72. The method of claim 58, wherein the volume of the sink liquid, gradient liquid and/or cell addition liquid further comprises beads containing biomolecules.

73. The method of claim 58, where one or more of the liquids are provided by wick-filling.

74. The method of claim 58, where one or more of the liquids are provided by pipetting to the source port, sink port or cell addition port and subsequent equilibration of fluid volumes.

75. The method of claim 58, comprising the provision of all volumes together with an assay medium fluid, and comprising, in any order, the following:

partially replacing the volume of the source assembly with a second fluid comprising chemoattractant medium; and partially replacing the volume of the sink assembly, gradient assembly or cell addition assembly with a third fluid containing a cell suspension.

76. The method of claim 58, comprising the provision of all volumes together with an assay medium fluid, and comprising, in any order, the following:

partially replacing the volume of the source assembly with a second fluid comprising chemoattractant medium;

partially replacing the volume of the sink assembly, gradient assembly or cell addition assembly with a third fluid containing a cell suspension; and partially replacing the volume of the source assembly, sink assembly, gradient assembly, cell addition assembly, gradient channel and/or closed-circuit channel with a fourth fluid containing a readout reagent.

77. The method of claim 58, wherein one or more of the steps is repeated one or more times.

78. The method of claim 58, wherein the assay medium further comprises a bio-active compound, an inhibitor or a drug.

79. The method of claim 78, wherein the readout reagent is an antibody, fluorophore-conjugated antibody, an enzyme-conjugated antibody, a histological staining reagent, an immuno-cytochemical staining reagent or an enzyme substrate.

80. The method of claim 76, wherein one or more of the liquids further comprise a fluorescent dye where the concentration of the fluorescent dye is around 0.1 mg/ml.

* * * * *

UNITED STATES PATENT AND TRADEMARK OFFICE

CERTIFICATE OF CORRECTION

PATENT NO. : 8,377,685 B2
APPLICATION NO. : 12/267524
DATED : February 19, 2013
INVENTOR(S) : Meyvantsson et al.

It is certified that error appears in the above-identified patent and that said Letters Patent is hereby corrected as shown below:

In the Specification

Column 9, line 21 "$10^3$" should read -- $10^{13}$ --

Column 13, line 26 "10 µm" should read -- 50 µm --

Column 13, line 30 "10 µm" should read -- 50 µm --

Column 13, line 31 "10 µm" should read -- 50 µm --

Column 15, line 15 "10 µL" should read -- 11 µL --

Column 15, line 30 "10 µm" should read -- 50 µm --

Column 15, line 35 "10 µm" should read -- 50 µm --

Signed and Sealed this
Thirteenth Day of August, 2013

Teresa Stanek Rea
*Acting Director of the United States Patent and Trademark Office*